US012630591B2

(12) United States Patent (10) Patent No.: US 12,630,591 B2
Brandenburg et al. (45) Date of Patent: May 19, 2026

(54) RECOMBINANT INFLUENZA ANTIGENS

(71) Applicant: JANSSEN VACCINES & PREVENTION B.V., Leiden (NL)

(72) Inventors: Boerries Brandenburg, Leiden (NL); Tina Ritschel, Leiden (NL); Ferdinand Jacobus Milder, Leiden (NL); Mandy Antonia Catharina Jongeneelen, Leiden (NL); Indigo King, Leiden (NL); Yifan Song, Leiden (NL); Johannes Petrus Maria Langedijk, Leiden (NL)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 1227 days.

(21) Appl. No.: 17/594,576

(22) PCT Filed: Apr. 23, 2020

(86) PCT No.: PCT/EP2020/061335
§ 371 (c)(1),
(2) Date: Oct. 22, 2021

(87) PCT Pub. No.: WO2020/216844
PCT Pub. Date: Oct. 29, 2020

(65) Prior Publication Data
US 2022/0204567 A1 Jun. 30, 2022

Related U.S. Application Data

(60) Provisional application No. 62/838,690, filed on Apr. 25, 2019.

(51) Int. Cl.
*C07K 14/005* (2006.01)
*A61K 39/00* (2006.01)

(52) U.S. Cl.
CPC ............ *C07K 14/005* (2013.01); *A61K 39/00* (2013.01); *A61K 2039/5256* (2013.01)

(58) Field of Classification Search
CPC .................................................... C07K 14/005
See application file for complete search history.

(56) References Cited

FOREIGN PATENT DOCUMENTS

WO 2011056802 A1 5/2011
WO 2013079473 A1 6/2013

OTHER PUBLICATIONS

Yamashita, A., et al., 2010, Highly conserved sequences for human neutralization epitope on hemagglutinin of influenza A viruses H3N2, H1N1, and H5N1: Implication for human monoclonal antibody recognition, Biochem. Biophys. Res. Comm. 393:614-618.*
International Search Report mailed Aug. 17, 2020 in PCT/EP2020/061335.
Written Opinion mailed Aug. 17, 2020 in PCT/EP2020/061335.
Eili Y. Klein, et al., "Stability of the influenza virus hemagglutinin protein correlates with evolutionary dynamics," Msphere, vol. 3, No. 1, Feb. 1, 2018.

* cited by examiner

*Primary Examiner* — Jeffrey S Parkin
(74) *Attorney, Agent, or Firm* — Ice Miller LLP

(57) ABSTRACT

The invention provides recombinant influenza A hemagglutinin (HA) polypeptides, comprising an HA1 and a HA2 domain of an influenza A virus HA, and comprising an amino acid sequence wherein:
(a) the amino acid at position 355 is W; and
(b) the amino acid at position 432 is I and/or the amino acid at position 380 is I;
and wherein the numbering of the amino acid positions in the amino acid sequence of the HA polypeptide is according to the numbering of amino acids in the amino acid sequence of HA from a reference H3N2 influenza strain, in particular the reference strain H3N2 A/Aichi/2/68 (SEQ ID NO: 1), immunogenic fragments thereof, nucleic acid molecules encoding said polypeptides or immunogenic fragments, and uses thereof.

14 Claims, 8 Drawing Sheets

Specification includes a Sequence Listing.

A

B

A

B

| HA | Strain | WT ID. | Expression (mg/L) | Stabilized ID. | Expression (mg/L) | Fold increase |
|----|--------|--------|-------------------|----------------|-------------------|---------------|
| H1 | A/California/07/2009 | UFV181157 | 80 | UFV181009 | 143 | 1.8 |
| H1 | A/Michigan/45/2015 | UFV181134 | 83 | UFV181091 | 225 | 2.7 |
| H2 | A/Env/MPU3156/2005 | UFV181153 | 63 | UFV181154 | 271 | 4.3 |
| H5 | A/Eurasian Wigeon/MPF461/2007 | UFV181158 | 42 | UFV181159 | 263 | 6.4 |
| H9 | A/Hong Kong/1073/1999 | UFV181155 | 111 | UFV181156 | 197 | 1.8 |
| H3 | A/Hong Kong/1/1968 | UFV181141 | 58 | UFV180660 | 138 | 2.4 |
| H3 | A/Panama/2007/1999 | UFV181137 | 65 | UFV181096 | 92 | 1.4 |
| H14 | A/Mallard/Astrakhan/263/1982 | UFV181145 | 79 | UFV180661 | 130 | 1.6 |
| H7 | A/Mallard/Netherlands/12/2000 | UFV181146 | 72 | UFV180664 | 178 | 2.5 |
| H10 | A/Chicken/Germany/N/1949 | UFV181147 | 44 | UFV180662 | 158 | 3.6 |

C

A

B

C

| HA | Strain | FL HA + Foldon | $Tm_{50}$ (°C) | Stabilized ID. | $Tm_{50}$ (°C) |
|----|--------|----------------|-----------|----------------|-----------|
| H1 | A/California/07/2009 | UFV4239 (monomer) | 56.5 | UFV181009 | 63.5 |
| H1 | A/Michigan/45/2015 | UFV180843 | 60.0 | UFV181091 | 67.0 |
| H3 | A/Hong Kong/1/1968 | UFV180436 | 50.9 | UFV180660 | 66.2 |
| H3 | A/Indiana/11/2011 | UFV170466 | 47.8, 56.1* | UFV181099 | 67.9 |

*biphasic melting point*

D

| Strain | Binding ELISA ($EC_{50}$, nM), N = 2 | | | | |
|--------|--------|--------|--------|--------|--------|
| | CR6261 | CR8020 | CR9114 | CT149 | MD3606 |
| H1 A/California/07/2009 | | | | | |
| UFV4239* | 1.0 ± 0.1 | >70 | 1.3 ± 0.2 | 1.6 ± 1.0 | 1.1 ± 0.1 |
| UFV181009# | 1.8 ± 0.2 | >70 | 1.4 ± 0.1 | 0.9 ± 0.2 | 2.2 ± 0.1 |
| H1 A/Michigan/45/2015 | | | | | |
| UFV180843 | 0.6 ± 0.1 | >70 | 0.9 ± 0.2 | 0.4 ± 0.1 | 0.8 ± 0.1 |
| UFV181091# | 1.3 ± 0.2 | >70 | 1.6 ± 0.1 | 0.9 ± 0.1 | 1.6 ± 0.1 |
| H3 A/Hong Kong/1/1968 | | | | | |
| UFV180436 | >70 | 1.6 ± 0.1 | 12.7 ± 3.5 | 0.9 ± 0.2 | 0.8 ± 0.1 |
| UFV180660# | >70 | 1.9 ± 0.1 | 3.0 ± 0.1 | 1.1 ± 0.1 | 0.8 ± 0.1 |
| H3 A/Indiana/11/2011 | | | | | |
| UFV170466 | >70 | 1.9 ± 0.1 | 25.0 | 0.7 ± 0.5 | 0.8 ± 0.1 |
| UFV181099# | >70 | 1.7 ± 0.4 | 2.8 ± 1.1 | 0.7 ± 0.1 | 0.9 ± 0.1 |

*Monomeric polypeptide, # Stabilized trimeric polypeptide*

| 355 | 478 | 380 | 432 | ID. | Expression (mg/L) |
|-----|-----|-----|-----|-----|-------------------|
| H | M | K | E | H1 A/California/07/2009 | 80 |
| W | I | . | . | UFV181005 | 130 |
| . | . | I | I | UFV181007 | 71 |
| W | I | I | I | UFV181009 | 143 |

B

A

| HA | Strain | WT ID. | Expression (mg/L) | Stabilized ID. | Expression (mg/L) | Fold increase |
|---|---|---|---|---|---|---|
| H1 | A/Brisbane/59/07 | UFV181135 | 147 | UFV181090 | 180 | 1.2 |
| H1 | A/South Carolina/1/1918 | UFV181131 | 175 | UFV181084 | 130 | 0.7 |
| H3 | A/Netherlands/179/1993 | UFV181140 | 14 | UFV181095 | 23 | 1.6 |
| H3 | A/Texas/1/1977 | UFV181136 | 71 | UFV181093 | 133 | 1.9 |
| H3 | A/Wisconsin/67/2005 | UFV181138 | 13 | UFV181097 | 34 | 2.6 |
| H4 | A/Great Cormorant/MBP1683/2006 | UFV181148 | 129 | UFV181149 | 223 | 1.7 |

B

RECOMBINANT INFLUENZA ANTIGENS

CROSS-REFERENCE TO RELATED APPLICATIONS

This application is a Section 371 of International Application No. PCT/EP2020/061335, filed on Apr. 23, 2020, which published in the English language on Oct. 29, 2020 under International Publication No. WO 2020/216844 A1, which claims priority to U.S. Provisional Application No. 62/838,690, filed on Apr. 25, 2019, the disclosures of which are incorporated herein by reference in their entirety.

STATEMENT AS TO FEDERALLY FUNDED RESEARCH

This invention was made, at least in part, with Government support under Agreement HHSO100201700018C, awarded by HHS. The Government has certain rights in the invention.

REFERENCE TO SEQUENCE LISTING SUBMITTED ELECTRONICALLY

This application contains a sequence listing, which is submitted electronically via EFS-Web as an ASCII formatted sequence listing with a file name "004852_138US2_Sequence_Listing" and a creation date of Oct. 13, 2021 and having a size of 209 Kb. The sequence listing submitted via EFS-Web is part of the specification and is herein incorporated by reference in its entirety.

INTRODUCTION

The invention relates to the field of medicine. Provided herein are recombinant influenza A hemagglutinin (HA) polypeptides, nucleic acids encoding said polypeptides, pharmaceutical compositions comprising the same, and methods of their use.

BACKGROUND

Influenza viruses are major human pathogens, causing a respiratory disease (commonly referred to as "influenza" or "the flu") that ranges in severity from sub-clinical infection to primary viral pneumonia which can result in death. The clinical effects of infection vary with the virulence of the influenza strain and the exposure, history, age, and immune status of the host. Every year it is estimated that approximately 1 billion people worldwide undergo infection with influenza virus, leading to severe illness in 3-5 million cases and an estimated 300,000 to 500,000 of influenza related deaths. The bulk of these infections can be attributed to influenza A viruses carrying H1 or H3 hemagglutinin subtypes, with a smaller contribution from Influenza B viruses, and therefore representatives of all three are included in the seasonal vaccine. The current immunization practice relies on early identification of circulating influenza viruses to allow for timely production of an effective seasonal influenza vaccine. Apart from the inherent difficulties in predicting the strains that will be dominant during the next season, antiviral resistance and immune escape also play a role in failure of current vaccines to prevent morbidity and mortality. In addition to this the possibility of a pandemic caused by a highly virulent viral strain originating from animal reservoirs and reassorted to increase human to human spread, poses a significant and realistic threat to global health.

Influenza A viruses are widely distributed in nature and can infect a variety of birds and mammals. Influenza viruses are enveloped RNA viruses that belong to the family of Orthomyxoviridae. Their genomes consist of eight single-stranded RNA segments that code for 11 different proteins, one nucleoprotein (NP), three polymerase proteins (PA, PB1, and PB2), two matrix proteins (M1 and M2), three non-structural proteins (NS1, NS2, and PB1-F2), and two external glycoproteins: hemagglutinin (HA) and neuraminidase (NA). The viruses are classified based on differences in antigenic structure of the HA and NA proteins, with their different combinations representing unique virus subtypes that are further classified into specific influenza virus strains. Although all known subtypes can be found in birds, currently circulating human influenza A subtypes are H1N1 and H3N2. Phylogenetic analysis has demonstrated a subdivision of hemagglutinins into two main groups: inter alia the H1, H2, H5 and H9 subtypes in phylogenetic group 1 and inter alia the H3, H4 and H7 subtypes in phylogenetic group 2.

The influenza type B virus strains are strictly human. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and B/Victoria/2/87 (B/Victoria) lineages. Although the spectrum of disease caused by influenza B viruses is generally milder than that caused by influenza A viruses, severe illness requiring hospitalization is still frequently observed with influenza B infection.

It is known that antibodies that neutralize the influenza virus are primarily directed against hemagglutinin (HA). Hemagglutinin is a trimeric glycoprotein that is anchored in the viral coat and has a dual function: it is responsible for binding to the cell surface receptor sialic acid and, after uptake, it mediates the fusion of the viral and endosomal membrane leading to release of the viral RNA into the cytosol of the cell. HA comprises a so-called head domain and stem domain. Attachment to the viral membrane is mediated by a C-terminal anchoring sequence (also known as transmembrane domain) connected to the stem domain. The protein is post-translationally cleaved in a designated loop to yield two polypeptides, HA1 and HA2 (the full sequence is referred to as HA0). The membrane distal head domain is mainly derived from HA1 and the membrane proximal stem domain primarily from HA2 (FIG. 1).

As influenza virus is ubiquitous, avoidance of infection by the virus is nearly impossible. Vaccination plays a critical role in controlling influenza epidemics and pandemics. Many influenza vaccines are made by methods that involve reassortment, adaptation and growth of viruses in chicken eggs. However, there are limitations with these existing methods. Not all influenza virus strains grow well in eggs and must be adapted or viral reassortants constructed. The changes in HA during manufacturing can lead to strains that differ from the circulating strains and that may offer suboptimal levels of protection. Another drawback is that those with egg allergies may show hypersensitivity to residual egg proteins in egg-based vaccines. Furthermore, egg-based methods rely on an uninterrupted supply of eggs, which can be susceptible to disruptions in supply such as in case of disease in poultry. There is a need for production of vaccines using methods that do not rely on egg supply and where vaccine protein production is more stringently controlled than in egg-based methods. Recombinant forms of HA (rHA) produced in cell cultures are used as an alternative source of antigen for influenza vaccines to that sourced from eggs. However, problems maintaining immunogenicity and a regular quaternary structure of rHA as well as ensuring high yields of trimeric rHA have been encountered using these methods. There is thus still a need for alternative methods of antigen supply for influenza vaccines or for diagnostics, that address the existing challenges.

SUMMARY OF THE INVENTION

Some aspects of the present invention are summarized below. Additional aspects are described in the Detailed Description of the Invention, the Examples, the Figures, and the Claims sections of the present patent application.

In a first aspect, the present invention relates to recombinant influenza A hemagglutinin (HA) polypeptides, comprising an HA1 and a HA2 domain of an influenza A virus HA, and comprising an amino acid sequence wherein:

(a) the amino acid at position 355 is tryptophan (W); and (b) the amino acid at position 432 is isoleucine (I) and/or the amino acid at position 380 is I;

and wherein the numbering of the amino acid positions in the amino acid sequence of the HA polypeptide is according to the numbering of amino acids in the amino acid sequence of HA from a reference H3N2 influenza strain, in particular the reference strain H3N2 A/Aichi/2/68 (SEQ ID NO: 1).

In a further aspect, the invention relates to multimeric polypeptides comprising at least two HA polypeptides, in particular to trimeric polypeptides, comprising three HA polypeptides as described herein.

According to the present invention it has surprisingly been shown that the recombinant influenza HA polypeptides, in particular recombinant trimeric HA polypeptides, can be obtained in high levels, and have an increased melting temperature indicating a greater stability, as compared to wild-type HA polypeptides, without the addition of heterologous amino acid sequences, such as heterologous trimerization domains. In addition, the HA polypeptides of the invention are correctly folded as shown by binding of anti-HA antibodies to the HA polypeptides, such as, but not limited to the antibodies CR9114, CR8020 and/or CR6261. The polypeptides thus can induce an immune response against HA when administered to a subject, in particular a human subject. The trimeric polypeptides comprise the quaternary structure of a wild-type native HA, and thus present the natural epitopes, including the conserved epitopes of the membrane proximal stem of the HA molecule, to the immune system.

In a further aspect, the present invention provides nucleic acid molecules encoding the recombinant influenza HA polypeptides.

In yet another aspect, the invention provides vectors, in particular recombinant adenoviral vectors, comprising nucleic acid molecules encoding the influenza HA polypeptides.

In another aspect, the invention provides immunogenic compositions comprising an influenza HA polypeptide, a nucleic acid molecule and/or a vector according to the invention, and a pharmaceutically acceptable carrier.

In a further aspect, the invention provides influenza HA polypeptides, nucleic acid molecules encoding said influenza HA polypeptides, and/or vectors comprising said nucleic acid molecules for use as a medicament, in particular for use as a vaccine for the prevention and/or treatment of an influenza disease, in particular a disease or condition caused by an influenza virus A strain from phylogenetic group 1 and/or 2.

The invention also provides methods for inducing an immune response against influenza HA in a subject in need thereof, the method comprising administering to the subject an influenza HA polypeptide, a nucleic acid molecule, and/or a vector according to the invention. In yet a further aspect, methods are provided for prevention and/or vaccination against influenza disease, comprising the administration of a polypeptide or immunogenic composition as described above to a person in need thereof, such as a person identified as being at risk of being infected with influenza disease.

In still a further aspect there is provided a method for producing a recombinant HA polypeptide as defined above comprising expressing a nucleic acid molecule described above in a prokaryotic or eukaryotic cell, such as a mammalian cell, e.g. a CHO cell, or an insect cell, optionally further comprising purifying/isolating the rHA from said cell.

In yet another aspect, the invention provides the use of the HA polypeptides as research tools or diagnostic tools, or as targets for the production of influenza inhibiting agents of antibodies.

DEFINITIONS

Figure 1:
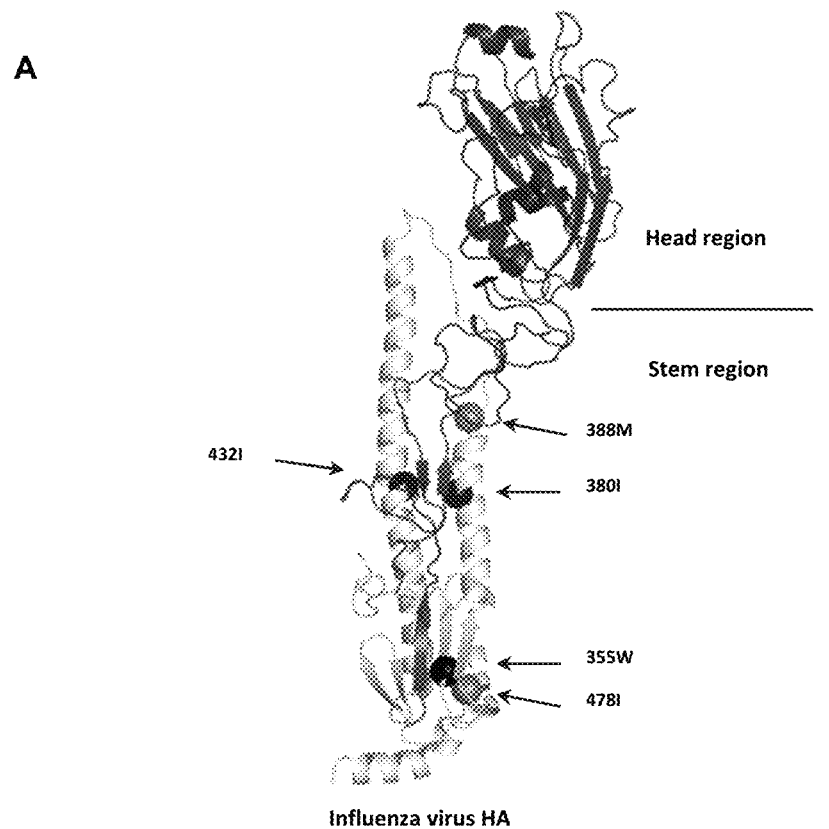
FIG. 1. A. Three-dimensional representation of a polypeptide monomer of the invention with the positions of the mutations indicated. Head of haemagglutinin (HA) in dark gray stein in light gray; B. Schematic drawing of polypeptide monomer (black: head; light grey: stem) of the invention with the positions of the mutations indicated.
Figure 1:
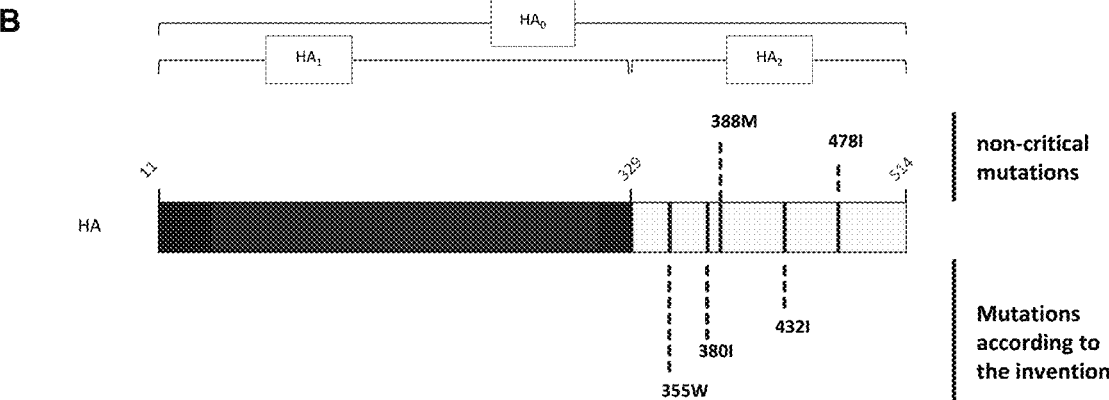

Definitions of terms as used in the present invention are given below.

An amino acid according to the invention can be any of the twenty naturally occurring (or 'standard' amino acids) or variants thereof, such as e.g. D-proline (the D-enantiomer of proline), or any variants that are not naturally found in proteins, such as e.g. norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 3 shows the abbreviations and properties of the standard amino acids.

The term "included" or "including" as used herein is deemed to be followed by the words "without limitation".

As used herein, the term "infection" means the invasion by, multiplication, and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

Influenza viruses are typically classified into influenza virus types: genus A, B and C. The term "influenza virus subtype" as used herein refers to influenza A virus variants that are characterized by combinations of the hemagglutinin (H) and neuramidase (N) viral surface proteins. According to the present invention influenza virus subtypes may be referred to by their H number, such as for example "influenza virus comprising HA of the H3 subtype", "influenza virus of the H3 subtype" or "H3 influenza", or by a combination of a H number and an N number, such as for example "influenza virus subtype H3N2" or "H3N2". The term "subtype" specifically includes all individual "strains", within each subtype, which usually result from mutations and show different pathogenic profiles, including natural isolates as well as man-made mutants or reassortants and the like. Such strains may also be referred to as various "isolates" of a viral subtype. Accordingly, as used herein, the terms "strains" and "isolates" may be used interchangeably. The current nomenclature for human influenza virus strains or isolates includes the type (genus) of virus, i.e. A, B or C, the geographical location of the first isolation, strain number and year of isolation, usually with the antigenic description of HA and NA given in brackets, e.g. A/Moscow/10/2000 (H3N2). Non-human strains also include the host of origin in the nomenclature.

The influenza A virus subtypes can further be classified by reference to their phylogenetic group. Phylogenetic analysis has demonstrated a subdivision of hemagglutinins into two main groups: inter alia the H1, H2, H5 and H9 subtypes in phylogenetic Group 1 ("Group 1" influenza viruses) and inter alia the H3, H4, H7 and H10 subtypes in phylogenetic Group 2 ("Group 2" influenza viruses).

As used herein, the term "influenza virus disease" or "influenza" refers to the pathological condition resulting from the presence of an influenza virus, e.g. an influenza A or B virus, in a subject. As used herein, the terms "disease" and "disorder" are used interchangeably. In specific embodiments, the term refers to a respiratory illness caused by the infection of the subject by the influenza virus.

As used herein, the term "nucleic acid" or "nucleic acid molecule" is intended to include polynucleotides, such as DNA molecules (e.g., cDNA or genomic DNA) and RNA molecules (e.g., mRNA) and analogs of the DNA or RNA generated using nucleotide analogs. The nucleic acid can be single-stranded or double-stranded. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

As used herein, the numbering of the amino acids in HA is based on H3 numbering, as described by Winter et al. (Nature 292: 72-75, 1981). The numbering of the amino acid residues or amino acid positions in the polypeptides of the invention thus corresponds to the numbering of the amino acids in H3 HA (in particular, the numbering of amino acid positions in HA of A/Aichi/2/68), as described by and shown in FIG. 2 in Winter et al. (1981)). The numbering in particular corresponds to the numbering of the amino acid positions in SEQ ID NO: 1. For example, the wording 'the amino acid at position 355" refers to the amino acid residue that is at position 355 according to the H3 numbering of Winter et al. (1981), i.e. to the amino acid residue that is at position 355 in SEQ ID NO: 1. It will be understood by the skilled person that equivalent amino acids in other influenza virus strains and/or subtypes, such as in e.g. H1, H5, or H7 HA, can be determined by sequence alignment. Thus, it should be noted, and one of skill in the art will understand, that different HA sequences may have different numbering systems, for example, if there are additional amino acid residues added or removed as compared to SEQ ID NO: 1. As such, it is to be understood that when specific amino acid residues are referred to by their number, the description is not limited to only amino acids located at precisely that numbered position when counting from the beginning of a given amino acid sequence, but rather that the equivalent/corresponding amino acid residue in any and all HA sequences is intended—even if that residue is not at the same precise numbered position, for example if the HA sequence is shorter or longer than SEQ ID NO: 1, or has insertions or deletions as compared to SEQ ID NO: 1. One of skill in the art can readily determine what is the corresponding/equivalent amino acid position to any of the specific numbered residues recited herein, for example by aligning a given HA sequence to SEQ ID NO: 1. Thus, in embodiments where specific amino acid residues of the influenza HA protein are referred to, it is to be understood that the invention is not to be limited to sequences having the specified amino acid residue (e.g. presence of a tryptophan (W) at position 355 and/or an isoleucine (I) at position 432 and/or 380) at only those precise numbered amino acid positions.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked and O-linked glycosylation), protease cleavage and lipid modification (e.g. S-palmitoylation).

As used herein, the term "wild-type" refers to HA from influenza viruses that are circulating naturally.

DETAILED DESCRIPTION OF THE INVENTION

Influenza viruses have a significant impact on global public health, causing millions of cases of severe illness each year, thousands of deaths, and considerable economic losses. Current trivalent influenza vaccines elicit a potent neutralizing antibody response to the vaccine strains and closely related isolates, but rarely extend to more diverged strains within a subtype or to other subtypes. In addition, selection of the appropriate vaccine strains presents many challenges and frequently results in sub-optimal protection. Furthermore, predicting the subtype of the next pandemic virus, including when and where it will arise, is currently impossible.

Hemagglutinin (HA) is the major envelope glycoprotein from influenza A viruses which is the major target of neutralizing antibodies. Hemagglutinin has two main functions during the entry process. First, hemagglutinin mediates attachment of the virus to the surface of target cells through interactions with sialic acid receptors. Second, after endocytosis of the virus, hemagglutinin subsequently mediates the fusion of the viral and endosomal membranes to release its genome into the cytoplasm of the target cell.

HA is a trimeric protein comprising an ectodomain of about 500 amino acids per monomer and comprises three identical subunits (monomers) each of which contains two polypeptides, HA1 and HA2, linked by a disulfide bond. Each monomer is initially expressed as HA0 and is subsequently cleaved by host proteases into the HA1 and HA2 domains which are linked via said disulfide bond.

The majority of the N-terminal domain (the HA1 domain, about 320-330 amino acids in length) forms a membrane-distal globular domain (the head domain) that contains the receptor-binding site and most epitopes recognized by virus-neutralizing antibodies. The smaller C-terminal domain (the HA2 domain, ~180 amino acids in length) forms a stem-like structure (the stem domain) that anchors the globular domain in the cellular or viral membrane. One of the most conserved regions is the sequence around the cleavage site, particularly the HA2 N-terminal 23 amino acids (the fusion peptide), which is conserved among all influenza A virus subtypes. Part of this region is exposed as a surface loop in the HA precursor molecule (HA0) but becomes inaccessible when HA0 is cleaved into HA1 and HA2.

As stated above, influenza HA protein is the primary protein found on the surface of the virus. The HA found on the surface of the virion is in a trimeric form. The trimer is anchored in the viral membrane by transmembrane spanning sequences at the carboxy-terminal end of each of the three monomers. The main protective efficacy of influenza vaccines is attributed to anti-hemagglutinin antibodies directed to the HA protein. This highlights the importance of raising an immune response to conformationally relevant HA proteins.

To produce soluble polypeptides representing the ectodomain of influenza A virus hemagglutinin (HA0), the HA needs to be expressed without its native transmembrane and cytoplasmic domain. Expression of stable trimeric soluble wild type (WT) HA is often very poor in mammalian cells. To improve at least the level of trimerization, a heterologous trimerization domain (e.g. a Foldon trimerization domain; Stevens et al. Science 303(5665):1866-1870, 2004) is often genetically fused to the C-terminus of the polypeptide. Unfortunately, the addition of a heterologous trimerization domain introduces an unwanted neoepitope and often reduces the expression level or may alter the quaternary structure of the polypeptide.

The present invention provides stable recombinant influenza A hemagglutinin (HA) polypeptides, comprising an HA1 and a HA2 domain of an influenza A virus HA, and comprising an amino acid sequence wherein:

(a) the amino acid at position 355 is W; and (b) the amino acid at position 432 is I and/or the amino acid at position 380 is I;

and wherein the numbering of the amino acid positions in the amino acid sequence of the HA polypeptide is according to the numbering of amino acids in the amino acid sequence of HA from a reference H3N2 influenza strain, in particular the reference strain H3N2 A/Aichi/2/68 (SEQ ID NO: 1).

According to the invention, it has surprisingly been found that stable recombinant HA polypeptides, in particular soluble HA trimeric polypeptides, without addition of a Foldon domain or any other heterologous trimerization domains can be obtained, by the presence of specific amino acid mutations in the core of the HA polypeptide.

In certain aspects, the present invention thus provides recombinant influenza A hemagglutinin (HA) polypeptides, comprising an HA1 and a HA2 domain of an influenza A virus HA, and comprising an amino acid sequence wherein:

(a) the amino acid at position 355 is mutated into W; and (b) the amino acid at position 432 is mutated into I and/or the amino acid at position 380 is mutated into I;

and wherein the numbering of the amino acid positions in the amino acid sequence of the HA polypeptide is according to the numbering of amino acids in the amino acid sequence of HA from a reference H3N2 influenza strain, in particular the reference strain H3N2 A/Aichi/2/68 (SEQ ID NO: 1). Since the mutations are "buried" mutations, i.e. the side chains of these residues are not exposed on the protein surface, the antigenicity of the HA polypeptides will not change.

In certain embodiments, the polypeptides comprise a mutation of the amino acid at position 355, in particular histidine (H), into tryptophan (W) and a mutation of the amino acids at positions 432 and/or 380 into isoleucine (I).

The HA polypeptides of the present invention, having the amino acid residue W at position 355, e.g. by introducing a mutation of the amino acid at position 355, in particular H, into W; in combination with the amino acid I at position 432, e.g. by introducing a mutation of the amino acid at position 432 into I; or having a combination of an I at position 432 and an I at position 380, e.g. by introducing a mutation at positions 432 and 380 into I, show an increased level of expression in mammalian cells, an increased propensity to trimerize (e.g. as measured by AlphaLISA, Octet, and SEC), and/or an increased level of thermo-stability (e.g. as measured by, Dynamic Scanning Fluorimetry/Calorimetry (DSF/DSC)), as compared to the HA polypeptides without these amino acid mutations. In addition, the binding strength of all tested antibodies to the polypeptides of the invention is less than SnM (measured by Octet and ELISA). This clearly shows that the polypeptides are structurally equivalent (with respect to primary-, secondary-, tertiary- and quaternary-structure) to the native, wild type HA. The novel HA polypeptides furthermore do not require the presence of any artificial (heterologous) sequences such as linker-, tag-, or trimerization domain-sequences.

In certain embodiments, the polypeptides comprise a mutation of the amino acid at position 355, in particular histidine (H), into tryptophan (W) and a mutation of the amino acids at positions 432 and/or 380 into isoleucine (I).

In certain embodiments, the HA polypeptides comprise an amino acid sequence wherein:

(a) the amino acid at position 388 is M; and/or (b) the amino acid at position 478 is I.

It has been shown that these mutations, at least in certain HA subtypes, further increase the stability of the HA polypeptides, In certain embodiments, said HA monomers do not comprise a protease cleavage site. As described above, cleavage of the influenza HA0 protein (in HA1 and HA2) is required for its activity, facilitating the entry of the viral genome into the target cells by causing the fusion of the host endosomal membrane with the viral membrane. In certain embodiments, the polypeptides of the invention comprise the natural protease cleavage site. Thus, it is known that the Arg (R)-Gly (G) sequence spanning HA1 and HA2 (i.e. amino acid positions 329 and 330) is a recognition site for trypsin and trypsin-like proteases and is typically cleaved for hemagglutinin activation (FIG. 1A). In certain embodiments, the protease cleavage site has been removed by mutation of the amino acid residue at position 329 into any amino acid other than arginine (R) or lysine (K). In certain embodiments, the amino acid residue at position 329 is not arginine (R). In a preferred embodiment, the polypeptides comprise a mutation of the amino acid at position 329 into glutamine (Q). Thus, in certain embodiments, the polypeptides of the invention comprise the cleavage site knock-out mutation R329Q to prevent putative cleavage of the molecule during or after production in vitro or in vivo after administration. The cleavage site knock-out mutation, e.g. the R329Q mutation, thereby ensures insensitivity towards low pH triggered conformational changes and preserves the pre-fusion conformation of HA.

According to the invention, the HA1 and/or HA2 domain may comprise the complete (i.e. full length) HA1 and/or HA2 domain of an influenza HA polypeptide, or they may comprise at least part of an HA1 and/or an HA2 domain.

To produce secreted (soluble) HA polypeptides, in certain embodiments the HA monomers comprise a truncated HA2 domain. Thus, in certain embodiments the HA monomers in the polypeptides of the invention do not comprise the transmembrane and cytoplasmic domain. In particular, in certain embodiments, the polypeptide monomers comprise an HA2 domain that is truncated at the C-terminal end. A truncated HA2 domain according to the invention thus is shorter than the full length HA2 sequence, by deletion of one or more amino acid residues at the C-terminal and/or N-terminal end of the HA2 domain. Thus, the invention further also provides recombinant HA polypeptides comprising or consisting of the extracellular domain of HA (ectodomain, ECD).

In certain embodiments, the C-terminal part of the HA2 domain starting with the amino acid corresponding to the amino acid at position 515 has been deleted, thus removing substantially the full transmembrane and cytoplasmic domain.

In certain embodiments, also one or more amino acids at the C-terminus of the ectodomain have been deleted. According to the present invention it has been found that even when a larger part of the HA2 domain is deleted, stable soluble and trimeric HA polypeptides can be provided. Thus, in certain embodiments, the C-terminal part of the HA2 domain starting at the amino acid sequence at position 500, 501, 502, 503, 504, 505, 506, 507, 508, 509, 510, 511, 512, 513, or 514 has been deleted (according to H3 numbering as described by Winter et al., supra) to produce a soluble polypeptide following expression in cells.

Similarly, the HA1 domain may be the complete (i.e. full length HA1 domain) or at least part thereof. In certain embodiment, the polypeptides comprise a truncated HA1 domain. The HA1 domain may be truncated at the N- and/or C-terminal end of the HA1 domain.

In certain embodiments, the HA polypeptides do not comprise a signal sequence. The signal sequence (sometimes referred to as signal peptide, targeting signal, localization signal, localization sequence, transit peptide, leader sequence or leader peptide) is a short peptide (usually 16-30 amino acids long) that is present at the N-terminus of the majority of newly synthesized proteins that are destined towards the secretory pathway. Signal sequences function to prompt a cell to translocate the protein, usually to the cellular membrane. In many instances the amino acids comprising the signal peptide are cleaved off the protein once its final destination has been reached. In influenza HA, the signal sequences typically comprise the first 16 amino acids of the amino acid sequence of the full-length HA0 (corresponding to the amino acids from position −6 to position 10 according to H3 numbering).

The present invention also provides immunogenic fragments of the HA polypeptides. In certain embodiments, at least part of the HA1 domain making up the head domain may have been deleted to provide immunogenic fragments of the HA polypeptides of the invention, such as headless HA polypeptides (i.e. stem-only polypeptides).

The polypeptides of the invention represent (are derived from) the influenza virus hemagglutinin (HA) of influenza A viruses. As described above, influenza A contains multiple subtypes of HA that can be divided into two main groups, Group 1 and Group 2 (FIG. 2A). The stabilizing mutations in the polypeptides of the invention can be applied to all hemagglutinin types of Influenza A.

In certain embodiments, the HA1 and HA2 domain are from a Group 1 or a Group 2 influenza A virus. In certain embodiments, the HA1 and HA2 domain are from the same Group 1 or Group 2 virus. In certain other embodiments, the HA1 and HA2 domain are from different Group 1 or from different Group 2 viruses, or the HA1 and HA2 domain are from influenza A viruses from different Groups, e.g. the HA2 domain is from a group 1 virus and the HA2 domain is from a Group 2 virus, or vice versa. In certain embodiments, the head domain (i.e. at least the part of the HA1 domain forming the head domain is from a different influenza virus than the stem domain (i.e. the part of the HA2 domain forming the stem domain of the influenza HA polypeptide).

In certain particular embodiments, the HA1 and/or HA2 domains are from an influenza A virus selected from the Group consisting of: an influenza virus comprising HA of the H1 subtype, e.g. from the influenza virus A/California/07/2009 or A/Michigan/45/2015; an influenza virus comprising HA of the H2 subtype, e.g. from the influenza virus A/Env/MPU3156/2005; an influenza virus comprising HA of the H5 subtype, e.g. from the influenza virus A/Eurasian Wigeon/MPF461/2007; an influenza virus comprising HA of the H9 subtype, e.g. from the influenza virus A/Hong Kong/1073/1999; an influenza virus comprising HA of the H3 subtype, e.g. from the influenza virus H/Hong Kong/1/1968 or A/Panama/2007/1999; an influenza virus comprising HA of the H14 subtype, e.g. from the influenza virus A/Mallard/Astrakhan/263/1982; an influenza virus comprising HA of the H7 subtype, e.g. from the influenza virus A/Mallard/Netherlands/12/2000; and an influenza virus comprising HA of the H10 subtype, e.g. from the influenza virus A/Chicken/Germany/N/1949. It will be understood by the skilled person that the polypeptides of the invention may also be derived from HA of other influenza A virus strains from either Group 1 or Group 2.

In certain preferred embodiments, depending on the HA subtype (i.e. group 1 or group 2) the HA polypeptides, or immunogenic fragments thereof, bind to the binding molecule CR9114, CR6261, CR8020 and/or MD3606. Thus, novel HA polypeptides are provided that display the specific epitopes of the antibody CR6261 (comprising a heavy chain variable region of SEQ ID NO: 2 and a light chain variable region of SEQ ID NO: 3) and/or the antibody CR9114 (comprising a heavy chain variable region of SEQ ID NO: 6 and a light chain variable region of SEQ ID NO: 7), and/or the antibody CR8020 (comprising a heavy chain variable region of SEQ ID NO: 4 and a light chain variable region of SEQ ID NO: 5) and/or the multidomain antibody MD3606 (SEQ ID NO: 8). The polypeptides of the invention can be used to elicit influenza virus neutralizing antibodies, when administered in vivo, either alone, or in combination with other prophylactic and/or therapeutic treatments.

In certain embodiments, the HA polypeptides of the invention, or immunogenic fragments thereof, are linked to nanoparticles, such as e.g. polymers, liposomes, virosomes, virus-like particles, or self-assembling nanoparticles. The polypeptides may be combined with, encapsidated in, or conjugated (e.g. covalently linked or adsorbed) to the nanoparticles.

The present invention further provides multimeric polypeptides comprising at least two HA polypeptides, or immunogenic fragments thereof, as described above.

In certain preferred embodiments, the multimeric polypeptides are trimeric and comprise three HA polypeptides, or immunogenic fragments thereof, as described above.

In certain embodiments, the present invention thus provides stabilized recombinant stabilized trimeric influenza A hemagglutinin (HA) polypeptides, or immunogenic fragments thereof, said polypeptides comprising three HA monomers, said HA monomers each comprising an HA1 and a HA2 domain of an influenza A virus HA, and comprising an amino acid sequence wherein:

(a) the amino acid at position 355 is W; and (b) the amino acid at position 432 is I, or the amino acid at position 432 is I and the amino acid at position 380 is I;

and wherein the numbering of the amino acid positions in the amino acid sequence of the HA polypeptide is according to the numbering of amino acids in the amino acid sequence of HA from a reference H3N2 influenza strain, in particular the reference strain H3N2 A/Aichi/2/68 (SEQ ID NO: 1).

As stated above, according to the invention it has been shown that both expression levels and trimerization of stable HA trimers can be increased, by having the amino acid residue W at position 355, e.g. by introducing a mutation of the amino acid at position 355 into W; in combination with the amino acid I at position 432, e.g. by introducing a mutation of the amino acid at position 432 into I; or having a combination of an I at position 432 and an I at position 380, e.g. by introducing a mutation at positions 432 and 380 into I. The polypeptides of the invention thus show an increased level of expression in mammalian cells, an increased propensity to trimerize (e.g. as measured by AlphaLISA, Octet, and SEC), and/or an increased level of thermo-stability (e.g. as measured by, Dynamic Scanning Fluorimetry/Calorimetry (DSF/DSC)), as compared to the HA polypeptides without these amino acid mutations.

In a particular embodiment, the HA polypeptides of the invention are stable for at least 3 days at 40° C.

The invention further provides nucleic acid molecules encoding the influenza HA polypeptides, or immunogenic fragments thereof, of the invention. It is understood by a skilled person that numerous different nucleic acid molecules can encode the same polypeptide as a result of the degeneracy of the genetic code. It is also understood that skilled persons may, using routine techniques, make nucleotide substitutions that do not affect the polypeptide sequence encoded by the polynucleotides described to reflect the codon usage of any particular host organism in which the polypeptides are to be expressed. Therefore, unless otherwise specified, a "nucleic acid molecule encoding an amino acid sequence" includes all nucleotide sequences that are degenerate versions of each other and that encode the same amino acid sequence.

In certain embodiments, the nucleic acid molecules encoding the influenza HA polypeptides, or immunogenic fragments thereof, are codon optimized for expression in mammalian cells, such as human cells. Methods of codon-optimization are known and have been described previously (e.g. WO 96/09378).

The present invention further provides methods for producing a recombinant HA polypeptide, or an immunogenic fragment thereof, as defined above, comprising expressing a nucleic acid molecule described above in prokaryotic (e.g. E. coli) or eukaryotic cells (e.g. a mammalian cells such as a CHO or PER.C6), said method optionally comprising the step of purifying/isolating the recombinant HA polypeptide, or immunogenic fragment thereof, from said cells. The recombinant influenza HA polypeptides, or immunogenic fragments thereof, can be prepared according to any technique deemed suitable to one of skill to produce recombinant polypeptides, including techniques as described herein. Thus, the polypeptides of the invention may be synthesized as DNA sequences by standard methods known in the art and cloned and subsequently expressed, in vitro or in vivo, using suitable restriction enzymes and methods known in the art. Nucleotide sequences encoding the HA polypeptides of the invention, or immunogenic fragments thereof, may be synthesized, and/or cloned and expressed according to techniques well known to those in the art. See for example, Sambrook, et al, Molecular Cloning, A Laboratory Manual, Vols. 1-3, Cold Spring Harbor Press, Cold Spring Harbor, N.Y. (1989). Use of recombinant DNA technology to produce influenza vaccines offers several advantages. This includes avoiding the steps of adaptation and passage of infectious viruses in eggs and production of more highly purified protein under safer and more stringently controlled conditions. Moreover, no virus inactivation step has to be included. Any suitable cloning and expression system may be used to recombinantly produce the HA polypeptides of the invention.

In preferred embodiments, the polypeptides, or immunogenic fragments thereof, are produced in mammalian cells. In certain embodiments, the polypeptides are glycosylated when expressed in suitable cells (e.g. mammalian cells). The polypeptides thus may contain one or more native and/or introduced (i.e. non-native) glycosylation motifs.

Hemagglutinin sequences may be produced by standard recombinant methods known in the art, such as polymerase chain reaction (PCR) or reverse transcriptase PCR, reverse engineering or the DNA can be synthesized. For PCR, primers can be prepared using hemagglutinin nucleotide sequences that are available in publicly available databases. Polynucleotide constructs may be assembled from PCR cassettes and sequentially cloned into a vector containing a selectable marker for propagation in a host cell. A recombinant vector can then be introduced into the host cell by injection, transfection or electroporation or other methods (for example, calcium phosphate transfection, DEAE-dextran mediated transfection, cationic lipid-mediated transfection, electroporation). Commercial transfection reagents such as Lipofectamine (Invitrogen, Carlsbad, Calif.) are also available.

The HA polypeptides, or immunogenic fragments thereof, can be recovered and isolated/purified from recombinant cell cultures by methods known in the art, including anion and/or cation exchange chromatography, affinity chromatography. Techniques such as SDS-PAGE can be used to analyze fractions of protein eluted from these separation/purification techniques. Such methods are well known to those skilled in the art and will not be presented in detail here. Purified polypeptides can also be analyzed by spectroscopic methods known in the art (e.g. circular dichroism spectroscopy, Fourier Transform Infrared spectroscopy and NMR spectroscopy or X-ray crystallography) to investigate the presence of desired structures like helices and beta sheets. ELISA, AlphaLISA, biolayer interferometry (Octet) and FACS and the like can be used to investigate binding of the polypeptides of the invention to the broadly neutralizing antibodies, such as CR6261 and/or CR9114. Thus, polypeptides according to the invention having the correct conformation can be selected. Trimeric content can be analyzed for example by using SDS gel electrophoresis under non-reducing conditions, size exclusion chromatography in the presence of antibody Fab fragments of broadly neutralizing antibodies, such as CR6261 and/or CR9114, as well as AlphaLISA using differently labeled antibodies. Stability of the polypeptides can be assessed as described above after temperature stress, freeze-thaw cycles, increased protein concentration, or agitation. The melting temperature of the polypeptide can further be assessed by Differential Scanning Fluorimetry (DSF).

In some embodiments the present invention provides recombinant influenza HA polypeptides that are derived from, comprise, or consist of any one of the influenza HA amino acid sequences selected from the group consisting of SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 33, SEQ ID NO: 34, SEQ ID NO: 35, SEQ ID NO: 36, SEQ ID NO: 38, SEQ ID NO: 40, SEQ ID NO: 42, SEQ ID NO: 44, SEQ ID NO: 47, SEQ ID NO: 50, SEQ ID NO: 51 and SEQ ID NO: 52 or any variants or fragments thereof, that have at least about 40% or 50% or 60% or 65% or 70% or 75% or 80% or 85% or 90% or 95% or 98% or 99% identity with such amino acid sequences, wherein the influenza HA polypeptides comprise a tryptophan (W) at position 355 and an isoleucine (I) at position 432 and/or 380, wherein the amino acid numbering is based upon the sequence of SEQ ID NO: 1, or at amino acid positions that correspond to such amino acid positions, for example as determined by alignment of an HA amino acid sequence to SEQ ID NO: 1

In certain embodiments the present invention provides recombinant influenza HA polypeptides that are derived from, comprise, or consist of the amino acid residues 18-518 of SEQ ID NO: 10, the amino acid residues 18-518 of SEQ ID NO: 12, the amino acid residues 16-514 of SEQ ID NO: 14, the amino acid residues 17-516 of SEQ ID NO: 16, the amino acid residues 19-512 of SEQ ID NO: 18, the amino acid residues 17-521 of SEQ ID NO: 20, the amino acid residues 17-521 of SEQ ID NO: 22, the amino acid residues 18-523 of SEQ ID NO: 24, the amino acid residues 19-515 of SEQ ID NO: 26, the amino acid residues 17-515 of SEQ ID NO: 28, the amino acid residues 17-521 of SEQ ID NO: 33, the amino acids 18-518 of SEQ ID NO: 34, the amino acids 18-518 of SEQ ID NO: 35, the amino acids 18-517 of SEQ ID NO: 36, the amino acids 18-518 of SEQ ID NO: 38, the amino acids 17-521 of SEQ ID NO: 40, the amino acids 17-521 of SEQ ID NO: 42, the amino acids 17-521 of SEQ ID NO: 44, the amino acids 17-519 of SEQ ID NO: 47, the amino acids 17-521 of SEQ ID NO: 50, the amino acids 19-515 of SEQ ID NO: 51, or the amino acids 17-514 of SEQ ID NO: 52.

In certain embodiments, the HA polypeptides comprise an amino acid sequence derived from, comprising, or consisting of SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 33, SEQ ID NO: 34 or SEQ ID NO: 35, SEQ ID NO: 36, SEQ ID NO: 38, SEQ ID NO: 40, SEQ ID NO: 42, SEQ ID NO: 44, SEQ ID NO: 47, SEQ ID NO: 50, SEQ ID NO: 51 and SEQ ID NO: 52.

The invention further relates to vectors comprising a nucleic acid molecule encoding a HA polypeptide of the invention, or an immunogenic fragment thereof.

In certain embodiments, the vector is a human recombinant adenovirus. The present invention thus also provides recombinant adenoviral vectors comprising a nucleic acid molecule encoding a HA polypeptide, or an immunogenic fragment thereof, according to the invention. The recombinant adenoviral vectors may encode membrane-bound HA, and thus encode HA polypeptides comprising an HA2 domain, comprising the transmembrane and cytoplasmic domains. The adenovector may also encode soluble polypeptides and thus encode HA polypeptides comprising a truncated HA2 domain.

The preparation of recombinant adenoviral vectors is well known in the art. The term 'recombinant' for an adenovirus, as used herein implicates that it has been modified by the hand of man, e.g. it has altered terminal ends actively cloned therein and/or it comprises a heterologous gene, i.e. it is not a naturally occurring wild type adenovirus. In certain embodiments, an adenoviral vector according to the invention is deficient in at least one essential gene function of the E1 region, e.g. the E1a region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

In certain embodiments, the adenovirus is a human adenovirus of the serotype 26.

The invention further provides immunogenic compositions comprising an HA polypeptide, an immunogenic fragment thereof, a nucleic acid, and/or a vector according to the invention, and pharmaceutically acceptable carrier. The invention in particular relates to pharmaceutical compositions comprising a therapeutically effective amount of the polypeptides, immunogenic fragments, nucleic acids, and/or vectors of the invention. The pharmaceutical compositions further comprise a pharmaceutically acceptable carrier. In the present context, the term "pharmaceutically acceptable" means that the carrier, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The term "carrier" refers to a diluent, excipient, or vehicle with which the polypeptides, nucleic acids, and/or vectors are administered. Saline solutions and aqueous dextrose and glycerol solutions can e.g. be employed as liquid carriers, particularly for injectable solutions.

The invention further relates to HA polypeptides, immunogenic fragments, nucleic acids, and/or vectors as described herein for use as a medicament. The invention relates in particular to HA polypeptides, nucleic acids, and/or vectors as described herein for use in inducing an immune response, preferably comprising eliciting neutralizing antibodies, against an influenza virus, in particular against the HA molecule of an influenza virus. In a preferred embodiment, the invention relates to HA polypeptides, immunogenic fragment, nucleic acids, and/or vectors as described herein for use as an influenza vaccine.

The invention also relates to methods for inducing an immune response, in particular methods for eliciting antibodies, against an influenza A virus in a subject in need thereof, the method comprising administering to said subject, an HA polypeptide, immunogenic fragment, nucleic acid molecule and/or vector as described above. A subject according to the invention preferably is a mammal that is capable of being infected with an influenza virus, or otherwise can benefit from the induction of an immune response against influenza virus, such subject for instance being a rodent, e.g. a mouse, a ferret, or a domestic or farm animal, or a non-human-primate, or a human. Preferably, the subject is a human subject, such as a person identified as being at risk of being infected with influenza disease In certain embodiments, the HA polypeptides, immunogenic fragments, nucleic acid molecules and/or vectors of the invention are administered in combination with an adjuvant. The adjuvant for may be administered before, concomitantly with, or after administration of the polypeptides, nucleic acid molecules and/or vectors of the invention. Examples of suitable adjuvants include aluminum salts such as aluminum hydroxide and/or aluminum phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, pertussis toxin PT, or tetanus toxoid TT, Matrix M, or combinations thereof. In addition, known immunopotentiating technologies may be used, such as fusing the polypeptides of the invention to proteins known in the art to enhance immune response (e.g. tetanus toxoid, CRM197, rCTB, bacterial flagellins or others) or including the polypeptides in virosomes, or combinations thereof. Also, genetic adjuvants may be used which are co-delivered or encoded by e.g. the same adenovector.

Administration of the HA polypeptides, immunogenic fragments, nucleic acid molecules, and/or vectors according to the invention can be performed using standard routes of administration. Non-limiting examples include parenteral administration, such as intravenous, intradermal, transdermal, intramuscular, subcutaneous, etc., or mucosal administration, e.g. intranasal, oral, and the like. The skilled person will be capable to determine the various possibilities to administer the polypeptides, nucleic acid molecules, and/or vectors according to the invention, in order to induce an immune response.

The invention further provides methods for preventing and/or treating, preferably preventing, an influenza virus disease in a subject in need thereof, comprising administering to said subject a therapeutically effective amount of an HA polypeptide, an immunogenic fragment, a nucleic acid molecule and/or a vector as described herein. A therapeutically effective amount refers to an amount of the polypeptide, immunogenic fragment, nucleic acid, and/or vector that is effective for preventing, ameliorating and/or treating a disease or condition resulting from infection by an influenza virus. Prevention encompasses inhibiting or reducing the spread of influenza virus or inhibiting or reducing the onset, development or progression of one or more of the symptoms associated with infection by an influenza virus. Amelioration as used herein may refer to the reduction of visible or perceptible disease symptoms, viremia, or any other measurable manifestation of influenza infection.

A subject in need of treatment includes subjects that are already inflicted with a condition resulting from infection with an influenza virus, as well as those in which infection with influenza virus is to be prevented. The polypeptides, immunogenic fragments, nucleic acids and/or vectors of the invention thus may be administered to a naive subject, i.e., a subject that does not have a disease caused by an influenza virus infection or has not been and is not currently infected with an influenza virus infection, or to subjects that already have been infected with an influenza virus.

In an embodiment, prevention and/or treatment may be targeted at patient groups that are susceptible to influenza virus infection. Such patient groups include, but are not limited to e.g., the elderly (e.g. ≥50 years old, ≥60 years old, and preferably ≥65 years old), the young (e.g. ≤5 years old, ≤1 year old), hospitalized patients, immunocompromised subjects, and patients who have been treated with an antiviral compound but have shown an inadequate antiviral response.

The polypeptides, immunogenic fragments, nucleic acid molecules and/or vectors of the invention may be administered to a subject in combination with one or more other active agents, such as alternative influenza vaccines, monoclonal antibodies, antiviral agents, antibacterial agents, and/or immunomodulatory agents. The one or more other active agents may be beneficial in the treatment and/or prevention of an influenza virus disease or may ameliorate a symptom or condition associated with an influenza virus disease. In some embodiments, the one or more other active agents are pain relievers, anti-fever medications, or therapies that alleviate or assist with breathing.

The HA polypeptides of the invention, or fragments thereof, may also be used as research tools, as diagnostic tools, or as targets for the production of antibody reagents or therapeutic antibodies. For example, in some embodiments the HA polypeptides may be useful as analytes for assaying and/or measuring binding of, and/or titers of, anti-HA antibodies, for example in ELISA assays, Biacore/SPR binding assays, and/or any other assays for antibody binding known in the art. As another example, the HA polypeptides of the invention could be used to analyze, and/or compare the efficacy of anti-HA antibodies.

The HA polypeptides of the invention, or fragments thereof, may also be useful for the generation of therapeutic antibodies and/or antibodies that can be used as research tools or for any other desired use. For example, the HA polypeptides of the invention can be used for immunization of non-human animals to obtain antibodies to the HA protein for use as research tools and/or as therapeutics. Such antibodies, which may be monoclonal or polyclonal, and/or cells that produce such antibodies, can then be obtained from the animal.

The polypeptides of the invention for use as a diagnostic tool may comprise a tag useful for any detection technique suitable for a given assay. The tag used will depend on the specific detection/analysis/diagnosis techniques and/or methods used. The methods may be carried in solution, or the polypeptide(s) of the invention may be bound or attached to a carrier or substrate, e.g., microtiter plates (ex: for ELISA), membranes and beads, etc.

The invention is further illustrated in the following examples and figures. The examples are not intended to limit the scope of the invention in any way.

EXAMPLES

Example 1: Soluble HA Polypeptides—Structure and Design Elements of Polypeptides of the Invention To produce soluble polypeptides representing the ectodomain of influenza A virus hemagglutinin (HA0), the HA needs to be expressed without its native transmembrane and cytoplasmic domain. Expression of stable trimeric soluble wild type (WT) HA is often very poor in mammalian cells. To improve at least the level of trimerization a Foldon trimerization domain is often genetically fused to the C-terminus of the polypeptide. Unfortunately, the addition of a Foldon domain introduces an unwanted neoepitope and often reduces the expression level or may alter the structure of the polypeptide. According to the present invention, it has been found that expression and trimerization levels of soluble stable HA trimers can be increased, without addition of a Foldon or any other non-natural trimerization sequences, by introducing specific amino acid mutations in the core of the HA polypeptide, in particular at the amino acid positions 355 and 432, or at the amino acid positions 355 and 380 and 432. It is noted that for the numbering of the amino acid positions in the HA monomers of the current invention the H3 numbering by Winter et al. 1981 is used (supra). Thus, the numbering of the amino acid positions in the HA polypeptide monomers of the invention is according to the numbering of the amino acid positions in HA from a reference H3N2 influenza strain, in particular the reference H3N2 strain A/Aichi/2/68 (having the amino acid sequence of SEQ ID NO: 1).

The main structural elements and positions of the key mutations according to the invention are shown in FIG. 1A in the HA of an influenza A H1 A/California/07/2009 strain (FIG. 1A). As shown, the HA monomer comprises a truncated HA2 domain (the HA2 domain in particular was truncated after amino acid position 514 (i.e. the C-terminal part of the HA2 domain was deleted starting from the amino acid at position 515) to delete the transmembrane and cytoplasmic domain and to yield the soluble ectodomain of HA (FIG. 1B).

The polypeptides of the invention may be made resistant to protease cleavage by a mutation of the natural monobasic cleavage site amino acid arginine (R) at position 329 (FIG. 1B) into, e.g. glutamine (Q). In contrast to the native full-length HA, polypeptides including the R329Q mutation cannot be cleaved by serine proteases (e.g. trypsin). Cleavage of HA enables the protein to undergo the conformational change required for membrane fusion and viral entry.

Example 2: Expression of Soluble Stabilized HA Compared to Wild Type HA in Different Subtypes In this Example, several HAs from influenza viruses from both Group 1 and Group 2 were selected and expressed as stabilized soluble trimeric HA polypeptides and compared to their respective wild type soluble HA ectodomains (i.e. without transmembrane and intracytoplasmic domains). According to the invention, a tryptophan (W) at position 355 and isoleucine's (I) at positions 380 and 432 were introduced in the amino acid sequences of the HA of five different Group 1 strains and five different Group 2 strains, including the eight most circulating subtypes in humans (FIG. 2A) if these amino acids were not yet present in the HA amino acid sequence. In addition, a methionine (M) was introduced at the top of the A-helix at position 388 in some polypeptides.

At position 478 an isoleucine was introduced or retained if already present in the WT sequences, except in the polypeptide derived from A/Mallard/Netherlands/12/200 (UFV181146) and A/Chicken/Germany/N/1949 (UFV181147). Expression levels and trimerization of the polypeptides of the invention in Expi293F culture supernatant were compared to the respective soluble WT polypeptides without the mutations of the invention.

Table 1 shows the polypeptides according to the invention that were prepared.

TABLE 1

| Polypeptide (SEQ ID NO) | 355W | 380I | 388M | 432I | 478I |
|---|---|---|---|---|---|
| UFV181009 (10) | + | + | + | + | + |
| UFV181091 (12) | + | + | + | + | + |
| UFV181154 (14) | + | + | + | + | + |
| UFV181159 (16) | + | + | + | + | + |
| UFV181156 (18) | + | + | + | + | + |
| UFV180660 (20) | + | + | | + | + |
| UFV181096 (22) | + | + | | + | + |
| UFV180661 (24) | + | + | + | + | |
| UFV180664 (26) | + | + | + | + | |
| UFV180662 (28) | + | + | + | + | |

+ means presence of said amino acid at said position;
empty cell means absence of said amino acid (i.e. presence of wild-type amino acid residue)

Figure 2:
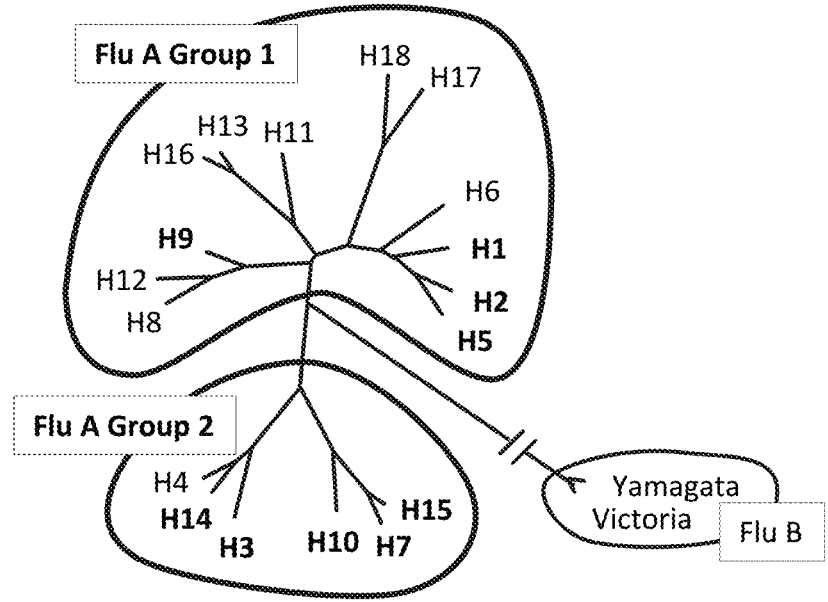
FIG. 2. A. Phylogenetic tree of influenza HA. Indicated are the different subtypes of Influenza A Group 1 and Group 2 and Influenza B; B. Protein expression levels as determined by OCTET (anti-His2 sensor). The last column shows the fold increase in expression level of the stabilized soluble HA trimers of the invention as compared to wildtype (WT) HA; C. Size exclusion chromatography (SEC) profiles—dotted lines represent WT HA, and the solid black line represents stabilized HA polypeptides according to the invention.
Figure 2:
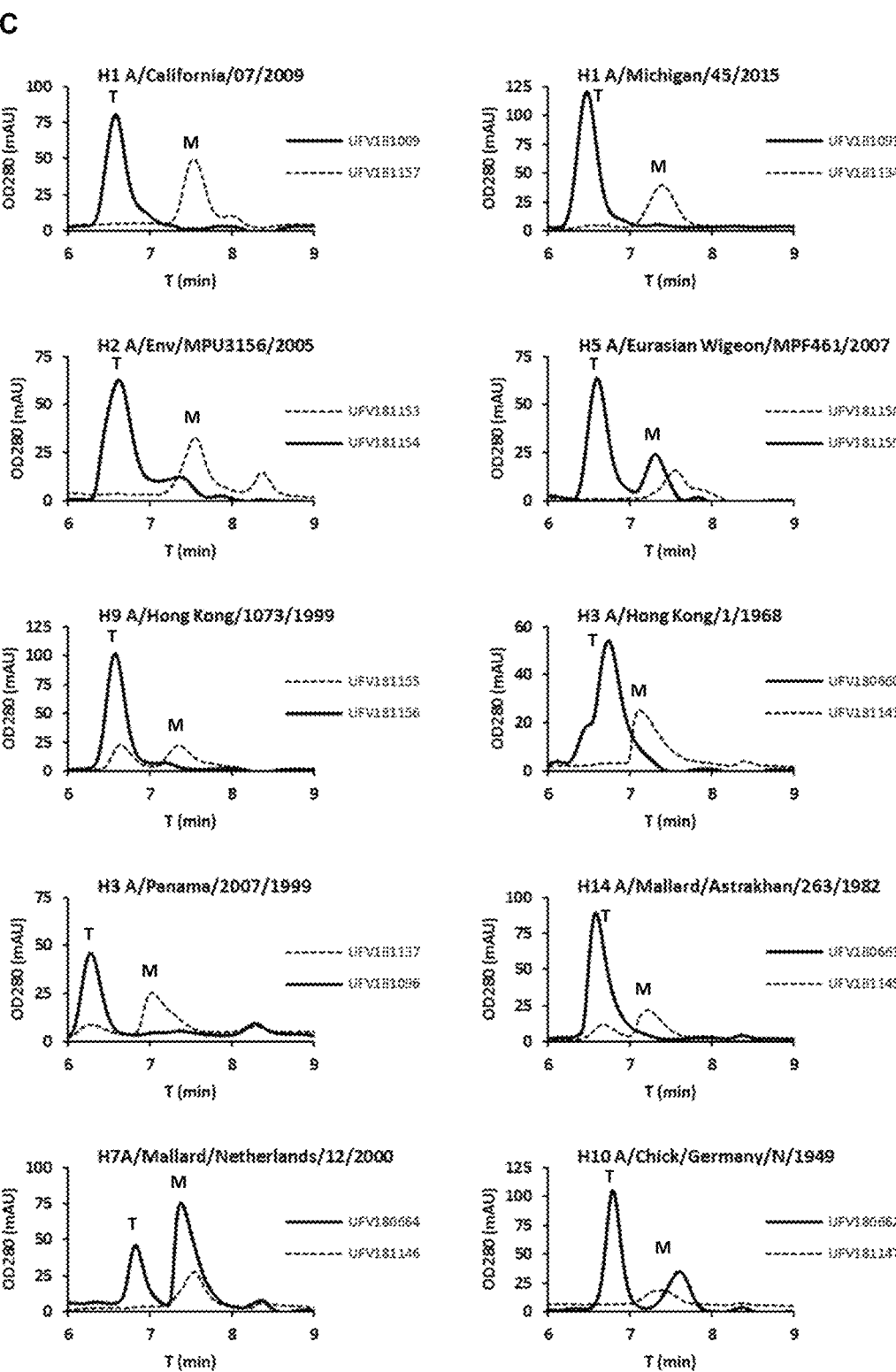

DNA fragments encoding the polypeptides listed in FIG. 2 and Table 1 were synthesized (Genscript) and cloned in the pcDNA2004 expression vector (modified pcDNA3 plasmid with an enhanced CMV promotor). The polypeptides of the invention included a C-terminal Linker-Sortase-Linker-His tag for site specific biotinylation, screening- and purification-purposes, and were produced in the eukaryotic Expi293F suspension cell line at micro scale (200 µL). The wild type (WT) full-length (FL) HA polypeptides contained a Linker-His tag for screening purposes.

The cells were transiently transfected with industrial grade DNA (≤0.01 EU/µg endotoxin level and ≥90% supercoil content) in 96-halfdeepwell plates (System Duetz) at a cell density of 2.5E+06 vc/mL using the ExpiFectamine 293 transfection kit (Gibco, ThermoFisher Scientific) and were incubated in shaker flasks containing Expi293 Expression Medium (Gibco, ThermoFisher Scientific) at 37° C., 250 rpm, 8% $CO_2$ and 75% humidity. Cell culture supernatants containing secreted polypeptides were harvested at day 3 and were clarified by centrifugation (10 min. at 400×g) followed by filtration (96-well Filter plates, 0.22 µm PVDF membrane, Corning).

The level of expressed soluble HA polypeptide in the harvested culture supernatant was assessed by Bio-Layer Interferometry using the OCTET platform (FortéBio). In short, a standard curve was established using anti-HIS (HIS2) biosensors (FortéBio) by measuring the binding shift of a dilution series of a well-defined reference batch of purified polypeptide UFV180436. Subsequently, the binding shifts of pre-diluted (in kinetics buffer, FortéBio) cell culture supernatants containing the polypeptides of the invention were measured and the concentration of the polypeptides was calculated using the established standard curve.

The presence of the expressed polypeptides and its quaternary structure (which indicates whether the polypeptide is a monomer, trimer or multimer) in the Expi293F cell culture harvests was assessed by analytical Size Exclusion Chromatography (SEC) in an Ultra High-Performance Liquid Chromatography (UHPLC) using a Vanquish system (ThermoFisher Scientific) with a BEH 200A column (Waters, injection volume 40 µL, flow 0.35 mL/min.). The elution was monitored by a Helios light scattering detector (Wyatt Technologies). The SEC profiles were analyzed by the Astra 6 software package (Wyatt Technology).

Results and Conclusion

Introduction of a tryptophan at position 355, and isoleucine's at positions 380 and/or 432 in the wild type HA of different strains resulted in an increase in expression for all the tested polypeptides of the invention as determined by OCTET (FIG. 2B).

SEC analysis of crude cell culture supernatants showed that upon introduction of the stabilizing mutations in the polypeptides of the invention, for all soluble stabilized HAs a distinct trimer (T) peak appears at a retention time between 6 and 7 minutes which is higher than the trimer peaks observed for the respective wild type HA ectodomains (FIG. 2C). It is noted that the differences in retention time between different influenza HA subtypes are likely due to differences in the level and complexity of glycosylation.

Taken together, the data confirm that introduction of mutations 355W, 380I and/or 432I in the HA polypeptides of the invention results in increased expression and formation of stable soluble trimeric HA.

Example 3: In Vitro Characterization of Purified Trimeric Full-Length HA Compared to Wild Type HA Containing a Foldon Trimerization Domain To further characterize the contribution of the critical stabilizing mutations 355W, 380I and/or 432I, the mutations were introduced in HA ectodomain polypeptides (i.e. excluding TM and IC domains) derived from the H1 strains A/California/07/2009 (UFV181009), A/Michigan/45/2015 ((UFV181091), and the H3 strains A/Hong Kong/1/1968 (UFV180660) and A/Indiana/11/2011 (UFV181099) and compared to the wild type (WT) HA ectodomains containing a Foldon trimerization domain (with an exception for UFV4239 (SEQ ID NO: 29) that lacked the Foldon trimerization domain). The polypeptides comprised the amino acids as shown in Table 2. All polypeptides further contained a His tag for purification and screening purposes and were produced in ExpiCHO cells after which they were purified and characterized.

DNA fragments encoding the polypeptides of the invention were synthesized as described in Example 2. The polypeptides were produced in ExpiCHO suspension cells (350 mL scale) and cultured in ExpiCHO expression medium by transient transfection respective industrial grade DNA using ExpiFectamine transfection reagent (Gibco, ThermoFisher Scientific) according to the manufacturer's protocol. ExpiFectamine CHO Enhancer and ExpiCHO Feed (Gibco, ThermoFisher Scientific) were added to the cell cultures 1-day post transfection according to the manufacturer's protocol. ExpiCHO transfected cell suspensions were incubated at 32° C., 5% CO2 and the culture supernatants containing the secreted polypeptides were harvested between day 7-11. The culture supernatants were clarified by centrifugation, followed by filtration over a 0.2 μm bottle top filter (Corning).

From the harvested culture supernatants, the his-tagged polypeptides of the invention and respective wild type strains containing a Foldon trimerization domain were purified following a two-step protocol using an ÄKTA Avant 25 system (GE Healthcare Life Sciences). First, immobilized metal affinity chromatography was performed using a pre-packed cOmplete His-tag Purification Column (Roche), washed with 1 mM Imidazole and eluted with 300 mM Imidazole. Secondly, Size Exclusion Chromatography using a HiLoad Superdex 200 pg 26/600 Column (GE Healthcare Life Sciences) was performed. Trimer peak fractions were pooled and frozen and stored (1 and 6 months) at −80° C.

The trimer content of the purified polypeptides of the invention was assessed by analytical SEC in an Ultra High-Performance Liquid Chromatography (UHPLC) as described in Example 2. Of each purified polypeptide 20 μg was injected and run over the column.

Thermo-stability of the purified polypeptides was determined by Differential Scanning Fluorimetry (DSF) by monitoring the fluorescent emission of Sypro Orange Dye (ThermoFisher Scientific) added to a 6 μg polypeptide solution. Upon gradual increase of the temperature, from 25° C. to 95° C. (60° C. per hour), the polypeptides unfold and the fluorescent dye binds to the exposed hydrophobic residues leading to a characteristic change in emission. The melting curves were measured using a ViiA7 real time PCR machine (Applied BioSystems) and the $Tm_{50}$ values were calculated by the Spotfire suite (Tibco Software Inc.). The $Tm_{50}$ values represent the temperature at which 50% of the protein is unfolded and thus are a measure for the temperature stability of the polypeptides.

The three-dimensional conformation of the purified polypeptides was assessed by testing the antigenicity in ELISA ($EC_{50}$ values of the antibody binding). To this end, polypeptides were coated at a concentration of 10 nM and incubated with a dilution series of monoclonal antibodies (mAbs): in particular CR6261 (Group 1 specific), CR8020 (Group 2 specific), CR9114 (Both Group 1 and 2 specific), and MD3606 (Group 1 and 2 specific multidomain antibody), using 70 nM as starting concentration. Antibody binding was determined by incubation with a secondary antibody anti-human Fc HRP (Mouse anti Human IgG, Jackson ImmunoResearch) and visualized by addition of POD substrate. Read out was performed using the EnSight™ multimode plate reader (PerkinElmer). The $EC_{50}$ values of two independent experiments were calculated using the Spotfire suite (Tibco Software Inc.) and the average and standard deviation listed in FIG. 3D.

Results and Conclusion

TABLE 2

| Polypeptides of the invention | | | | | |
|---|---|---|---|---|---|
| Polypeptides (SEQ ID NO) | 355W | 380I | 388M | 432I | 478I |
| UFV181009 (10) | + | + | | + | + |
| UFV181091 (12) | + | + | | + | + |
| UFV180660 (20) | + | + | + | + | |
| UFV181099 (33) | + | + | | + | |

Figure 3:
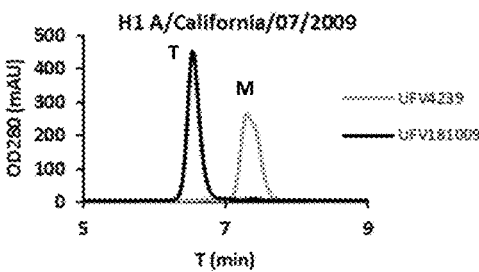
FIG. 3. A. SEC analysis of purified trimeric (T) polypeptides of the invention (black line) and the WT polypeptides with Foldon trimerization domain (gray line) (it is noted that UFV4239 does not comprise a Foldon domain). The WT-Foldon purified polypeptides show peak broadening and multimer formation (*) after storage at −80° C. Due to the missing trimerization domain in UFV4239, only monomer (M) was expressed and purified; B and C. Temperature stability analysis of purified polypeptides by Differential Scanning Fluorimetry (DSF, $Tm_{50}$ values in ° C.); D. Binding of monoclonal antibodies (mAbs) CR6261, CR8020, CT149, CR9114, and the multidomain antibody MD3606 (ELISA, $EC_{50}$ values).
Figure 3:
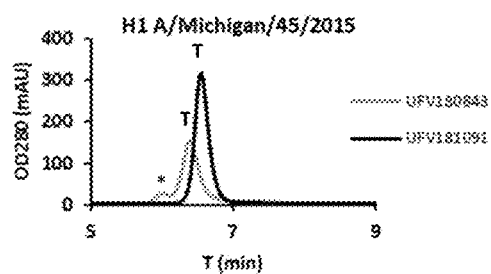
Figure 3:
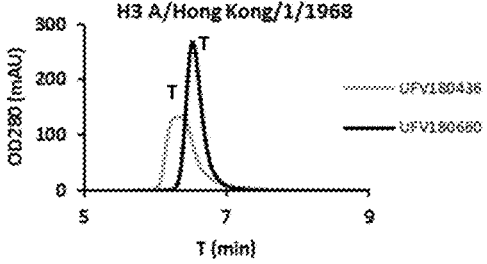
Figure 3:
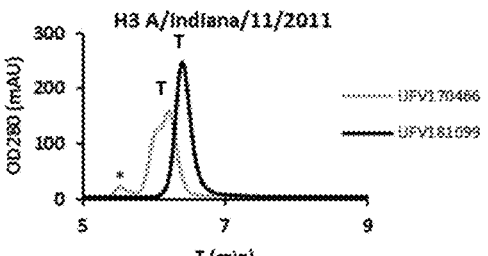
Figure 3:
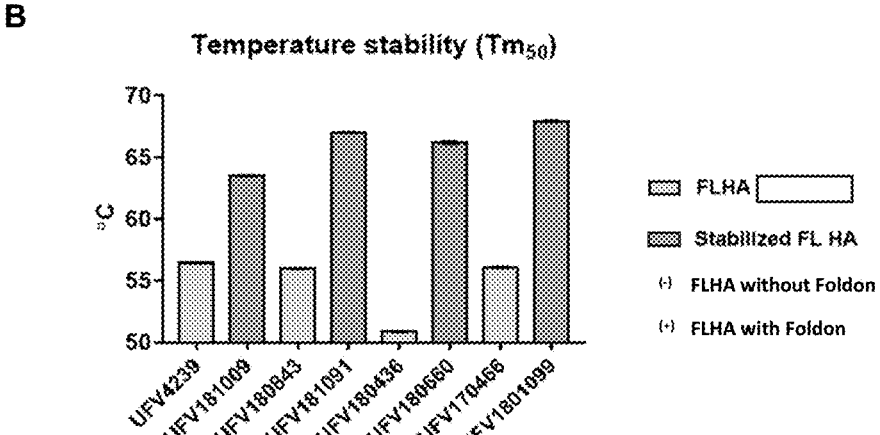

SEC analysis results confirmed that the presence (or simultaneous introduction of the stabilizing) amino acids into the polypeptides of the invention of different influenza HA strains enables purification of highly pure and stable soluble trimeric HA polypeptides. The stabilizing effect of the amino acids were observed best for the purified polypeptide derived from H1 A/California/07/2009 (UFV181009) where the corresponding wild type construct (UFV4239, SEQ ID NO: 29) did not possess a Foldon trimerization domain and only produced a monomer peak while the stabilized polypeptide of the invention shows a highly pure trimer peak (FIG. 3A). The wild type HA molecules of the other H1 strain A/Michigan/45/2015, and the H3 strains A/Hong Kong/1/1968 and A/Indiana/11/2011 were expressed with an additional C-terminal Foldon domain and did form trimeric HA. However, unlike their respective stabilized polypeptides of the invention, the trimeric peaks of wild type HA with Foldon domain were broader, asymmetrical, and showed shoulders suggesting the presence of alternative high- and/or low-molecular weight polypeptides in undesired conformation (*) or a less compact folding (Seok et al., Sci. Rep. 8; 7(1)-7540, 2017).

Further characterization of all polypeptides showed that the polypeptides of the invention including the stabilizing amino acids display a significant higher thermal stability compared to the WT polypeptides with or without (UFV4239, SEQ ID NO: 29) Foldon trimerization domain (FIGS. 3B and 3C).

The introduced stabilizing mutations are buried mutations (i.e. they are inside the HA polypeptide and not at the surface) and thus should not affect the surface of the monomeric or trimeric HA. To confirm the integrity of the HA surface, binding of a panel of well-known broadly neutralizing antibodies to the polypeptides was assessed by ELISA. The wild type and stabilized polypeptides of the invention showed comparable binding with $EC_{50}$ values in the low nM range to all antibodies according to their expected breadth of binding. An improvement (~4-8 fold) for CR9114 binding to H3 A/Hong Kong/1/1968 and H3 A/Indiana/11/2011 derived HA polypeptides of the invention was observed (FIG. 3D).

In conclusion, the polypeptides of the invention described in this example were purified from the cell culture supernatant as highly pure trimeric polypeptides and showed improved thermal stability compared to the WT HA (with or without Foldon trimerization domain) and were properly folded.

Example 4: Characterization of Combinations of Stabilizing Mutations

Figure 4:
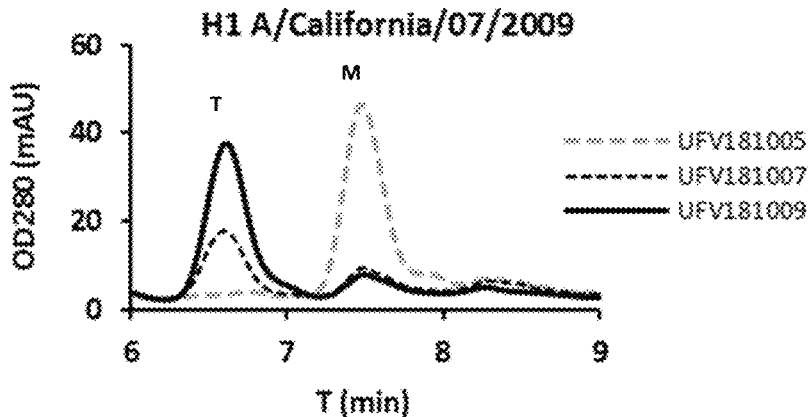
FIG. 4. A. Protein expression levels as determined by OCTET (anti-His2 sensor); B. SEC analysis of EXPI-293 cell culture supernatants. UFV181007 comprises mutations K380I and E432I (dotted black line). UFV181005 comprises mutations H355W and M478I (dotted grey line). Combination of the stabilizing mutations (UFV1810009, black line).

To assess the beneficial effect of combining the stabilizing mutations in polypeptides of the invention, combination 355W+478I, and combination 380I+432I were stepwise introduced in the HA ectodomain of H1 strain A/California/07/2009 (FIG. 4A, a '.' indicates the unchanged presence of the H1 wild type (WT) residue as listed in the first line).

DNA fragments encoding the polypeptides of the invention were synthesized as described in Example 2. The polypeptides, including a C-terminal Linker-Sortase-Linker-His tag for site-specific biotinylation, and screening- and purification-purposes, were produced in eukaryotic Expi293F cells at micro scale (200 μL) as described in Example 2. The level of expressed polypeptide was determined by OCTET and the trimer content was analyzed by analytical SEC as described in Example 2.

Results and Conclusion

Assessment of the expression levels of the polypeptides of the invention with different combinations of the stabilizing mutations revealed that mutations 380I and 432I, as present in UFV181007 (SEQ ID NO: 35), did not affect the expression but compared to the WT construct, significantly increased the level of trimers (FIG. 4B). Adding the mutations 355W and 478I (e.g. UFV181005: SEQ ID NO: 34) resulted in a notable increase in expression (FIG. 4A) but no formation of trimers was observed (FIG. 4B). When combining 355W, 478I, 380I and 432I (e.g. in UFV181009: SEQ ID NO: 10) both the level of expression was increased (FIG. 4A) and the trimer content was significantly improved in the cell culture supernatant (FIG. 4B).

In conclusion, the mutations 355W and 478I increased the expression levels of the polypeptides of the invention, while mutation 380I and 432I improved the trimer formation. The combination of the stabilizing mutations synergistically increased expression and trimer levels of the polypeptides of the invention.

Figure 5:
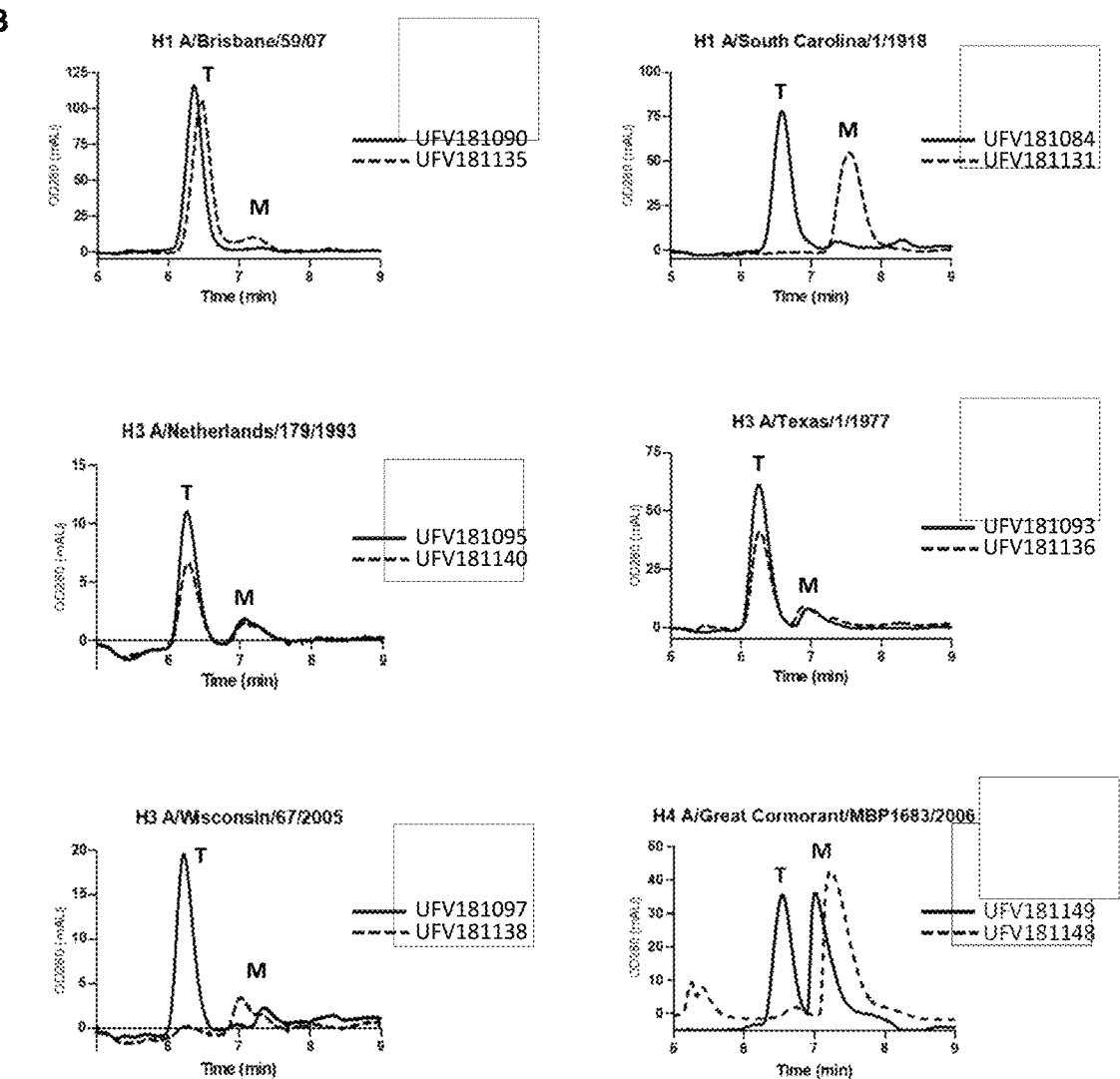
FIG. 5. A. Protein expression levels as determined by OCTET (anti-His2 sensor). The last column shows the fold increase in expression level of the stabilized soluble HA trimers of the invention as compared to wildtype (WT) HA; B. Size exclusion chromatography (SEC) profiles—dotted lines represent WT HA, and the solid black lines represents the additional stabilized HA polypeptides according to the invention.

Example 5: Expression of Additional Soluble Stabilized HA Compared to Wild Type HA in Various HA Subtypes In this example, further additional stabilized HAs were expressed and compared to their respective wild type soluble HA ectodomains (FIG. 5A). A tryptophan (W) at position 355 and isoleucine's (I) at positions 380 and 432 were introduced in the amino acid sequences of the HA of two additional Group 1 strains and four additional Group 2 strains. Expression levels and trimerization of the polypeptides in Expi293F culture supernatants, three days after transfection, were compared to the respective soluble WT polypeptides without the mutations of the invention. Table 4 shows the additional polypeptides according to the invention that were prepared.

DNA fragments encoding the polypeptides of the invention were synthesized as described in example 2. The plasmids were transfected in eukaryotic Expi293F cells at micro scale (200 μL) as described in Example 2. All polypeptides were expressed including a C-terminal linker His-tag for screening- and purification-purposes whereas the stabilized polypeptides include an additional Sortase-Linker sequence preceding the His tag for site-specific biotinylation. The level of expressed polypeptide was determined by OCTET and the trimer content was analyzed by analytical SEC as described in Example 2.\

Results and Conclusion

Like observed in example 2, introduction of a tryptophan at position 355, and isoleucine's at positions 380 and 432 in the wild type HA of different strains resulted in an increase in expression of all these additionally tested polypeptides based on OCTET measurements. One exception was seen for the H1 A/South Carolina/1/1918 (UFV181084) derived HA that showed a small decrease as determined by OCTET (FIG. 5A) but not based on area under the curve in SEC (FIG. 5B).

SEC analysis of crude cell culture supernatant showed that upon introduction of the stabilizing mutations in all additional soluble stabilized HAs more trimeric polypeptide (T) and less monomeric polypeptide (M) and high molecular weight species were observed compared to the respective wild type HA ectodomains (FIG. 5B). Like noted in Example 2, the differences in retention time between different influenza HA subtypes are likely due to differences in the level and complexity of glycosylation.

Taken together, the data confirm that introduction of mutations 355W, 380I and/or 432I in the additional HA polypeptides of the invention results in increased expression and formation of stable soluble trimeric HA.

Example 6: In Vitro Characterization of Purified Trimeric Full-Length HA (Additional Data)

In this example, additional stabilized HAs were expressed, purified, and exposed to long term temperature stress. These HAs, UFV190839 (SEQ ID NO: 50), UFV190068 (SEQ ID NO: 51) and UFV190841 (SEQ ID NO: 52). were derived from respectively H3 A/Hong Kong/1/1968 H7 A/Mallard/NL/12/2000, and H10 A/Chick/Germany/N/1949. In short, purified trimeric polypeptide was stored for 60 days at 4° C. (fridge) and 37° C. (incubator) following which protein integrity was evaluated by analytical SEC.

According to the invention, a tryptophan (W) at position 355 and isoleucine's (I) at positions 380 and 432 were introduced in the amino acid sequences of the HA of three different Group 2 strains.

DNA fragments encoding the polypeptides of the invention were synthesized as described in Example 2. The polypeptides were produced in eukaryotic ExpiCHO cells at medium scale (30 mL) as described in Example 3 and harvested at day 5. All polypeptides were expressed including a C-terminal Linker-Sortase-Linker His-tag for site-specific biotinylation, screening- and purification-purposes. The proteins were purified by the two-step process as described in Example 3, however, now a HiLoad Superdex 200 16/600 column was used (GE Healthcare Life Sciences). The level of expressed polypeptide was determined by OCTET and the trimer content was analyzed by analytical SEC as described in Example 2 with the deviation that now a Unix-C 300 A column (Sepax Technologies) was used.

Results and Conclusion

Figure 6:
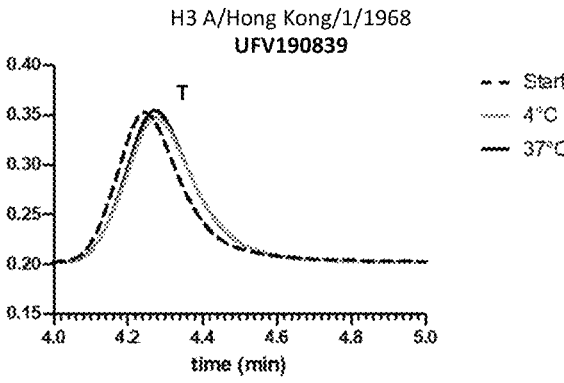
FIG. 6. Size exclusion chromatography (SEC) profiles of purified stabilized HA before and after temperature stress. Shown are the profiles for the polypeptides prior to the experiment (dotted lines) and following a 60-day incubation at 4° C. (solid black lines) and 37° C. (solid grey lines).
Figure 6:
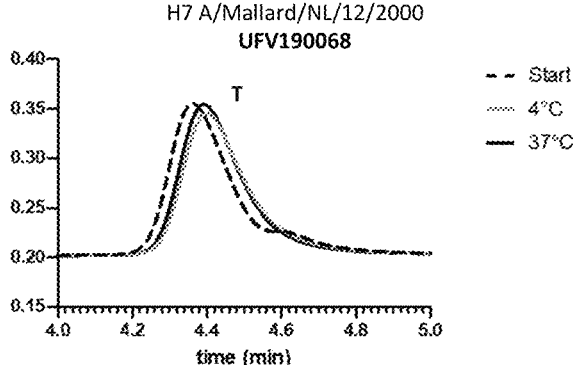
Figure 6:
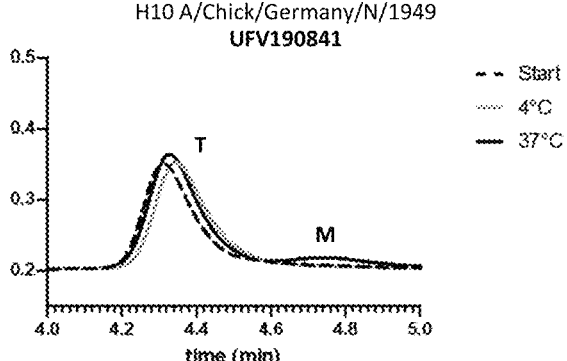

SEC analysis results indicated that the polypeptides of the invention including the stabilizing amino acids obtained following purification were highly pure and trimeric. Furthermore, the soluble HA polypeptides were resistant to temperature stress; a 60-day incubation at 4° C. and 37° C. did not affect the amount of protein and trimeric state compared to observed for the material before stress (FIG. 6) and only a small amount of other than trimeric polypeptide was observed (~4.75 minute retention time) for the H10 derived HA following incubation at 37° C.

Like noted in Example 2, the differences in retention time between different influenza HA subtypes are likely due to differences in the level and complexity of glycosylation. Furthermore, the small differences in retention time observed for the starting material compared to the material stressed for 60 days are likely due to column aging (i.e. similar shift was observed for the internal control).

In conclusion, the polypeptides of the invention described in this example were purified from culture supernatant as highly pure trimeric polypeptides and showed to be highly inert to temperature stress for a period of 60 days.

TABLE 3

Standard amino acids, abbreviations and properties

| Amino Acid | 3-Letter | 1-Letter | Side chain polarity | Side chain charge (pH 7.4) |
|---|---|---|---|---|
| alanine | Ala | A | nonpolar | Neutral |
| arginine | Arg | R | polar | Positive |
| asparagine | Asn | N | polar | Neutral |
| aspartic acid | Asp | D | polar | Negative |
| cysteine | Cys | C | nonpolar | Neutral |
| glutamic acid | Glu | E | polar | Negative |
| glutamine | Gln | Q | polar | Neutral |
| glycine | Gly | G | nonpolar | Neutral |
| histidine | His | H | polar | positive (10%) neutral (90%) |
| isoleucine | Ile | I | nonpolar | Neutral |

TABLE 3-continued

Standard amino acids, abbreviations and properties

| Amino Acid | 3-Letter | 1-Letter | Side chain polarity | Side chain charge (pH 7.4) |
|---|---|---|---|---|
| leucine | Leu | L | nonpolar | Neutral |
| lysine | Lys | K | polar | Positive |
| methionine | Met | M | nonpolar | Neutral |
| phenylalanine | Phe | F | nonpolar | Neutral |
| proline | Pro | P | nonpolar | Neutral |
| serine | Ser | S | polar | Neutral |
| threonine | Thr | T | polar | Neutral |
| tryptophan | Trp | W | nonpolar | Neutral |
| tyrosine | Tyr | Y | polar | Neutral |
| valine | Val | V | nonpolar | Neutral |

```
SEQUENCES
SEQ ID NO: 1 CAA24269.1 haemagglutinin (Influenza A virus
(A/Aichi/2/1968(H3N2) (excluding signal sequence)
QDLPGNDNST ATLCLGHHAV PNGTLVKTIT DDQIEVTNAT ELVQSSSTGK        50

ICNNPHRILD GIDCTLIDAL LGDPHCDVFQ NETWDLFVER SKAFSNCYPY       100

DVPDYASLRS LVASSGTLEF ITEGFTWTGV TQNGGSNACK RGPGSGFFSR       150

LNWLTKSGST YPVLNVTMPN NDNFDKLYIW GIHHPSTNQE QTSLYVQASG       200

RVTVSTRRSQ QTIIPNIGSR PWVRGLSSRI SIYWTIVKPG DVLVINSNGN       250

LIAPRGYFKM RTGKSSIMRS DAPIDTCISE CITPNGSIPN DKPFQNVNKI       300

TYGACPKYVK QNTLKLATGM RNVPEKQTRG LFGAIAGFIE NGWEGMIDGW       350

YGFRHQNSEG TGQAADLKST QAAIDQINGK LNRVIEKTNE KFHQIEKEFS       400

EVEGRIQDLE KYVEDTKIDL WSYNAELLVA LENQHTIDLT DSEMNKLFEK       450

TRRQLRENAE EMGNGCFKIY HKCDNACIES IRNGTYDHDV YRDEALNNRF       500

QIKGVELKSG YKDWILWISF AISCFLLCVV LLGFIMWACQ RGNIRCNICI       550

CR6261 VH PROTEIN (SEQ ID NO: 2)
EVQLVESGAEVKKPGSSVKVSCKASGGPFRSYAISWVRQAPGQGPEWMGGIIPIFGTTKYAP

KFQGRVTITADDFAGTVYMELSSLRSEDTAMYYCAKHMGYQVRETMDVWGKGTTVTVSS

CR6261 VL PROTEIN (SEQ ID NO: 3)
QSVLTQPPSVSAAPGQKVTISCSGSSSNIGNDYVSWYQQLPGTAPKLLIYDNNKRPSGIPDR

FSGSKSGTSATLGITGLQTGDEANYYCATWDRRPTAYVVFGGGTKLTVL

CR8020 VH PROTEIN (SEQ ID NO: 4)
QVQLQQSGAEVKTPGASVKVSCKASGYTFTSFGVSWIRQAPGQGLEWIGWISAYNGDTYYAQ

KFQARVTMTTDTSTTTAYMEMRSLRSDDTAVYYCAREPPLFYSSWSLDNWGQGTLVTVSS

CR8020 VL PROTEIN (SEQ ID NO: 5)
EIVLTQSPGTLSLSPGERATLSCRASQSVSMNYLAWFQQKPGQAPRLLIYGASRRATGIPDR

ISGSGSGTDFTLTISRLEPADFAVYYCQQYGTSPRTFGQGAKVEIK

CR9114 VH PROTEIN (SEQ ID NO: 6)
QVQLVQSGAEVKKPGSSVKVSCKSSGGTSNNYAISWVRQAPGQGLDWMGGISPIFGSTAYAQ

KFQGRVTISADIFSNTAYMELNSLTSEDTAVYFCARHGNYYYYSGMDVWGQGTTVTVSS

CR9114 VL PROTEIN (SEQ ID NO: 7)
SYVLTQPPAVSGTPGQRVTISCSGSDSNIGRRSVNWYQQFPGTAPKLLIYSNDQRPSVVPDR

FSGSKSGTSASLAISGLQSEDEAEYYCAAWDDSLKGAVFGGGTQLTVL

MD3606 PROTEIN (SEQ ID NO: 8)
EVQLVESGGGLVQPGGSLRLSCAVSISIFDIYAMDWYRQAPGKQRDLVATSFRDGSTNYADS

VKGRFTISRDNAKNTLYLQMNSLKPEDTAVYLCHVSLYRDPLGVAGGMGVYWGKGALVTVSS
```

-continued

GGGGSGGGGSEVQLVESGGGLVQAGGSLKLSCAASGRTYAMGWFRQAPGKEREFVAHINALG

TRTYYSDSVKGRFTISRDNAKNTEYLEMNNLKPEDTAVYYCTAQGQWRAAPVAVAAEYEFWG

QGTQVTVSSGGGGSGGGGSEVQLVESGGGLVQPGGSLRLSCAATGFTLENKAIGWFRQTPGS

EREGVLCISKSGSWTYYTDSMRGRFTISRDNAENTVYLQMDSLKPEDTAVYYCATTTAGGGL

CWDGTTFSRLASSWGQGTQVTVSSGGGGSGGGGSEVQLVESGGGLVQPGGSLKLSCAASGFT

FSTSWMYWLRQAPGKGLEWVSVINTDGGTYYADSVKDRFTISRDNAKDTLYLQMSSLKSEDT

AVYYCAKDWGGPEPTRGQGTQVTVSSDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLS

LSPGK

SEQ ID NO 9: UFV181157 (Signal peptide and tag underlined)
MKAILVVLLYTFATANADTLCIGYHANNSTDTVDTVLEKNVTVTHSVNLLEDKHNGKLCKLR

GVAPLHLGKCNIAGWILGNPECESLSTASSWSYIVETPSSDNGTCYPGDFIDYEELREQLSS

VSSFERFEIFPKTSSWPNHDSNKGVTAACPHAGAKSFYKNLIWLVKKGNSYPKLSKSYINDK

GKEVLVLWGIHHPSTSADQQSLYQNADAYVFVGSSRYSKKFKPEIAIRPKVRDQEGRMNYYW

TLVEPGDKITFEATGNLVVPRYAFAMERNAGSGIIISDTPVHDCNTTCQTPKGAINTSLPFQ

NIHPITIGKCPKYVKSTKLRLATGLRNIPSIQSRGLFGAIAGFIEGGWTGMVDGWYGYHHQN

EQGSGYAADLKSTQNAIDEITNKVNSVIEKMNTQFTAVGKEFNHLEKRIENLNKKVDDGFLD

IWTYNAELLVLLENERTLDYHDSNVKNLYEKVRSQLKNNAKEIGNGCFEFYHKCDNTCMESV

KNGTYDYPKYSEEAKLNREEIDGSHHHHHH

SEQ ID NO 10: UFV181009 (Signal peptide and tag underlined)
MKAILVVLLYTFATANADTLCIGYHANNSTDTVDTVLEKNVTVTHSVNLLEDKHNGKLCKLR

GVAPLHLGKCNIAGWILGNPECESLSTASSWSYIVETPSSDNGTCYPGDFIDYEELREQLSS

VSSFERFEIFPKTSSWPNHDSNKGVTAACPHAGAKSFYKNLIWLVKKGNSYPKLSKSYINDK

GKEVLVLWGIHHPSTSADQQSLYQNADAYVFVGSSRYSKKFKPEIAIRPKVRDQEGRMNYYW

TLVEPGDKITFEATGNLVVPRYAFAMERNAGSGIIISDTPVHDCNTTCQTPKGAINTSLPFQ

NIHPITIGKCPKYVKSTKLRLATGLRNIPSIQSRGLFGAIAGFIEGGWTGMVDGWYGYHWQN

EQGSGYAADLKSTQNAIDEITNIVNSVIEKMNTQFTAVGKEFNHLEKRIENLNKKVDDGFLD

IWTYNAELLVLLINERTLDYHDSNVKNLYEKVRSQLKNNAKEIGNGCFEFYHKCDNTCIESV

KNGTYDYPKYSEEAKLNREEIDSGSLPETGGGSHHHHHH

SEQ ID NO 11: UFV181134 (Signal peptide and tag underlined)
MKAILVVLLYTFTTANADTLCIGYHANNSTDTVDTVLEKNVTVTHSVNLLEDKHNGKLCKLR

GVAPLHLGKCNIAGWILGNPECESLSTASSWSYIVETSNSDNGTCYPGDFINYEELREQLSS

VSSFERFEIFPKTSSWPNHDSNKGVTAACPHAGAKSFYKNLIWLVKKGNSYPKLNQSYINDK

GKEVLVLWGIHHPSTTADQQSLYQNADAYVFVGTSRYSKKFKPEIATRPKVRDQEGRMNYYW

TLVEPGDKITFEATGNLVVPRYAFTMERNAGSGIIISDTPVHDCNTTCQTPEGAINTSLPFQ

NIHPITIGKCPKYVKSTKLRLATGLRNVPSIQSRGLFGAIAGFIEGGWTGMVDGWYGYHHQN

EQGSGYAADLKSTQNAIDKITNKVNSVIEKMNTQFTAVGKEFNHLEKRIENLNKKVDDGFLD

IWTYNAELLVLLENERTLDYHDSNVKNLYEKVRNQLKNNAKEIGNGCFEFYHKCDNTCMESV

KNGTYDYPKYSEEAKLNREKIDGSHHHHHH

-continued

SEQ ID NO 12: UFV181091 (Signal peptide and tag underlined)
MKAILVVLLYTFTTANADTLCIGYHANNSTDTVDTVLEKNVTVTHSVNLLEDKHNGKLCKLR

GVAPLHLGKCNIAGWILGNPECESLSTASSWSYIVETSNSDNGTCYPGDFINYEELREQLSS

VSSFERFEIFPKTSSWPNHDSNKGVTAACPHAGAKSFYKNLIWLVKKGNSYPKLNQSYINDK

GKEVLVLWGIHHPSTTADQQSLYQNADAYVFVGTSRYSKKFKPEIATRPKVRDQEGRMNYYW

TLVEPGDKITFEATGNLVVPRYAFTMERNAGSGIIISDTPVHDCNTTCQTPEGAINTSLPFQ

NIHPITIGKCPKYVKSTKLRLATGLRNVPSIQSRGLFGAIAGFIEGGWTGMVDGWYGYHWQN

EQGSGYAADLKSTQNAIDKITNIVNSVIEKMNTQFTAVGKEFNHLEKRIENLNKKVDDGFLD

IWTYNAELLVLLINERTLDYHDSNVKNLYEKVRNQLKNNAKEIGNGCFEFYHKCDNTCIESV

KNGTYDYPKYSEEAKLNREKIDSGSLPETGGGSHHHHHH

SEQ ID NO 13: UFV181153 (Signal peptide and tag underlined)
MAIIYLILLFAAVRGDQICIGYHSNNSTEKVDTILERNVTVTHAQDILEKTHNGKLCKLNGI

PPLELGDCSIAGWLLGNPECDRLLTVPEWSYIMEKENPRNGLCYPGSFNDYEELKHLLSSVT

HFEKVKILPRDRWTQHTTTGGSRACAVSGNPSFFRNMVWLTKKGSNYPIAKGSYNNTSGEQM

LIIWGVHHPNDDAEQRTLYQNVGTYVSVGTSTLNKRSVPEIATRPKVNGQGGRMEFSWTILD

MLDTINFESTGNLIAPEYGFRISKRGSSGIMKTEGTLENCETKCQTPLGAINTTLPFHNIHP

LTIGECPKYVKSERLVLATGLRNVPQIESRGLFGAIAGFIEGGWQGMVDGWYGYHHSNDQGS

GYAADKESTQRAIDGITNKVNSVIEKMNTQFEAVGKEFNNLEKRLENLNKKMEDGFLDVWTY

NAELLVLMENERTLDFHDSNVKNLYDKVRMQLRDNAKELGNGCFEFYHKCDDECMNSVKNGT

YDYPKYEEESKLNRNEIKGSHHHHHH

SEQ ID NO 14: UFV181154 (Signal peptide and tag underlined)
MAIIYLILLFAAVRGDQICIGYHSNNSTEKVDTILERNVTVTHAQDILEKTHNGKLCKLNGI

PPLELGDCSIAGWLLGNPECDRLLTVPEWSYIMEKENPRNGLCYPGSFNDYEELKHLLSSVT

HFEKVKILPRDRWTQHTTTGGSRACAVSGNPSFFRNMVWLTKKGSNYPIAKGSYNNTSGEQM

LIIWGVHHPNDDAEQRTLYQNVGTYVSVGTSTLNKRSVPEIATRPKVNGQGGRMEFSWTILD

MLDTINFESTGNLIAPEYGFRISKRGSSGIMKTEGTLENCETKCQTPLGAINTTLPFHNIHP

LTIGECPKYVKSERLVLATGLRNVPQIESRGLFGAIAGFIEGGWQGMVDGWYGYHWSNDQGS

GYAADKESTQRAIDGITNIVNSVIEKMNTQFEAVGKEFNNLEKRLENLNKKMEDGFLDVWTY

NAELLVLMINERTLDFHDSNVKNLYDKVRMQLRDNAKELGNGCFEFYHKCDDECINSVKNGT

YDYPKYEEESKLNRNEIKSGSLPETGGGSHHHHHH

SEQ ID NO 15: UFV181158 (Signal peptide and tag underlined)
MEKIVLLFAIVSLVQSDQICIGYHANNSTEQVDTIMEKNVTVTHAQDILEKTHNGKLCSLNG

VKPLILRDCSVAGWLLGNPMCDEFLNVPEWSYIVEKDSPINGLCYPGDFNDYEELKHLLSST

NHFEKIQIIPRSSWSNHDASSGVSSACPYNGRSSFFRNVVWLIKKNNAYPTIKRSYNNTNQE

DLLVLWGIHHPNDAAEQTKLYQNPTTYVSVGTSTLNQRSVPEIATRPKVNGQSGRMEFFWTI

LKPNDAINFESNGNFIAPEYAYKIVKKGDSAIMKSGLEYGNCNTKCQTPMGAINSSMPFHNI

HPLTIGECPKYVKSDRLVLATGLRNVPQRETRGLFGAIAGFIEGGWQGMVDGWYGYLHSNEQ

GSGYAADKESTQKAIDGITNKINSIIDKMNTQFEAVGKEFNNLERRIENLNKKMEDGFLDVW

TYNAELLVLMENERTLDFHDSNVKNLYDKVRLQLRDNAKELGNGCFEFYHKCDDECMESVRN

GTYDYPQYSEEARLNREEISGSHHHHHH

-continued

SEQ ID NO 16: UFV181159 (Signal peptide and tag underlined)
MEKIVLLFAIVSLVQSDQICIGYHANNSTEQVDTIMEKNVTVTHAQDILEKTHNGKLCSLNG

VKPLILRDCSVAGWLLGNPMCDEFLNVPEWSYIVEKDSPINGLCYPGDFNDYEELKHLLSST

NHFEKIQIIPRSSWSNHDASSGVSSACPYNGRSSFFRNVVWLIKKNNAYPTIKRSYNNTNQE

DLLVLWGIHHPNDAAEQTKLYQNPTTYVSVGTSTLNQRSVPEIATRPKVNGQSGRMEFFWTI

LKPNDAINFESNGNFIAPEYAYKIVKKGDSAIMKSGLEYGNCNTKCQTPMGAINSSMPFHNI

HPLTIGECPKYVKSDRLVLATGLRNVPQRETRGLFGAIAGFIEGGWQGMVDGWYGYLWSNEQ

GSGYAADKESTQKAIDGITNIINSIIDKMNTQFEAVGKEFNNLERRIENLNKKMEDGFLDVW

TYNAELLVLMINERTLDFHDSNVKNLYDKVRLQLRDNAKELGNGCFEFYHKCDDECIESVRN

GTYDYPQYSEEARLNREEISSGSLPETGGGSHHHHHH

SEQ ID NO 17: UFV181155 (Signal peptide and tag underlined)
METISLITILLVVTASNADKICIGHQSTNSTETVDTLTETNVPVTHAKELLHTEHNGMLCAT

SLGHPLILDTCTIEGLVYGNPSCDLLLGGREWSYIVERSSAVNGTCYPGNVENLEELRTLFS

SASSYQRIQIFPDTTWNVTYTGTSRACSGSFYRSMRWLTQKSGFYPVQDAQYTNNRGKSILF

VWGIHHPPTYTEQTNLYIRNDTTTSVTTEDLNRTFKPVIGPRPLVNGLQGRIDYYWSVLKPG

QTLRVRSNGNLIAPWYGHVLSGGSHGRILKTDLKGGNCVVQCQTEKGGLNSTLPFHNISKYA

FGTCPKYVRVNSLKLAVGLRNVPARSSRGLFGAIAGFIEGGWPGLVAGWYGFQHSNDQGVGM

AADRDSTQKAIDKITSKVNNIVDKMNKQYEIIDHEFSEVETRLNMINNKIDDQIQDVWAYNA

ELLVLLENQKTLDEHDANVNNLYNKVKRALGSNAMEDGKGCFELYHKCDDQCMETIRNGTYN

RRKYREESRLERQKIEGSHHHHHH

SEQ ID NO 18: UFV181156 (Signal peptide and tag underlined)
METISLITILLVVTASNADKICIGHQSTNSTETVDTLTETNVPVTHAKELLHTEHNGMLCAT

SLGHPLILDTCTIEGLVYGNPSCDLLLGGREWSYIVERSSAVNGTCYPGNVENLEELRTLFS

SASSYQRIQIFPDTTWNVTYTGTSRACSGSFYRSMRWLTQKSGFYPVQDAQYTNNRGKSILF

VWGIHHPPTYTEQTNLYIRNDTTTSVTTEDLNRTFKPVIGPRPLVNGLQGRIDYYWSVLKPG

QTLRVRSNGNLIAPWYGHVLSGGSHGRILKTDLKGGNCVVQCQTEKGGLNSTLPFHNISKYA

FGTCPKYVRVNSLKLAVGLRNVPARSSRGLFGAIAGFIEGGWPGLVAGWYGFQWSNDQGVGM

AADRDSTQKAIDKITSIVNNIVDKMNKQYEIIDHEFSEVETRLNMINNKIDDQIQDVWAYNA

ELLVLLINQKTLDEHDANVNNLYNKVKRALGSNAMEDGKGCFELYHKCDDQCIETIRNGTYN

RRKYREESRLERQKIESGSLPETGGGSHHHHHH

SEQ ID NO 19: UFV181141 (Signal peptide and tag underlined)
MKTIIALSYIFCLALGQDLPGNDNSTATLCLGHHAVPNGTLVKTITDDQIEVTNATELVQSS

STGKICNNPHRILDGIDCTLIDALLGDPHCDVFQNETWDLFVERSKAFSNCYPYDVPDYASL

RSLVASSGTLEFITEGFTWTGVTQNGGSNACKRGPGSGFFSRLNWLTKSGSTYPVLNVTMPN

NDNFDKLYIWGVHHPSTNQEQTSLYVQASGRVTVSTRRSQQTIIPNIGSRPWVRGLSSRISI

YWTIVKPGDVLVINSNGNLIAPRGYFKMRTGKSSIMRSDAPIDTCISECITPNGSIPNDKPF

QNVNKITYGACPKYVKQNTLKLATGMRNVPEKQTRGLFGAIAGFIENGWEGMIDGWYGFRHQ

NSEGTGQAADLKSTQAAIDQINGKLNRVIEKTNEKFHQIEKEFSEVEGRIQDLEKYVEDTKI

DLWSYNAELLVALENQHTIDLTDSEMNKLFEKTRRQLRENAEDMGNGCFKIYHKCDNACIES

IRNGTYDHDVYRDEALNNRFQIKGVGSHHHHHH

SEQ ID NO 20: UFV180660 (Signal peptide and tag underlined)
MKTIIALSYIFCLALGQDLPGNDNSTATLCLGHHAVPNGTLVKTITDDQIEVTNATELVQSS

STGKICNNPHRILDGIDCTLIDALLGDPHCDVFQNETWDLFVERSKAFSNCYPYDVPDYASL

-continued

RSLVASSGTLEFITEGFTWTGVTQNGGSNACKRGPGSGFFSRLNWLTKSGSTYPVLNVTMPN

NDNFDKLYIWGVHHPSTNQEQTSLYVQASGRVTVSTRRSQQTIIPNIWSRPWVRGLSSRISI

YWTIVKPGDVLVINSNGNLIAPRGYFKMRTGKSSIMRSDAPIDTCISECITPNGSIPNDKPF

QNVNKITYGACPKYVKQNTLKLATGMRNVPEKQTRGLFGAIAGFIENGWEGMIDGWYGFRWQ

NSEGTGQAADLKSTQAAIDQINGILNRVIEKMNEKFHQIEKEFSEVEGRIQDLEKYVEDTKI

DLWSYNAELLVALINQHTIDLTDSEMNKLFEKTRRQLRENAEDMGNGCFKIYHKCDNACIES

IRNGNYDHDVYRDEALNNRFQIKGVSGSLPETGGGSHHHHHH

SEQ ID NO 21: UFV181137 (Signal peptide and tag underlined)
MKTIIALSYILCLVFAQKLPGNDNSTATLCLGHHAVSNGTLVKTITNDQIEVTNATELVQSS

STGRICDSPHQILDGENCTLIDALLGDPHCDGFQNKEWDLFVERSKAYSNCYPYDVPDYASL

RSLVASSGTLEFNNESFNWTGVAQNGTSSACKRRSNKSFFSRLNWLHQLKYKYPALNVTMPN

NEKFDKLYIWGVHHPSTDSDQISIYAQASGRVTVSTKRSQQTVIPNIGSSPWVRGVSSRISI

YWTIVKPGDILLINSTGNLIAPRGYFKIRSGKSSIMRSDAPIGKCNSECITPNGSIPNDKPF

QNVNRITYGACPRYVKQNTLKLATGMRNVPEKQTRGIFGAIAGFIENGWEGMVDGWYGFRHQ

NSEGTGQAADLKSTQAAINQINGKLNRLIEKTNEKFHQIEKEFSEVEGRIQDLEKYVEDTKI

DLWSYNAELLVALENQHTIDLTDSEMNKLFERTKKQLRENAEDMGNGCFKIYHKCDNACIGS

IRNGTYDHDVYRDEALNNRFQIKGVGSHHHHHH

SEQ ID NO 22: UFV181096 (Signal peptide and tag underlined)
MKTIIALSYILCLVFAQKLPGNDNSTATLCLGHHAVSNGTLVKTITNDQIEVTNATELVQSS

STGRICDSPHQILDGENCTLIDALLGDPHCDGFQNKEWDLFVERSKAYSNCYPYDVPDYASL

RSLVASSGTLEFNNESFNWTGVAQNGTSSACKRRSNKSFFSRLNWLHQLKYKYPALNVTMPN

NEKFDKLYIWGVHHPSTDSDQISIYAQASGRVTVSTKRSQQTVIPNIGSSPWVRGVSSRISI

YWTIVKPGDILLINSTGNLIAPRGYFKIRSGKSSIMRSDAPIGKCNSECITPNGSIPNDKPF

QNVNRITYGACPRYVKQNTLKLATGMRNVPEKQTRGIFGAIAGFIENGWEGMVDGWYGFRWQ

NSEGTGQAADLKSTQAAINQINGILNRLIEKTNEKFHQIEKEFSEVEGRIQDLEKYVEDTKI

DLWSYNAELLVALINQHTIDLTDSEMNKLFERTKKQLRENAEDMGNGCFKIYHKCDNACIGS

IRNGTYDHDVYRDEALNNRFQIKGVSGSLPETGGGSHHHHHH

SEQ ID NO 23: UFV181145 (Signal peptide and tag underlined)
MIALILVALALSHTAYSQITNGTRGNPIICLGHHAVENGTSVKTLTDNHVEVVSAKELVETN

HTDELCPSPLKLVDGQDCDLINGALGSPGCDRLQDTTWDVFIERPTAVDTCYPFDVPDYQSL

RSILASSGSLEFIAEQFTWNGVKVDGSSSACLRGGRNSFFSRLNWLTKETNGNYGPINVTKE

NTGSYVRLYLWGVHHPSSDNEQTDLYKVATGRVTVSTRSDQISIVPNIGSRPRVRNQSGRIS

IYWTLVNPGDSIIFNSIGNLIAPRGHYKISKSTKSTVLKSDKRIGSCTSPCLTDKGSIQSDK

PFQNVSRIAIGNCPKYVKQGSLMLATGMRNIPGKQAKGLFGAIAGFIENGWQGLIDGWYGFR

HQNAEGTGTAADLKSTQAAIDQINGKLNRLIEKTNEKYHQIEKEFEQVEGRIQDLEKYVEDT

KIDLWSYNAELLVALENQHTIDVTDSEMNKLFERVRRQLRENAEDQGNGCFEIFHQCDNNCI

ESIRNGTYDHNIYRDEAINNRIKINPVGSHHHHHH

SEQ ID NO 24: UFV180661 (Signal peptide and tag underlined)
MIALILVALALSHTAYSQITNGTRGNPIICLGHHAVENGTSVKTLTDNHVEVVSAKELVETN

HTDELCPSPLKLVDGQDCDLINGALGSPGCDRLQDTTWDVFIERPTAVDTCYPFDVPDYQSL

RSILASSGSLEFIAEQFTWNGVKVDGSSSACLRGGRNSFFSRLNWLTKETNGNYGPINVTKE

NTGSYVRLYLWGVHHPSSDNEQTDLYKVATGRVTVSTRSDQISIVPNIGSRPRVRNQSGRIS

-continued
IYWTLVNPGDSIIFNSIGNLIAPRGHYKISKSTKSTVLKSDKRIGSCTSPCLTDKGSIQSDK

PFQNVSRIAIGNCPKYVKQGSLMLATGMRNIPGKQAKGLFGAIAGFIENGWQGLIDGWYGFR

WQNAEGTGTAADLKSTQAAIDQINGILNRLIEKMNEKYHQIEKEFEQVEGRIQDLEKYVEDT

KIDLWSYNAELLVALINQHTIDVTDSEMNKLFERVRRQLRENAEDQGNGCFEIFHQCDNNCI

ESIRNGTYDHNIYRDEAINNRIKINPVGSLPETGGGSHHHHHH

SEQ ID NO 25: UFV181146 (Signal peptide and tag underlined)
MNTQILVFALMAIIPTNADKICLGHHAVSNGTKVNTLTERGVEVVNATETVERTNVPRICSK

GKRTVDLGQCGLLGTITGPPQCDQFLEFSADLIIERREGSDVCYPGKFVNEEALRQILRESG

GIDKETMGFTYSGIRTNGATSACRRSGSSFYAEMKWLLSNTDNAAFPQMTKSYKNTRKDPAL

IIWGIHHSGSTTEQTKLYGSGNKLITVGSSNYQQSFVPSPGARPQVNGQSGRIDFHWLILNP

NDTVTFSFNGAFIAPDRASFLRGKSMGIQSGVQVDANCEGDCYHSGGTIISNLPFQNINSRA

VGKCPRYVKQESLLLATGMKNVPEIPKGRGLFGAIAGFIENGWEGLIDGWYGFRHQNAQGEG

TAADYKSTQSAIDQITGKLNRLIEKTNQQFELIDNEFTEVEKQIGNVINWTRDSMTEVWSYN

AELLVAMENQHTIDLADSEMNKLYERVKRQLRENAEEDGTGCFEIFHKCDDDCMASIRNNTY

DHSKYREEAMQNRIQIDPVGSHHHHHH

SEQ ID NO 26: UFV180664 (Signal peptide and tag underlined)
MNTQILVFALMAIIPTNADKICLGHHAVSNGTKVNTLTERGVEVVNATETVERTNVPRICSK

GKRTVDLGQCGLLGTITGPPQCDQFLEFSADLIIERREGSDVCYPGKFVNEEALRQILRESG

GIDKETMGFTYSGIRTNGATSACRRSGSSFYAEMKWLLSNTDNAAFPQMTKSYKNTRKDPAL

IIWGIHHSGSTTEQTKLYGSGNKLITVGSSNYQQSFVPSPGARPQVNGQSGRIDFHWLILNP

NDTVTFSFNGAFIAPDRASFLRGKSMGIQSGVQVDANCEGDCYHSGGTIISNLPFQNINSRA

VGKCPRYVKQESLLLATGMKNVPEIPKGRGLFGAIAGFIENGWEGLIDGWYGFRWQNAQGEG

TAADYKSTQSAIDQITGILNRLIEKMNQQFELIDNEFTEVEKQIGNVINWTRDSMTEVWSYN

AELLVAMINQHTIDLADSEMNKLYERVKRQLRENAEEDGTGCFEIFHKCDDDCMASIRNNTY

DHSKYREEAMQNRIQIDPVSGSLPETGGGSHHHHHH

SEQ ID NO 27: UFV181147 (Signal peptide and tag underlined)
MYKVVVIIALLGAVKGLDRICLGHHAVANGTIVKTLTNEQEEVTNATETVESTNLNKLCMKG

RSYKDLGNCHPVGMLIGTPVCDPHLTGTWDTLIERENAIAHCYPGATINEEALRQKIMESGG

ISKMSTGFTYGSSINSAGTTKACMRNGGDSFYAELKWLVSKTKGQNFPQTTNTYRNTDTAEH

LIIWGIHHPSSTQEKNDLYGTQSLSISVESSTYQNNFVPVVGARPQVNGQSGRIDFHWTLVQ

PGDNITFSHNGGLIAPSRVSKLTGRGLGIQSEALIDNSCESKCFWRGGSINTKLPFQNLSPR

TVGQCPKYVNQRSLLLATGMRNVPEVVQGRGLFGAIAGFIENGWEGMVDGWYGFRHQNAQGT

GQAADYKSTQAAIDQITGKLNRLIEKTNTEFESIESEFSETEHQIGNVINWTKDSITDIWTY

QAELLVAMENQHTIDMADSEMLNLYERVKQLRQNAEEDGKGCFEIYHTCDDSCMESIRNNT

YDHSQYREEALLNRLNINSVGSHHHHHH

SEQ ID NO 28: UFV180662 (Signal peptide and tag underlined)
MYKVVVIIALLGAVKGLDRICLGHHAVANGTIVKTLTNEQEEVTNATETVESTNLNKLCMKG

RSYKDLGNCHPVGMLIGTPVCDPHLTGTWDTLIERENAIAHCYPGATINEEALRQKIMESGG

ISKMSTGFTYGSSINSAGTTKACMRNGGDSFYAELKWLVSKTKGQNFPQTTNTYRNTDTAEH

LIIWGIHHPSSTQEKNDLYGTQSLSISVESSTYQNNFVPVVGARPQVNGQSGRIDFHWTLVQ

PGDNITFSHNGGLIAPSRVSKLTGRGLGIQSEALIDNSCESKCFWRGGSINTKLPFQNLSPR

TVGQCPKYVNQRSLLLATGMRNVPEVVQGRGLFGAIAGFIENGWEGMVDGWYGFRWQNAQGT

GQAADYKSTQAAIDQITGILNRLIEKMNTEFESIESEFSETEHQIGNVINWTKDSITDIWTY

-continued

QAELLVAMINQHTIDMADSEMLNLYERVRKQLRQNAEEDGKGCFEIYHTCDDSCMESIRNNT

YDHSQYREEALLNRLNINSSGSLPETGGGSHHHHHH

SEQ ID NO 29: UFV4239 (Signal peptide and tag underlined)
MKAILVVLLYTFATANADTLCIGYHANNSTDTVDTVLEKNVTVTHSVNLLEDKHNGKLCKLR

GVAPLHLGKCNIAGWILGNPECESLSTASSWSYIVETPSSDNGTCYPGDFIDYEELREQLSS

VSSFERFEIFPKTSSWPNHDSNKGVTAACPHAGAKSFYKNLIWLVKKGNSYPKLSKSYINDK

GKEVLVLWGIHHPSTSADQQSLYQNADAYVFVGSSRYSKKFKPEIAIRPKVRDQEGRMNYYW

TLVEPGDKITFEATGNLVVPRYAFAMERNAGSGIIISDTPVHDCNTTCQTPKGAINTSLPFQ

NIHPITIGKCPKYVKSTKLRLATGLRNIPSIQSQGLFGAIAGFIEGGWTGMVDGWYGYHHQN

EQGSGYAADLKSTQNAIDEITNKVNSVIEKMNTQFTAVGKEFNHLEKRIENLNKKVDDGFLD

IWTYNAELLVLLENERTLDYHDSNVKNLYEKVRSQLKNNAKEIGNGCFEFYHKCDNTCMESV

KNGTYDYPKYSEEAKLNREEIDGRSLVPRGSGHHHHHH

SEQ ID NO 30: UFV180843 (Signal peptide and tag underlined)
MKAILVVLLYTFTTANADTLCIGYHANNSTDTVDTVLEKNVTVTHSVNLLEDKHNGKLCKLR

GVAPLHLGKCNIAGWILGNPECESLSTASSWSYIVETSNSDNGTCYPGDFINYEELREQLSS

VSSFERFEIFPKTSSWPNHDSNKGVTAACPHAGAKSFYKNLIWLVKKGNSYPKLNQSYINDK

GKEVLVLWGIHHPSTTADQQSLYQNADAYVFVGTSRYSKKFKPEIATRPKVRDQEGRMNYYW

TLVEPGDKITFEATGNLVVPRYAFTMERNAGSGIIISDTPVHDCNTTCQTPEGAINTSLPFQ

NIHPITIGKCPKYVKSTKLRLATGLRNVPSIQSRGLFGAIAGFIEGGWTGMVDGWYGYHHQN

EQGSGYAADLKSTQNAIDKITNKVNSVIEKMNTQFTAVGKEFNHLEKRIENLNKKVDDGFLD

IWTYNAELLVLLENERTLDYHDSNVKNLYEKVRNQLKNNAKEIGNGCFEFYHKCDNTCMESV

KNGTYDYPKYSEEAKLNREKIDSGSLVPSGSPGSGYIPEAPRDGQAYVRKDGEWVLLSTFLG

GSLPETGGGSHHHHHH

SEQ ID NO 31: UFV180436 (Signal peptide and tag underlined)
MKTIIALSYIFCLALGQDLPGNDNSTATLCLGHHAVPNGTLVKTITDDQIEVTNATELVQSS

STGKICNNPHRILDGIDCTLIDALLGDPHCDVFQNETWDLFVERSKAFSNCYPYDVPDYASL

RSLVASSGTLEFITEGFTWTGVTQNGGSNACKRGPGSGFFSRLNWLTKSGSTYPVLNVTMPN

NDNFDKLYIWGVHHPSTNQEQTSLYVQASGRVTVSTRRSQQTIIPNIGSRPWVRGLSSRISI

YWTIVKPGDVLVINSNGNLIAPRGYFKMRTGKSSIMRSDAPIDTCISECITPNGSIPNDKPF

QNVNKITYGACPKYVKQNTLKLATGMRNVPEKQTRGLFGAIAGFIENGWEGMIDGWYGFRHQ

NSEGTGQAADLKSTQAAIDQINGKLNRVIEKTNEKFHQIEKEFSEVEGRIQDLEKYVEDTKI

DLWSYNAELLVALENQHTIDLTDSEMNKLFEKTRRQLRENAEDMGNGCFKIYHKCDNACIES

IRNGTYDHDVYRDEALNNRFQSGSLVPSGSPGSGYIPEAPRDGQAYVRKDGEWVLLSTFLGG

SLPETGGGSHHHHHH

SEQ ID NO 32: UFV170466 (Signal peptide and tag underlined)
MKTIVALSYILCLVFAQKLPGNDNSTATLCLGHHAVPNGTIVKTITNDQIEVTNATELVQSS

STGEICDSPHQILDGENCTLIDALLGDPQCDGFQNKKWDLFVERSKAYSNCYPYDVPDYASL

RSLVASSGTLEFNNESFNWTGVTQNGTSSACIRRSNSSFFSRLNWLTHLNFKYPALNVTMPN

NEQFDKLYIWGVHHPGTDKDQIFLYAQSSGRITVSTKRSQQAVIPNIGSRPRIRNIPSRISI

YWTIVKPGDILLINSTGNLIAPRGYFKIRSGKSSIMRSDAPIGKCNSECITPNGSIPNDKPF

QNVNRITYGACPRYVKQSTLKLATGMRNVPEKQTRGIFGAIAGFIENGWEGMVDGWYGFRHQ

NSEGRGQAADLKSTQAAIDQINGKLNRLIGKTNEKFHQIEKEFSEVEGRIQDLEKYVEDTKI

-continued

DLWSYNAELLVALENQHTIDLTDSEMNKLFEKTKKQLRENAEDMGNGCFKIYHKCDNACIGS

IRNGTYNHDVYRDEALNNRFQSGSLVPRGSGSGYIPEAPRDGQAYVRKDGEWVLLSTFLGGS

EPEA

SEQ ID NO 33: UFV181099 (Signal peptide and tag underlined)
MKTIVALSYILCLVFAQKLPGNDNSTATLCLGHHAVPNGTIVKTITNDQIEVTNATELVQSS

STGEICDSPHQILDGENCTLIDALLGDPQCDGFQNKKWDLFVERSKAYSNCYPYDVPDYASL

RSLVASSGTLEFNNESFNWTGVTQNGTSSACIRRSNSSFFSRLNWLTHLNFKYPALNVTMPN

NEQFDKLYIWGVHHPGTDKDQIFLYAQSSGRITVSTKRSQQAVIPNIGSRPRIRNIPSRISI

YWTIVKPGDILLINSTGNLIAPRGYFKIRSGKSSIMRSDAPIGKCNSECITPNGSIPNDKPF

QNVNRITYGACPRYVKQSTLKLATGMRNVPEKQTRGIFGAIAGFIENGWEGMVDGWYGFRWQ

NSEGRGQAADLKSTQAAIDQINGILNRLIGKTNEKFHQIEKEFSEVEGRIQDLEKYVEDTKI

DLWSYNAELLVALINQHTIDLTDSEMNKLFEKTKKQLRENAEDMGNGCFKIYHKCDNACIGS

IRNGTYNHDVYRDEALNNRFQIKGVSGSLPETGGGSHHHHHH

SEQ ID NO 34: UFV181005 (Signal peptide and tag underlined)
MKAILVVLLYTFATANADTLCIGYHANNSTDTVDTVLEKNVTVTHSVNLLEDKHNGKLCKLR

GVAPLHLGKCNIAGWILGNPECESLSTASSWSYIVETPSSDNGTCYPGDFIDYEELREQLSS

VSSFERFEIFPKTSSWPNHDSNKGVTAACPHAGAKSFYKNLIWLVKKGNSYPKLSKSYINDK

GKEVLVLWGIHHPSTSADQQSLYQNADAYVFVGSSRYSKKFKPEIAIRPKVRDQEGRMNYYW

TLVEPGDKITFEATGNLVVPRYAFAMERNAGSGIIISDTPVHDCNTTCQTPKGAINTSLPFQ

NIHPITIGKCPKYVKSTKLRLATGLRNIPSIQSRGLFGAIAGFIEGGWTGMVDGWYGYHWQN

EQGSGYAADLKSTQNAIDEITNKVNSVIEKMNTQFTAVGKEFNHLEKRIENLNKKVDDGFLD

IWTYNAELLVLLENERTLDYHDSNVKNLYEKVRSQLKNNAKEIGNGCFEFYHKCDNTCIESV

KNGTYDYPKYSEEAKLNREEIDSGSLPETGGGSHHHHHH

SEQ ID NO 35: UFV181007 (Signal peptide and tag underlined)
MKAILVVLLYTFATANADTLCIGYHANNSTDTVDTVLEKNVTVTHSVNLLEDKHNGKLCKLR

GVAPLHLGKCNIAGWILGNPECESLSTASSWSYIVETPSSDNGTCYPGDFIDYEELREQLSS

VSSFERFEIFPKTSSWPNHDSNKGVTAACPHAGAKSFYKNLIWLVKKGNSYPKLSKSYINDK

GKEVLVLWGIHHPSTSADQQSLYQNADAYVFVGSSRYSKKFKPEIAIRPKVRDQEGRMNYYW

TLVEPGDKITFEATGNLVVPRYAFAMERNAGSGIIISDTPVHDCNTTCQTPKGAINTSLPFQ

NIHPITIGKCPKYVKSTKLRLATGLRNIPSIQSRGLFGAIAGFIEGGWTGMVDGWYGYHHQN

EQGSGYAADLKSTQNAIDEITNIVNSVIEKMNTQFTAVGKEFNHLEKRIENLNKKVDDGFLD

IWTYNAELLVLLINERTLDYHDSNVKNLYEKVRSQLKNNAKEIGNGCFEFYHKCDNTCMESV

KNGTYDYPKYSEEAKLNREEIDSGSLPETGGGSHHHHHH

SEQ ID NO 36: UFV181090 (signal peptide and tag underlined)
MKVKLLVLLCTFTATYADTICIGYHANNSTDTVDTVLEKNVTVTHSVNLLENSHNGKLCLLK

GIAPLQLGNCSVAGWILGNPECELLISKESWSYIVEKPNPENGTCYPGHFADYEELREQLSS

VSSFERFEIFPKESSWPNHTVTGVSASCSHNGESSFYRNLLWLTGKNGLYPNLSKSYANNKE

KEVLVLWGVHHPPNIGDQKALYHTENAYVSVVSSHYSRKFTPEIAKRPKVRDQEGRINYYWT

LLEPGDTIIFEANGNLIAPRYAFALSRGFGSGIINSNAPMDKCDAKCQTPQGAINSSLPFQN

VHPVTIGECPKYVRSAKLRMVTGLRNIPSIQSRGLFGAIAGFIEGGWTGMVDGWYGYHWQNE

QGSGYAADQKSTQNAINGITNIVNSVIEKMNTQFTAVGKEFNKLERRMENLNKKVDDGFIDI

WTYNAELLVLLINERTLDFHDSNVKNLYEKVKSQLKNNAKEIGNGCFEFYHKCNDECIESVK

NGTYDYPKYSEESKLNREKIDSGSLPETGGGSHHHHHH

-continued

SEQ ID NO 37: UFV181135 (signal peptide and tag underlined)
MKVKLLVLLCTFTATYADTICIGYHANNSTDTVDTVLEKNVTVTHSVNLLENSHNGKLCLLK

GIAPLQLGNCSVAGWILGNPECELLISKESWSYIVEKPNPENGTCYPGHFADYEELREQLSS

VSSFERFEIFPKESSWPNHTVTGVSASCSHNGESSFYRNLLWLTGKNGLYPNLSKSYANNKE

KEVLVLWGVHHPPNIGDQKALYHTENAYVSVVSSHYSRKFTPEIAKRPKVRDQEGRINYYWT

LLEPGDTIIFEANGNLIAPRYAFALSRGFGSGIINSNAPMDKCDAKCQTPQGAINSSLPFQN

VHPVTIGECPKYVRSAKLRMVTGLRNIPSIQSQGLFGAIAGFIEGGWTGMVDGWYGYHHQNE

QGSGYAADQKSTQNAINGITNKVNSVIEKMNTQFTAVGKEFNKLERRMENLNKKVDDGFIDI

WTYNAELLVLLENERTLDFHDSNVKNLYEKVKSQLKNNAKEIGNGCFEFYHKCNDECMESVK

NGTYDYPKYSEESKLNREKIDGSHHHHHH

SEQ ID NO 38: UFV181084 (signal peptide and tag underlined)
MEARLLVLLCAFAATNADTICIGYHANNSTDTVDTVLEKNVTVTHSVNLLEDSHNGKLCKLK

GIAPLQLGKCNIAGWLLGNPECDLLLTASSWSYIVETSNSENGTCYPGDFIDYEELREQLSS

VSSFEKFEIFPKTSSWPNHETTKGVTAACSYAGASSFYRNLLWLTKKGSSYPKLSKSYVNNK

GKEVLVLWGVHHPPTGTDQQSLYQNADAYVSVGSSKYNRRFTPEIAARPKVRDQAGRMNYYW

TLLEPGDTITFEATGNLIAPWYAFALNRGSGSGIITSDAPVHDCNTKCQTPHGAINSSLPFQ

NIHPVTIGECPKYVRSTKLRMATGLRNIPSIQSRGLFGAIAGFIEGGWTGMIDGWYGYHWQN

EQGSGYAADQKSTQNAIDGITNIVNSVIEKMNTQFTAVGKEFNNLERRIENLNKKVDDGFLD

IWTYNAELLVLLINERTLDFHDSNVRNLYEKVKSQLKNNAKEIGNGCFEFYHKCDDACIESV

RNGTYDYPKYSEESKLNREEIDGSLPETGGGSHHHHHH

SEQ ID NO 39: UFV181131 (signal peptide and tag underlined)
MEARLLVLLCAFAATNADTICIGYHANNSTDTVDTVLEKNVTVTHSVNLLEDSHNGKLCKLK

GIAPLQLGKCNIAGWLLGNPECDLLLTASSWSYIVETSNSENGTCYPGDFIDYEELREQLSS

VSSFEKFEIFPKTSSWPNHETTKGVTAACSYAGASSFYRNLLWLTKKGSSYPKLSKSYVNNK

GKEVLVLWGVHHPPTGTDQQSLYQNADAYVSVGSSKYNRRFTPEIAARPKVRDQAGRMNYYW

TLLEPGDTITFEATGNLIAPWYAFALNRGSGSGIITSDAPVHDCNTKCQTPHGAINSSLPFQ

NIHPVTIGECPKYVRSTKLRMATGLRNIPSIQSRGLFGAIAGFIEGGWTGMIDGWYGYHHQN

EQGSGYAADQKSTQNAIDGITNKVNSVIEKMNTQFTAVGKEFNNLERRIENLNKKVDDGFLD

IWTYNAELLVLLENERTLDFHDSNVRNLYEKVKSQLKNNAKEIGNGCFEFYHKCDDACMESV

RNGTYDYPKYSEESKLNREEIDGSHHHHHH

SEQ ID NO 40: UFV181095 (signal peptide and tag underlined)
MKTIIALSYILCLVFAQKLPGNDNSTATLCLGHHAVPNGTLVKTITNDQIEVTNATELVQSS

STGRICDSPHRILDGKNCTLIDALLGDPHCDGFQNKEWDLFVERSKAYSNCYPYDVPDYASL

RSLVASSGTLEFINEDFNWTGVAQDGKSYTCKRGSVNSFFSRLNWLHKLEYKYPALNVTMPN

NGKFDKLYIWGVHHPSTDSDQTSLYVRASGRVTVSTKRSQQTVIPNIGSRPWVRGLSSRISI

YWTIVKPGDILLINSTGNLIAPRGYFKIRNGKSSIMRSDAPIGNCSSECITPNGSIPNDKPF

QNVNRITYGACPRYVKQNTLKLATGMRNVPEKQTRGIFGAIAGFIENGWEGMVDGWYGFRWQ

NSEGTGQAADLKSTQAAIDQINGILNRLIEKTNEKFHQIEKEFSEVEGRIQDLEKYVEDTKI

DLWSYNAELLVALINQHTIDLTDSEMNKLFERTRKQLRENAEDMGNGCFKIYHKCDNACIGS

IRNGTYDHDVYRDEALNNRFQIKGVSGSLPETGGGSHHHHHH

SEQ ID NO 41: UFV181140 (signal peptide and tag underlined)
MKTIIALSYILCLVFAQKLPGNDNSTATLCLGHHAVPNGTLVKTITNDQIEVTNATELVQSS

STGRICDSPHRILDGKNCTLIDALLGDPHCDGFQNKEWDLFVERSKAYSNCYPYDVPDYASL

-continued

RSLVASSGTLEFINEDFNWTGVAQDGKSYTCKRGSVNSFFSRLNWLHKLEYKYPALNVTMPN

NGKFDKLYIWGVHHPSTDSDQTSLYVRASGRVTVSTKRSQQTVIPNIGSRPWVRGLSSRISI

YWTIVKPGDILLINSTGNLIAPRGYFKIRNGKSSIMRSDAPIGNCSSECITPNGSIPNDKPF

QNVNRITYGACPRYVKQNTLKLATGMRNVPEKQTRGIFGAIAGFIENGWEGMVDGWYGFRHQ

NSEGTGQAADLKSTQAAIDQINGKLNRLIEKTNEKFHQIEKEFSEVEGRIQDLEKYVEDTKI

DLWSYNAELLVALENQHTIDLTDSEMNKLFERTRKQLRENAEDMGNGCFKIYHKCDNACIGS

IRNGTYDHDVYRDEALNNRFQIKGVGSHHHHHH

SEQ ID NO 42: UFV181093 (signal peptide and tag underlined)
MKTIIALSYIFCQVLAQNLPGNDNSTATLCLGHHAVPNGTLVKTITNDQIEVTNATELVQSS

STGRICDSPHRILDGKNCTLIDALLGDPHCDGFQNEKWDLFVERSKAFSNCYPYDVPDYASL

RSLVASSGTLEFINEGFNWTGVTQNGGSYACKRGPDKSFFSRLNWLYESESTYPVLNVTMPN

NDNFDKLYIWGVHHPSTDKEQTNLYVQASGRVTVSTKRSQQTIIPNVGSRPWVRGLSSRISI

YWTIVKPGDILLINSNGNLIAPRGYFKIRTGKSSIMRSDAPIGTCSSECITPNGSIPNDKPF

QNVNKITYGACPKYVKQNTLKLATGMRNVPEKQTRGIFGAIAGFIENGWEGMIDGWYGFRWQ

NSEGTGQAADLKSTQAAIDQINGILNRVIEKTNEKFHQIEKEFSEVEGRIQDLEKYVEDTKI

DLWSYNAELLVALINQHTIDLTDSEMNKLFEKTRRQLRENAEDMGNGCFKIYHKCDNACIGS

IRNGTYDHDVYRDEALNNRFQIKGVSGSLPETGGGSHHHHHH

SEQ ID NO 43: UFV181136 (signal peptide and tag underlined)
MKTIIALSYIFCQVLAQNLPGNDNSTATLCLGHHAVPNGTLVKTITNDQIEVTNATELVQSS

STGRICDSPHRILDGKNCTLIDALLGDPHCDGFQNEKWDLFVERSKAFSNCYPYDVPDYASL

RSLVASSGTLEFINEGFNWTGVTQNGGSYACKRGPDKSFFSRLNWLYESESTYPVLNVTMPN

NDNFDKLYIWGVHHPSTDKEQTNLYVQASGRVTVSTKRSQQTIIPNVGSRPWVRGLSSRISI

YWTIVKPGDILLINSNGNLIAPRGYFKIRTGKSSIMRSDAPIGTCSSECITPNGSIPNDKPF

QNVNKITYGACPKYVKQNTLKLATGMRNVPEKQTRGIFGAIAGFIENGWEGMIDGWYGFRHQ

NSEGTGQAADLKSTQAAIDQINGKLNRVIEKTNEKFHQIEKEFSEVEGRIQDLEKYVEDTKI

DLWSYNAELLVALENQHTIDLTDSEMNKLFEKTRRQLRENAEDMGNGCFKIYHKCDNACIGS

IRNGTYDHDVYRDEALNNRFQIKGVGSHHHHHH

SEQ ID NO 44: UFV181097 (signal peptide and tag underlined)
MKTIIALSYILCLVFAQKLPGNDNSTATLCLGHHAVPNGTIVKTITNDQIEVTNATELVQSS

STGGICDSPHQILDGENCTLIDALLGDPQCDGFQNKKWDLFVERSKAYSNCYPYDVPDYASL

RSLVASSGTLEFNDESFNWTGVTQNGTSSSCKRRSNNSFFSRLNWLTHLKFKYPALNVTMPN

NEKFDKLYIWGVHHPVTDNDQIFLYAQASGRITVSTKRSQQTVIPNIGSRPRIRNIPSRISI

YWTIVKPGDILLINSTGNLIAPRGYFKIRSGKSSIMRSDAPIGKCNSECITPNGSIPNDKPF

QNVNRITYGACPRYVKQNTLKLATGMRNVPEKQTRGIFGAIAGFIENGWEGMVDGWYGFRWQ

NSEGIGQAADLKSTQAAINQINGILNRLIGKTNEKFHQIEKEFSEVEGRIQDLEKYVEDTKI

DLWSYNAELLVALINQHTIDLTDSEMNKLFERTKKQLRENAEDMGNGCFKIYHKCDNACIGS

IRNGTYDHDVYRDEALNNRFQIKGVSGSLPETGGGSHHHHHH

SEQ ID NO 45: UFV181138 (signal peptide and tag underlined)
MKTIIALSYILCLVFAQKLPGNDNSTATLCLGHHAVPNGTIVKTITNDQIEVTNATELVQSS

STGGICDSPHQILDGENCTLIDALLGDPQCDGFQNKKWDLFVERSKAYSNCYPYDVPDYASL

RSLVASSGTLEFNDESFNWTGVTQNGTSSSCKRRSNNSFFSRLNWLTHLKFKYPALNVTMPN

NEKFDKLYIWGVHHPVTDNDQIFLYAQASGRITVSTKRSQQTVIPNIGSRPRIRNIPSRISI

-continued

YWTIVKPGDILLINSTGNLIAPRGYFKIRSGKSSIMRSDAPIGKCNSECITPNGSIPNDKPF

QNVNRITYGACPRYVKQNTLKLATGMRNVPEKQTRGIFGAIAGFIENGWEGMVDGWYGFRHQ

NSEGIGQAADLKSTQAAINQINGKLNRLIGKTNEKFHQIEKEFSEVEGRIQDLEKYVEDTKI

DLWSYNAELLVALENQHTIDLTDSEMNKLFERTKKQLRENAEDMGNGCFKIYHKCDNACIGS

IRNGTYDHDVYRDEALNNRFQIKGVGSHHHHHH

SEQ ID NO 46: UFV181148 (signal peptide and tag underlined)
MLSIVILFLLVAENSSQNYTGNPVICMGHHAVANGTMVKILTDDQVEVVTAQELVESQNLPE

LCPSPLRLVDGQTCDIINGALGSPGCDHLNGAEWDVFIERPNAMDTCYPFDVPDYQSLRSIL

ANNGKFEFIAEEFQWTTVKQNGKSGACKRANVNDFFRRLNWLVKSDRNAYPLQNLTKVNNGD

YARLYIWGVHHPSTDTEQTNLYKNNPGRVTVSTKTSQTSVIPNIGSRPWVRGQSGRISFYWT

IVEPGDLIVFNTIGNLIAPRGHYKLNNQKKGTILNTAIPIGSCVSKCHTDKGSLSTTKPFQN

ISRIAIGDCPKYVKQGSLKLATGMRNIPEKASRGLFGAIAGFIENGWQGLIDGWYGFRHQNA

EGTGTAADLKSTQAAIDQINGKLNRLIEKTNEKYHQIEKEFEQVEGRIQDLEKYVEDTKIDL

WSYNAELLVALENQHTIDVTDSEMNKLFERVRRQLRENAEDKGNGCFEIFHKCDNNCIESIR

NGTYDHDIYRDEAINNRFQIQGVGSHHHHHH

SEQ ID NO 47: UFV181149 (signal peptide and tag underlined)
MLSIVILFLLVAENSSQNYTGNPVICMGHHAVANGTMVKILTDDQVEVVTAQELVESQNLPE

LCPSPLRLVDGQTCDIINGALGSPGCDHLNGAEWDVFIERPNAMDTCYPFDVPDYQSLRSIL

ANNGKFEFIAEEFQWTTVKQNGKSGACKRANVNDFFRRLNWLVKSDRNAYPLQNLTKVNNGD

YARLYIWGVHHPSTDTEQTNLYKNNPGRVTVSTKTSQTSVIPNIGSRPWVRGQSGRISFYWT

IVEPGDLIVFNTIGNLIAPRGHYKLNNQKKGTILNTAIPIGSCVSKCHTDKGSLSTTKPFQN

ISRIAIGDCPKYVKQGSLKLATGMRNIPEKASRGLFGAIAGFIENGWQGLIDGWYGFRWQNA

EGTGTAADLKSTQAAIDQINGILNRLIEKTNEKYHQIEKEFEQVEGRIQDLEKYVEDTKIDL

WSYNAELLVALINQHTIDVTDSEMNKLFERVRRQLRENAEDKGNGCFEIFHKCDNNCIESIR

NGTYDHDIYRDEAINNRFQIQGVSGSLPETGGGSHHHHHH

SEQ ID NO 50: UFV190839 (signal peptide and tag underlined
MKTIIALSYIFCLALGQDLPGNDNSTATLCLGHHAVPNGTLVKTITDDQIEVTNATELVQSS

STGKICNNPHRILDGIDCTLIDALLGDPHCDVFQNETWDLFVERSKAFSNCYPYDVPDYASL

RSLVASSGTLEFITEGFTWTGVTQNGGSNACKRGPGSGFFSRLNWLTKSGSTYPVLNVTMPN

NDNFDKLYIWGVHHPSTNQEQTSLYVQASGRVTVSTRRSQQTIIPNIGSRPWVRGLSSRISI

YWTIVKPGDVLVINSNGNLIAPRGYFKMRTGKSSIMRSDAPIDTCISECITPNGSIPNDKPF

QNVNKITYGACPKYVKQNTLKLATGMRNVPEKQTRGLFGAIAGFIENGWEGMIDGWYGFRWQ

NSEGTGQAADLKSTQAAIDQINGILNRVIEKTNEKFHQIEKEFSEVEGRIQDLEKYVEDTKI

DLWSYNAELLVALINQHTIDLTDSEMNKLFEKTRRQLRENAEDMGNGCFKIYHKCDNACIES

IRNGTYDHDVYRDEALNNRFQIKGVSGSLPETGGGSHHHHHH

SEQ ID NO 51: UFV190068 (signal peptide and tag underlined)
MNTQILVFALMAIIPTNADKICLGHHAVSNGTKVNTLTERGVEVVNATETVERTNVPRICSK

GKRTVDLGQCGLLGTITGPPQCDQFLEFSADLIIERREGSDVCYPGKFVNEEALRQILRESG

GIDKETMGFTYSGIRTNGATSACRRSGSSFYAEMKWLLSNTDNAAFPQMTKSYKNTRKDPAL

IIWGIHHSGSTTEQTKLYGSGNKLITVGSSNYQQSFVPSPGARPQVNGQSGRIDFHWLILNP

NDTVTFSFNGAFIAPDRASFLRGKSMGIQSGVQVDANCEGDCYHSGGTIISNLPFQNINSRA

VGKCPRYVKQESLLLATGMKNVPEIPKGRGLFGAIAGFIENGWEGLIDGWYGFRWQNAQGEG

TAADYKSTQSAIDQITGILNRLIEKTNQQFELIDNEFTEVEKQIGNVINWTRDSMTEVWSYN

-continued

AELLVAMINQHTIDLADSEMNKLYERVKRQLRENAEEDGTGCFEIFHKCDDDCMASIRNNTY

DHSKYREEAMQNRIQIDPVSGSLPETGGGSHHHHHH

SEQ ID NO 52: UFV190841 (signal peptide and tag underlined)
MYKVVVIIALLGAVKGDRICLGHHAVANGTIVKTLTNEQEEVTNATETVESTNLNKLCMKGR

SYKDLGNCHPVGMLIGTPVCDPHLTGTWDTLIERENAIAHCYPGATINEEALRQKIMESGGI

SKMSTGFTYGSSINSAGTTKACMRNGGDSFYAELKWLVSKTKGQNFPQTTNTYRNTDTAEHL

IIWGIHHPSSTQEKNDLYGTQSLSISVESSTYQNNFVPVVGARPQVNGQSGRIDFHWTLVQP

GDNITFSHNGGLIAPSRVSKLTGRGLGIQSEALIDNSCESKCFWRGGSINTKLPFQNLSPRT

VGQCPKYVNQRSLLLATGMRNVPEVVQGRGLFGAIAGFIENGWEGMVDGWYGFRWQNAQGTG

QAADYKSTQAAIDQITGILNRLIEKTNTEFESIESEFSETEHQIGNVINWTKDSITDIWTYQ

AELLVAMINQHTIDMADSEMLNLYERVRKQLRQNAEEDGKGCFEIYHTCDDSCMESIRNNTY

DHSQYREEALLNRLNINSSGSLPETGGGSHHHHHH

The invention claimed is:

1. A recombinant influenza A hemagglutinin (HA) polypeptide, comprising an HA1 and a HA2 domain of an influenza A virus HA, and comprising an amino acid sequence wherein:
   (a) the amino acid at position 355 is W; and
   (b) the amino acid at position 432 is I and/or the amino acid at position 380 is I;
   and wherein the numbering of the amino acid positions in the amino acid sequence of the HA polypeptide is according to the numbering of amino acids in the amino acid sequence of HA from a reference H3N2 influenza strain, in particular the reference strain H3N2 A/Aichi/2/68 (SEQ ID NO: 1).

2. The HA polypeptide according to claim 1, comprising an amino acid sequence wherein:
   (a) the amino acid at position 388 is M; and/or
   (b) the amino acid at position 478 is I.

3. The HA polypeptide according to claim 1, wherein the polypeptide does not comprise a protease cleavage site between the HA1 and HA2 domain.

4. The HA polypeptide according to claim 1, wherein the HA1 and HA2 domain are from a Group 1 and/or a Group 2 influenza A virus.

5. The HA polypeptide according to claim 1, comprising a truncated HA1 and/or HA2 domain.

6. The HA polypeptide according to claim 5, wherein the transmembrane and intracytoplasmic domains have been deleted from the HA2 domain.

7. The HA polypeptide according to claim 5, wherein at least the C-terminal part of the HA2 domain starting with the amino acid corresponding to the amino acid at position 515 has been deleted.

8. The HA polypeptide according to claim 1, comprising a detecting and/or purification tag positioned C-terminal of the HA2 domain.

9. A multimeric polypeptide comprising at least two HA polypeptides according to claim 1.

10. A multimeric polypeptide according to claim 9, wherein the polypeptide is trimeric and comprises three HA polypeptides according claim 1.

11. A method for producing a recombinant HA polypeptide according to claim 1, comprising expressing a nucleic acid molecule encoding the HA polypeptide of claim 1 in a prokaryotic or eukaryotic cell, and isolating the HA polypeptide or fragment thereof from the cell.

12. An immunogenic composition comprising an HA polypeptide according to claim 1, and a pharmaceutically acceptable carrier.

13. A composition for inducing an immune response against an influenza virus, comprising the HA polypeptide according to claim 1.

14. An influenza virus vaccine composition comprising the HA polypeptide according to claim 1.

\* \* \* \* \*

SEQUENCE LISTING

<160> NUMBER OF SEQ ID NOS: 52

<210> SEQ ID NO 1
<211> LENGTH: 550
<212> TYPE: PRT
<213> ORGANISM: Artificial Sequence
<220> FEATURE:
<223> OTHER INFORMATION: CAA24269.1 haemagglutinin (Influenza A virus
      (A/Aichi/2/1968(H3N2) (excluding signal sequence)

<400> SEQUENCE: 1

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Ile His His Pro Ser Thr Asn Gln Glu Gln Thr
                180                 185                 190

Ser Leu Tyr Val Gln Ala Ser Gly Arg Val Thr Val Ser Thr Arg Arg
        195                 200                 205

-continued

```
Ser Gln Gln Thr Ile Ile Pro Asn Ile Gly Ser Arg Pro Trp Val Arg
    210             215             220

Gly Leu Ser Ser Arg Ile Ser Ile Tyr Trp Thr Ile Val Lys Pro Gly
225             230             235             240

Asp Val Leu Val Ile Asn Ser Asn Gly Asn Leu Ile Ala Pro Arg Gly
            245             250             255

Tyr Phe Lys Met Arg Thr Gly Lys Ser Ser Ile Met Arg Ser Asp Ala
            260             265             270

Pro Ile Asp Thr Cys Ile Ser Glu Cys Ile Thr Pro Asn Gly Ser Ile
            275             280             285

Pro Asn Asp Lys Pro Phe Gln Asn Val Asn Lys Ile Thr Tyr Gly Ala
    290             295             300

Cys Pro Lys Tyr Val Lys Gln Asn Thr Leu Lys Leu Ala Thr Gly Met
305             310             315             320

Arg Asn Val Pro Glu Lys Gln Thr Arg Gly Leu Phe Gly Ala Ile Ala
            325             330             335

Gly Phe Ile Glu Asn Gly Trp Glu Gly Met Ile Asp Gly Trp Tyr Gly
            340             345             350

Phe Arg His Gln Asn Ser Glu Gly Thr Gly Gln Ala Ala Asp Leu Lys
            355             360             365

Ser Thr Gln Ala Ala Ile Asp Gln Ile Asn Gly Lys Leu Asn Arg Val
    370             375             380

Ile Glu Lys Thr Asn Glu Lys Phe His Gln Ile Glu Lys Glu Phe Ser
385             390             395             400

Glu Val Glu Gly Arg Ile Gln Asp Leu Glu Lys Tyr Val Glu Asp Thr
            405             410             415

Lys Ile Asp Leu Trp Ser Tyr Asn Ala Glu Leu Leu Val Ala Leu Glu
            420             425             430

Asn Gln His Thr Ile Asp Leu Thr Asp Ser Glu Met Asn Lys Leu Phe
            435             440             445

Glu Lys Thr Arg Arg Gln Leu Arg Glu Asn Ala Glu Glu Met Gly Asn
    450             455             460

Gly Cys Phe Lys Ile Tyr His Lys Cys Asp Asn Ala Cys Ile Glu Ser
465             470             475             480

Ile Arg Asn Gly Thr Tyr Asp His Asp Val Tyr Arg Asp Glu Ala Leu
            485             490             495

Asn Asn Arg Phe Gln Ile Lys Gly Val Glu Leu Lys Ser Gly Tyr Lys
            500             505             510

Asp Trp Ile Leu Trp Ile Ser Phe Ala Ile Ser Cys Phe Leu Leu Cys
            515             520             525

Val Val Leu Leu Gly Phe Ile Met Trp Ala Cys Gln Arg Gly Asn Ile
    530             535             540

Arg Cys Asn Ile Cys Ile
545             550
```

```
<210> SEQ ID NO 2
<211> LENGTH: 121
<212> TYPE: PRT
<213> ORGANISM: Artificial Sequence
<220> FEATURE:
<223> OTHER INFORMATION: CR6261 VH

<400> SEQUENCE: 2

Glu Val Gln Leu Val Glu Ser Gly Ala Glu Val Lys Lys Pro Gly Ser
1               5               10              15
```

-continued

```
Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
            35                  40                  45

Gly Gly Ile Ile Pro Ile Phe Gly Thr Thr Lys Tyr Ala Pro Lys Phe
        50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120
```

<210> SEQ ID NO 3
<211> LENGTH: 111
<212> TYPE: PRT
<213> ORGANISM: Artificial Sequence
<220> FEATURE:
<223> OTHER INFORMATION: CR6261 VL

<400> SEQUENCE: 3

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asp
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
                85                  90                  95

Thr Ala Tyr Val Val Phe Gly Gly Gly Thr Lys Leu Thr Val Leu
            100                 105                 110
```

<210> SEQ ID NO 4
<211> LENGTH: 122
<212> TYPE: PRT
<213> ORGANISM: Artificial Sequence
<220> FEATURE:
<223> OTHER INFORMATION: CR8020 VH

<400> SEQUENCE: 4

```
Gln Val Gln Leu Gln Gln Ser Gly Ala Glu Val Lys Thr Pro Gly Ala
1               5                   10                  15

Ser Val Lys Val Ser Cys Lys Ala Ser Gly Tyr Thr Phe Thr Ser Phe
            20                  25                  30

Gly Val Ser Trp Ile Arg Gln Ala Pro Gly Gln Gly Leu Glu Trp Ile
            35                  40                  45

Gly Trp Ile Ser Ala Tyr Asn Gly Asp Thr Tyr Tyr Ala Gln Lys Phe
        50                  55                  60

Gln Ala Arg Val Thr Met Thr Thr Asp Thr Ser Thr Thr Thr Ala Tyr
65                  70                  75                  80

Met Glu Met Arg Ser Leu Arg Ser Asp Asp Thr Ala Val Tyr Tyr Cys
                85                  90                  95
```

Ala Arg Glu Pro Pro Leu Phe Tyr Ser Ser Trp Ser Leu Asp Asn Trp
            100                     105                 110

Gly Gln Gly Thr Leu Val Thr Val Ser Ser
        115                     120

<210> SEQ ID NO 5
<211> LENGTH: 108
<212> TYPE: PRT
<213> ORGANISM: Artificial Sequence
<220> FEATURE:
<223> OTHER INFORMATION: CR8020 VL

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Asn
            20                  25                  30

Tyr Leu Ala Trp Phe Gln Gln Lys Pro Gly Gln Ala Pro Arg Leu Leu
        35                  40                  45

Ile Tyr Gly Ala Ser Arg Arg Ala Thr Gly Ile Pro Asp Arg Ile Ser
    50                  55                  60

Gly Ser Gly Ser Gly Thr Asp Phe Thr Leu Thr Ile Ser Arg Leu Glu
65                  70                  75                  80

Pro Ala Asp Phe Ala Val Tyr Tyr Cys Gln Gln Tyr Gly Thr Ser Pro
                85                  90                  95

Arg Thr Phe Gly Gln Gly Ala Lys Val Glu Ile Lys
            100                 105

<210> SEQ ID NO 6
<211> LENGTH: 121
<212> TYPE: PRT
<213> ORGANISM: Artificial Sequence
<220> FEATURE:
<223> OTHER INFORMATION: CR9114 VH

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Ser Gly Met Asp Val Trp Gly
            100                 105                 110

Gln Gly Thr Thr Val Thr Val Ser Ser
        115                 120

<210> SEQ ID NO 7
<211> LENGTH: 110
<212> TYPE: PRT
<213> ORGANISM: Artificial Sequence
<220> FEATURE:
<223> OTHER INFORMATION: CR9114 VL -continued

<400> SEQUENCE: 7

```
Ser Tyr Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
            20                  25                  30

Ser Val Asn Trp Tyr Gln Gln Phe Pro Gly Thr Ala Pro Lys Leu Leu
        35                  40                  45

Ile Tyr Ser Asn Asp Gln Arg Pro Ser Val Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Lys Gly Ala Val Phe Gly Gly Gly Thr Gln Leu Thr Val Leu
            100                 105                 110
```

<210> SEQ ID NO 8
<211> LENGTH: 749
<212> TYPE: PRT
<213> ORGANISM: Artificial Sequence
<220> FEATURE:
<223> OTHER INFORMATION: MD3606

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Val Ser Ile Ser Ile Phe Asp Ile Tyr
            20                  25                  30

Ala Met Asp Trp Tyr Arg Gln Ala Pro Gly Lys Gln Arg Asp Leu Val
        35                  40                  45

Ala Thr Ser Phe Arg Asp Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Leu Cys His
                85                  90                  95

Val Ser Leu Tyr Arg Asp Pro Leu Gly Val Ala Gly Gly Met Gly Val
            100                 105                 110

Tyr Trp Gly Lys Gly Ala Leu Val Thr Val Ser Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Ala Gly Gly Ser Leu Lys Leu Ser Cys Ala Ala Ser Gly
145                 150                 155                 160

Arg Thr Tyr Ala Met Gly Trp Phe Arg Gln Ala Pro Gly Lys Glu Arg
                165                 170                 175

Glu Phe Val Ala His Ile Asn Ala Leu Gly Thr Arg Thr Tyr Tyr Ser
                180                 185                 190

Asp Ser Val Lys Gly Arg Phe Thr Ile Ser Arg Asp Asn Ala Lys Asn
            195                 200                 205

Thr Glu Tyr Leu Glu Met Asn Asn Leu Lys Pro Glu Asp Thr Ala Val
        210                 215                 220

Tyr Tyr Cys Thr Ala Gln Gly Gln Trp Arg Ala Ala Pro Val Ala Val
225                 230                 235                 240
```

-continued

```
Ala Ala Glu Tyr Glu Phe Trp Gly Gln Gly Thr Gln Val Thr Val Ser
                245                 250                 255

Ser Gly Gly Gly Gly Ser Gly Gly Gly Gly Ser Glu Val Gln Leu Val
                260                 265                 270

Glu Ser Gly Gly Gly Leu Val Gln Pro Gly Gly Ser Leu Arg Leu Ser
                275                 280                 285

Cys Ala Ala Thr Gly Phe Thr Leu Glu Asn Lys Ala Ile Gly Trp Phe
        290                 295                 300

Arg Gln Thr Pro Gly Ser Glu Arg Glu Gly Val Leu Cys Ile Ser Lys
305                 310                 315                 320

Ser Gly Ser Trp Thr Tyr Tyr Thr Asp Ser Met Arg Gly Arg Phe Thr
                325                 330                 335

Ile Ser Arg Asp Asn Ala Glu Asn Thr Val Tyr Leu Gln Met Asp Ser
                340                 345                 350

Leu Lys Pro Glu Asp Thr Ala Val Tyr Tyr Cys Ala Thr Thr Thr Ala
                355                 360                 365

Gly Gly Gly Leu Cys Trp Asp Gly Thr Thr Phe Ser Arg Leu Ala Ser
        370                 375                 380

Ser Trp Gly Gln Gly Thr Gln Val Thr Val Ser Ser Gly Gly Gly Gly
385                 390                 395                 400

Ser Gly Gly Gly Gly Ser Glu Val Gln Leu Val Glu Ser Gly Gly Gly
                405                 410                 415

Leu Val Gln Pro Gly Gly Ser Leu Lys Leu Ser Cys Ala Ala Ser Gly
                420                 425                 430

Phe Thr Phe Ser Thr Ser Trp Met Tyr Trp Leu Arg Gln Ala Pro Gly
        435                 440                 445

Lys Gly Leu Glu Trp Val Ser Val Ile Asn Thr Asp Gly Gly Thr Tyr
        450                 455                 460

Tyr Ala Asp Ser Val Lys Asp Arg Phe Thr Ile Ser Arg Asp Asn Ala
465                 470                 475                 480

Lys Asp Thr Leu Tyr Leu Gln Met Ser Ser Leu Lys Ser Glu Asp Thr
                485                 490                 495

Ala Val Tyr Tyr Cys Ala Lys Asp Trp Gly Gly Pro Glu Pro Thr Arg
                500                 505                 510

Gly Gln Gly Thr Gln Val Thr Val Ser Ser Asp Lys Thr His Thr Cys
        515                 520                 525

Pro Pro Cys Pro Ala Pro Glu Leu Leu Gly Gly Pro Ser Val Phe Leu
        530                 535                 540

Phe Pro Pro Lys Pro Lys Asp Thr Leu Met Ile Ser Arg Thr Pro Glu
545                 550                 555                 560

Val Thr Cys Val Val Val Asp Val Ser His Glu Asp Pro Glu Val Lys
                565                 570                 575

Phe Asn Trp Tyr Val Asp Gly Val Glu Val His Asn Ala Lys Thr Lys
                580                 585                 590

Pro Arg Glu Glu Gln Tyr Asn Ser Thr Tyr Arg Val Val Ser Val Leu
                595                 600                 605

Thr Val Leu His Gln Asp Trp Leu Asn Gly Lys Glu Tyr Lys Cys Lys
        610                 615                 620

Val Ser Asn Lys Ala Leu Pro Ala Pro Ile Glu Lys Thr Ile Ser Lys
625                 630                 635                 640

Ala Lys Gly Gln Pro Arg Glu Pro Gln Val Tyr Thr Leu Pro Pro Ser
                645                 650                 655

Arg Glu Glu Met Thr Lys Asn Gln Val Ser Leu Thr Cys Leu Val Lys
```

```
                660                    665                       670

Gly Phe Tyr Pro Ser Asp Ile Ala Val Glu Trp Glu Ser Asn Gly Gln
            675                    680                    685

Pro Glu Asn Asn Tyr Lys Thr Thr Pro Pro Val Leu Asp Ser Asp Gly
        690                    695                    700

Ser Phe Phe Leu Tyr Ser Lys Leu Thr Val Asp Lys Ser Arg Trp Gln
705                    710                    715                    720

Gln Gly Asn Val Phe Ser Cys Ser Val Met His Glu Ala Leu His Asn
                725                    730                    735

His Tyr Thr Gln Lys Ser Leu Ser Leu Ser Pro Gly Lys
            740                    745
```

```
<210> SEQ ID NO 9
<211> LENGTH: 526
<212> TYPE: PRT
<213> ORGANISM: Artificial Sequence
<220> FEATURE:
<223> OTHER INFORMATION: UFV181157

<400> SEQUENCE: 9

Met Lys Ala Ile Leu Val Val Leu Leu Tyr Thr Phe Ala Thr Ala Asn
1                   5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
```

-continued

```
                    275                 280                 285
        Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
        305                 310                 315                 320

Pro Lys Tyr Val Lys Ser Thr Lys Leu Arg Leu Ala Thr Gly Leu Arg
                        325                 330                 335

Asn Ile Pro Ser Ile Gln Ser Arg Gly Leu Phe Gly Ala Ile Ala Gly
                    340                 345                 350

Phe Ile Glu Gly Gly Trp Thr Gly Met Val Asp Gly Trp Tyr Gly Tyr
                    355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
        385                 390                 395                 400

Glu Lys Met Asn Thr Gln Phe Thr Ala Val Gly Lys Glu Phe Asn His
                        405                 410                 415

Leu Glu Lys Arg Ile Glu Asn Leu Asn Lys Lys Val Asp Asp Gly Phe
                        420                 425                 430

Leu Asp Ile Trp Thr Tyr Asn Ala Glu Leu Leu Val Leu Leu Glu Asn
                        435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
        465                 470                 475                 480

Cys Phe Glu Phe Tyr His Lys Cys Asp Asn Thr Cys Met Glu Ser Val
                        485                 490                 495

Lys Asn Gly Thr Tyr Asp Tyr Pro Lys Tyr Ser Glu Glu Ala Lys Leu
                    500                 505                 510

Asn Arg Glu Glu Ile Asp Gly Ser His His His His His
            515                 520                 525
```

<210> SEQ ID NO 10
<211> LENGTH: 535
<212> TYPE: PRT
<213> ORGANISM: Artificial Sequence
<220> FEATURE:
<223> OTHER INFORMATION: UFV181009

<400> SEQUENCE: 10

```
        Met Lys Ala Ile Leu Val Val Leu Leu Tyr Thr Phe Ala Thr Ala Asn
        1               5                   10                  15

Ala Asp Thr Leu Cys Ile Gly Tyr His Ala Asn Asn Ser Thr Asp Thr
                    20                  25                  30

Val Asp Thr Val Leu Glu Lys Asn Val Thr Val Thr His Ser Val Asn
                    35                  40                  45

Leu Leu Glu Asp Lys His Asn Gly Lys Leu Cys Lys Leu Arg Gly Val
            50                  55                  60

Ala Pro Leu His Leu Gly Lys Cys Asn Ile Ala Gly Trp Ile Leu Gly
        65                  70                  75                  80

Asn Pro Glu Cys Glu Ser Leu Ser Thr Ala Ser Ser Trp Ser Tyr Ile
                        85                  90                  95

Val Glu Thr Pro Ser Ser Asp Asn Gly Thr Cys Tyr Pro Gly Asp Phe
                    100                 105                 110

Ile Asp Tyr Glu Glu Leu Arg Glu Gln Leu Ser Ser Val Ser Ser Phe
```

-continued

```
             115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ser Ala Asp Gln Gln Ser Leu
                195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
                275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His Trp Gln Asn Glu Gln Gly Ser Gly Tyr Ala Ala Asp Leu Lys Ser
    370                 375                 380

Thr Gln Asn Ala Ile Asp Glu Ile Thr Asn Ile Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Ile Asn
                435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Ile Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Ser Gly Ser Leu Pro Glu Thr Gly Gly Gly
    515                 520                 525

Ser His His His His His His
    530                 535
```

```
<210> SEQ ID NO 11
<211> LENGTH: 526
<212> TYPE: PRT
<213> ORGANISM: Artificial Sequence
<220> FEATURE:
<223> OTHER INFORMATION: UFV181134

<400> SEQUENCE: 11

Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Asn Gln Ser Tyr Ile Asn Asp Lys Gly Lys Glu Val Leu Val
            180                 185                 190

Leu Trp Gly Ile His His Pro Ser Thr Thr Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Thr Met Glu Arg Asn Ala Gly Ser Gly Ile Ile Ile Ser Asp Thr Pro
        275                 280                 285

Val His Asp Cys Asn Thr Thr Cys Gln Thr Pro Glu Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365
```

His His Gln Asn Glu Gln Gly Ser Gly Tyr Ala Ala Asp Leu Lys Ser
    370             375             380

Thr Gln Asn Ala Ile Asp Lys Ile Thr Asn Lys Val Asn Ser Val Ile
385             390             395             400

Glu Lys Met Asn Thr Gln Phe Thr Ala Val Gly Lys Glu Phe Asn His
            405             410             415

Leu Glu Lys Arg Ile Glu Asn Leu Asn Lys Lys Val Asp Asp Gly Phe
            420             425             430

Leu Asp Ile Trp Thr Tyr Asn Ala Glu Leu Leu Val Leu Leu Glu Asn
        435             440             445

Glu Arg Thr Leu Asp Tyr His Asp Ser Asn Val Lys Asn Leu Tyr Glu
    450             455             460

Lys Val Arg Asn Gln Leu Lys Asn Asn Ala Lys Glu Ile Gly Asn Gly
465             470             475             480

Cys Phe Glu Phe Tyr His Lys Cys Asp Asn Thr Cys Met Glu Ser Val
            485             490             495

Lys Asn Gly Thr Tyr Asp Tyr Pro Lys Tyr Ser Glu Glu Ala Lys Leu
            500             505             510

Asn Arg Glu Lys Ile Asp Gly Ser His His His His His His
        515             520             525

<210> SEQ ID NO 12
<211> LENGTH: 535
<212> TYPE: PRT
<213> ORGANISM: Artificial Sequence
<220> FEATURE:
<223> OTHER INFORMATION: UFV181091

<400> SEQUENCE: 12

Met Lys Ala Ile Leu Val Val Leu Leu Tyr Thr Phe Thr Thr Ala Asn
1               5               10              15

Ala Asp Thr Leu Cys Ile Gly Tyr His Ala Asn Asn Ser Thr Asp Thr
            20              25              30

Val Asp Thr Val Leu Glu Lys Asn Val Thr Val Thr His Ser Val Asn
        35              40              45

Leu Leu Glu Asp Lys His Asn Gly Lys Leu Cys Lys Leu Arg Gly Val
    50              55              60

Ala Pro Leu His Leu Gly Lys Cys Asn Ile Ala Gly Trp Ile Leu Gly
65              70              75              80

Asn Pro Glu Cys Glu Ser Leu Ser Thr Ala Ser Ser Trp Ser Tyr Ile
            85              90              95

Val Glu Thr Ser Asn Ser Asp Asn Gly Thr Cys Tyr Pro Gly Asp Phe
            100             105             110

Ile Asn Tyr Glu Glu Leu Arg Glu Gln Leu Ser Ser Val Ser Ser Phe
        115             120             125

Glu Arg Phe Glu Ile Phe Pro Lys Thr Ser Ser Trp Pro Asn His Asp
    130             135             140

Ser Asn Lys Gly Val Thr Ala Ala Cys Pro His Ala Gly Ala Lys Ser
145             150             155             160

Phe Tyr Lys Asn Leu Ile Trp Leu Val Lys Lys Gly Asn Ser Tyr Pro
            165             170             175

Lys Leu Asn Gln Ser Tyr Ile Asn Asp Lys Gly Lys Glu Val Leu Val
        180             185             190

Leu Trp Gly Ile His His Pro Ser Thr Thr Ala Asp Gln Gln Ser Leu
    195             200             205

```
Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Thr Met Glu Arg Asn Ala Gly Ser Gly Ile Ile Ile Ser Asp Thr Pro
                275                 280                 285

Val His Asp Cys Asn Thr Thr Cys Gln Thr Pro Glu Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His Trp Gln Asn Glu Gln Gly Ser Gly Tyr Ala Ala Asp Leu Lys Ser
    370                 375                 380

Thr Gln Asn Ala Ile Asp Lys Ile Thr Asn Ile Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Ile Asn
                435                 440                 445

Glu Arg Thr Leu Asp Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Ile Glu Ser Val
                485                 490                 495

Lys Asn Gly Thr Tyr Asp Tyr Pro Lys Tyr Ser Glu Glu Ala Lys Leu
                500                 505                 510

Asn Arg Glu Lys Ile Asp Ser Gly Ser Leu Pro Glu Thr Gly Gly Gly
    515                 520                 525

Ser His His His His His His
    530                 535
```

```
<210> SEQ ID NO 13
<211> LENGTH: 522
<212> TYPE: PRT
<213> ORGANISM: Artificial Sequence
<220> FEATURE:
<223> OTHER INFORMATION: UFV181153

<400> SEQUENCE: 13

Met Ala Ile Ile Tyr Leu Ile Leu Leu Phe Ala Ala Val Arg Gly Asp
1               5                   10                  15

Gln Ile Cys Ile Gly Tyr His Ser Asn Asn Ser Thr Glu Lys Val Asp
                20                  25                  30
```

-continued

```
Thr Ile Leu Glu Arg Asn Val Thr Val Thr His Ala Gln Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Thr Val Pro Glu Trp Ser Tyr Ile Met Glu
                85                  90                  95

Lys Glu Asn Pro Arg Asn Gly Leu Cys Tyr Pro Gly Ser Phe Asn Asp
                100                 105                 110

Tyr Glu Glu Leu Lys His Leu Leu Ser Ser Val Thr His Phe Glu Lys
        115                 120                 125

Val Lys Ile Leu Pro Arg Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Ile Ala Lys Gly
                165                 170                 175

Ser Tyr Asn Asn Thr Ser Gly Glu Gln Met Leu Ile Ile Trp Gly Val
        180                 185                 190

His His Pro Asn Asp Asp Ala Glu Gln Arg Thr Leu Tyr Gln Asn Val
        195                 200                 205

Gly Thr Tyr Val Ser Val Gly Thr Ser Thr Leu Asn Lys Arg Ser Val
    210                 215                 220

Pro Glu Ile Ala Thr Arg Pro Lys Val Asn Gly Gln Gly Gly Arg Met
225                 230                 235                 240

Glu Phe Ser Trp Thr Ile Leu Asp Met Leu Asp Thr Ile Asn Phe Glu
                245                 250                 255

Ser Thr Gly Asn Leu Ile Ala Pro Glu Tyr Gly Phe Arg Ile Ser Lys
                260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Ile His Pro Leu Thr Ile Gly Glu Cys Pro Lys Tyr Val
305                 310                 315                 320

Lys Ser Glu Arg Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
                340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Arg Ala
        370                 375                 380

Ile Asp Gly Ile Thr Asn Lys Val Asn Ser Val Ile Glu Lys Met Asn
385                 390                 395                 400

Thr Gln Phe Glu Ala Val Gly Lys Glu Phe Asn Asn Leu Glu Lys Arg
                405                 410                 415

Leu Glu Asn Leu Asn Lys Lys Met Glu Asp Gly Phe Leu Asp Val Trp
        420                 425                 430

Thr Tyr Asn Ala Glu Leu Leu Val Leu Met Glu Asn Glu Arg Thr Leu
        435                 440                 445
```

-continued

```
Asp Phe His Asp Ser Asn Val Lys Asn Leu Tyr Asp Lys Val Arg Met
    450             455             460

Gln Leu Arg Asp Asn Ala Lys Glu Leu Gly Asn Gly Cys Phe Glu Phe
465             470             475             480

Tyr His Lys Cys Asp Asp Glu Cys Met Asn Ser Val Lys Asn Gly Thr
                485             490             495

Tyr Asp Tyr Pro Lys Tyr Glu Glu Glu Ser Lys Leu Asn Arg Asn Glu
            500             505             510

Ile Lys Gly Ser His His His His His His
        515             520
```

```
<210> SEQ ID NO 14
<211> LENGTH: 531
<212> TYPE: PRT
<213> ORGANISM: Artificial Sequence
<220> FEATURE:
<223> OTHER INFORMATION: UFV181154

<400> SEQUENCE: 14
```

```
Met Ala Ile Ile Tyr Leu Ile Leu Leu Phe Ala Ala Val Arg Gly Asp
1               5               10              15

Gln Ile Cys Ile Gly Tyr His Ser Asn Asn Ser Thr Glu Lys Val Asp
            20              25              30

Thr Ile Leu Glu Arg Asn Val Thr Val Thr His Ala Gln Asp Ile Leu
        35              40              45

Glu Lys Thr His Asn Gly Lys Leu Cys Lys Leu Asn Gly Ile Pro Pro
    50              55              60

Leu Glu Leu Gly Asp Cys Ser Ile Ala Gly Trp Leu Leu Gly Asn Pro
65              70              75              80

Glu Cys Asp Arg Leu Leu Thr Val Pro Glu Trp Ser Tyr Ile Met Glu
                85              90              95

Lys Glu Asn Pro Arg Asn Gly Leu Cys Tyr Pro Gly Ser Phe Asn Asp
            100             105             110

Tyr Glu Glu Leu Lys His Leu Leu Ser Ser Val Thr His Phe Glu Lys
        115             120             125

Val Lys Ile Leu Pro Arg Asp Arg Trp Thr Gln His Thr Thr Thr Gly
    130             135             140

Gly Ser Arg Ala Cys Ala Val Ser Gly Asn Pro Ser Phe Phe Arg Asn
145             150             155             160

Met Val Trp Leu Thr Lys Lys Gly Ser Asn Tyr Pro Ile Ala Lys Gly
                165             170             175

Ser Tyr Asn Asn Thr Ser Gly Glu Gln Met Leu Ile Ile Trp Gly Val
            180             185             190

His His Pro Asn Asp Asp Ala Glu Gln Arg Thr Leu Tyr Gln Asn Val
        195             200             205

Gly Thr Tyr Val Ser Val Gly Thr Ser Thr Leu Asn Lys Arg Ser Val
    210             215             220

Pro Glu Ile Ala Thr Arg Pro Lys Val Asn Gly Gln Gly Gly Arg Met
225             230             235             240

Glu Phe Ser Trp Thr Ile Leu Asp Met Leu Asp Thr Ile Asn Phe Glu
                245             250             255

Ser Thr Gly Asn Leu Ile Ala Pro Glu Tyr Gly Phe Arg Ile Ser Lys
            260             265             270

Arg Gly Ser Ser Gly Ile Met Lys Thr Glu Gly Thr Leu Glu Asn Cys
        275             280             285
```

-continued

```
Glu Thr Lys Cys Gln Thr Pro Leu Gly Ala Ile Asn Thr Thr Leu Pro
    290                 295                 300

Phe His Asn Ile His Pro Leu Thr Ile Gly Glu Cys Pro Lys Tyr Val
305                 310                 315                 320

Lys Ser Glu Arg Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
                340                 345                 350

Gly Trp Gln Gly Met Val Asp Gly Trp Tyr Gly Tyr His Trp Ser Asn
            355                 360                 365

Asp Gln Gly Ser Gly Tyr Ala Ala Asp Lys Glu Ser Thr Gln Arg Ala
    370                 375                 380

Ile Asp Gly Ile Thr Asn Ile Val Asn Ser Val Ile Glu Lys Met Asn
385                 390                 395                 400

Thr Gln Phe Glu Ala Val Gly Lys Glu Phe Asn Asn Leu Glu Lys Arg
                405                 410                 415

Leu Glu Asn Leu Asn Lys Lys Met Glu Asp Gly Phe Leu Asp Val Trp
                420                 425                 430

Thr Tyr Asn Ala Glu Leu Leu Val Leu Met Ile Asn Glu Arg Thr Leu
            435                 440                 445

Asp Phe His Asp Ser Asn Val Lys Asn Leu Tyr Asp Lys Val Arg Met
    450                 455                 460

Gln Leu Arg Asp Asn Ala Lys Glu Leu Gly Asn Gly Cys Phe Glu Phe
465                 470                 475                 480

Tyr His Lys Cys Asp Asp Glu Cys Ile Asn Ser Val Lys Asn Gly Thr
                485                 490                 495

Tyr Asp Tyr Pro Lys Tyr Glu Glu Glu Ser Lys Leu Asn Arg Asn Glu
                500                 505                 510

Ile Lys Ser Gly Ser Leu Pro Glu Thr Gly Gly Gly Ser His His His
            515                 520                 525

His His His
    530

<210> SEQ ID NO 15
<211> LENGTH: 524
<212> TYPE: PRT
<213> ORGANISM: Artificial Sequence
<220> FEATURE:
<223> OTHER INFORMATION: UFV181158

<400> SEQUENCE: 15

Met Glu Lys Ile Val Leu Leu Phe Ala Ile Val Ser Leu Val Gln Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Ser Pro Ile Asn Gly Leu Cys Tyr Pro Gly Asp Phe Asn
                100                 105                 110
```

-continued

```
Asp Tyr Glu Glu Leu Lys His Leu Leu Ser Ser Thr Asn His Phe Glu
        115                 120                 125

Lys Ile Gln Ile Ile Pro Arg Ser Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Val Ser Val Gly Thr Ser Thr Leu Asn Gln Arg
    210                 215                 220

Ser Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Gly Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Val
            325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr Leu His
        355                 360                 365

Ser Asn Glu Gln Gly Ser Gly Tyr Ala Ala Asp Lys Glu Ser Thr Gln
    370                 375                 380

Lys Ala Ile Asp Gly Ile Thr Asn Lys Ile Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asp Glu Cys Met Glu Ser Val Arg Asn
                485                 490                 495

Gly Thr Tyr Asp Tyr Pro Gln Tyr Ser Glu Glu Ala Arg Leu Asn Arg
            500                 505                 510

Glu Glu Ile Ser Gly Ser His His His His His
            515                 520
```

-continued

```
<210> SEQ ID NO 16
<211> LENGTH: 533
<212> TYPE: PRT
<213> ORGANISM: Artificial Sequence
<220> FEATURE:
<223> OTHER INFORMATION: UFV181159

<400> SEQUENCE: 16

Met Glu Lys Ile Val Leu Leu Phe Ala Ile Val Ser Leu Val Gln Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Ser Pro Ile Asn Gly Leu Cys Tyr Pro Gly Asp Phe Asn
            100                 105                 110

Asp Tyr Glu Glu Leu Lys His Leu Leu Ser Ser Thr Asn His Phe Glu
        115                 120                 125

Lys Ile Gln Ile Ile Pro Arg Ser Ser Trp Ser Asn His Asp Ala Ser
        130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Val Ser Val Gly Thr Ser Thr Leu Asn Gln Arg
        210                 215                 220

Ser Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Gly Leu Glu Tyr Gly
            275                 280                 285

Asn Cys Asn Thr Lys Cys Gln Thr Pro Met Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr Leu Trp
            355                 360                 365

Ser Asn Glu Gln Gly Ser Gly Tyr Ala Ala Asp Lys Glu Ser Thr Gln
```

-continued

```
        370             375             380
Lys Ala Ile Asp Gly Ile Thr Asn Ile Ile Asn Ser Ile Ile Asp Lys
385                 390             395                 400

Met Asn Thr Gln Phe Glu Ala Val Gly Lys Glu Phe Asn Asn Leu Glu
                405             410             415

Arg Arg Ile Glu Asn Leu Asn Lys Lys Met Glu Asp Gly Phe Leu Asp
            420             425             430

Val Trp Thr Tyr Asn Ala Glu Leu Leu Val Leu Met Ile Asn Glu Arg
        435             440             445

Thr Leu Asp Phe His Asp Ser Asn Val Lys Asn Leu Tyr Asp Lys Val
    450             455             460

Arg Leu Gln Leu Arg Asp Asn Ala Lys Glu Leu Gly Asn Gly Cys Phe
465             470             475             480

Glu Phe Tyr His Lys Cys Asp Asp Glu Cys Ile Glu Ser Val Arg Asn
                485             490             495

Gly Thr Tyr Asp Tyr Pro Gln Tyr Ser Glu Glu Ala Arg Leu Asn Arg
            500             505             510

Glu Glu Ile Ser Ser Gly Ser Leu Pro Glu Thr Gly Gly Gly Ser His
        515             520             525

His His His His His
    530
```

<210> SEQ ID NO 17
<211> LENGTH: 520
<212> TYPE: PRT
<213> ORGANISM: Artificial Sequence
<220> FEATURE:
<223> OTHER INFORMATION: UFV181155

<400> SEQUENCE: 17

```
Met Glu Thr Ile Ser Leu Ile Thr Ile Leu Leu Val Val Thr Ala Ser
1               5               10              15

Asn Ala Asp Lys Ile Cys Ile Gly His Gln Ser Thr Asn Ser Thr Glu
            20              25              30

Thr Val Asp Thr Leu Thr Glu Thr Asn Val Pro Val Thr His Ala Lys
        35              40              45

Glu Leu Leu His Thr Glu His Asn Gly Met Leu Cys Ala Thr Ser Leu
    50              55              60

Gly His Pro Leu Ile Leu Asp Thr Cys Thr Ile Glu Gly Leu Val Tyr
65              70              75              80

Gly Asn Pro Ser Cys Asp Leu Leu Leu Gly Gly Arg Glu Trp Ser Tyr
                85              90              95

Ile Val Glu Arg Ser Ser Ala Val Asn Gly Thr Cys Tyr Pro Gly Asn
            100             105             110

Val Glu Asn Leu Glu Glu Leu Arg Thr Leu Phe Ser Ser Ala Ser Ser
        115             120             125

Tyr Gln Arg Ile Gln Ile Phe Pro Asp Thr Thr Trp Asn Val Thr Tyr
    130             135             140

Thr Gly Thr Ser Arg Ala Cys Ser Gly Ser Phe Tyr Arg Ser Met Arg
145             150             155             160

Trp Leu Thr Gln Lys Ser Gly Phe Tyr Pro Val Gln Asp Ala Gln Tyr
                165             170             175

Thr Asn Asn Arg Gly Lys Ser Ile Leu Phe Val Trp Gly Ile His His
            180             185             190

Pro Pro Thr Tyr Thr Glu Gln Thr Asn Leu Tyr Ile Arg Asn Asp Thr
```

-continued

```
              195                 200                 205
Thr Thr Ser Val Thr Thr Glu Asp Leu Asn Arg Thr Phe Lys Pro Val
    210                 215                 220
Ile Gly Pro Arg Pro Leu Val Asn Gly Leu Gln Gly Arg Ile Asp Tyr
225                 230                 235                 240
Tyr Trp Ser Val Leu Lys Pro Gly Gln Thr Leu Arg Val Arg Ser Asn
                245                 250                 255
Gly Asn Leu Ile Ala Pro Trp Tyr Gly His Val Leu Ser Gly Gly Ser
                260                 265                 270
His Gly Arg Ile Leu Lys Thr Asp Leu Lys Gly Gly Asn Cys Val Val
                275                 280                 285
Gln Cys Gln Thr Glu Lys Gly Gly Leu Asn Ser Thr Leu Pro Phe His
    290                 295                 300
Asn Ile Ser Lys Tyr Ala Phe Gly Thr Cys Pro Lys Tyr Val Arg Val
305                 310                 315                 320
Asn Ser Leu Lys Leu Ala Val Gly Leu Arg Asn Val Pro Ala Arg Ser
                325                 330                 335
Ser Arg Gly Leu Phe Gly Ala Ile Ala Gly Phe Ile Glu Gly Gly Trp
                340                 345                 350
Pro Gly Leu Val Ala Gly Trp Tyr Gly Phe Gln His Ser Asn Asp Gln
                355                 360                 365
Gly Val Gly Met Ala Ala Asp Arg Asp Ser Thr Gln Lys Ala Ile Asp
    370                 375                 380
Lys Ile Thr Ser Lys Val Asn Asn Ile Val Asp Lys Met Asn Lys Gln
385                 390                 395                 400
Tyr Glu Ile Ile Asp His Glu Phe Ser Glu Val Glu Thr Arg Leu Asn
                405                 410                 415
Met Ile Asn Asn Lys Ile Asp Asp Gln Ile Gln Asp Val Trp Ala Tyr
                420                 425                 430
Asn Ala Glu Leu Leu Val Leu Leu Glu Asn Gln Lys Thr Leu Asp Glu
                435                 440                 445
His Asp Ala Asn Val Asn Asn Leu Tyr Asn Lys Val Lys Arg Ala Leu
    450                 455                 460
Gly Ser Asn Ala Met Glu Asp Gly Lys Gly Cys Phe Glu Leu Tyr His
465                 470                 475                 480
Lys Cys Asp Asp Gln Cys Met Glu Thr Ile Arg Asn Gly Thr Tyr Asn
                485                 490                 495
Arg Arg Lys Tyr Arg Glu Glu Ser Arg Leu Glu Arg Gln Lys Ile Glu
                500                 505                 510
Gly Ser His His His His His His
        515                 520
```

<210> SEQ ID NO 18
<211> LENGTH: 529
<212> TYPE: PRT
<213> ORGANISM: Artificial Sequence
<220> FEATURE:
<223> OTHER INFORMATION: UFV181156

<400> SEQUENCE: 18

```
Met Glu Thr Ile Ser Leu Ile Thr Ile Leu Leu Val Val Thr Ala Ser
1               5                   10                  15
Asn Ala Asp Lys Ile Cys Ile Gly His Gln Ser Thr Asn Ser Thr Glu
                20                  25                  30
Thr Val Asp Thr Leu Thr Glu Thr Asn Val Pro Val Thr His Ala Lys
```

-continued

```
             35                    40                    45
Glu Leu Leu His Thr Glu His Asn Gly Met Leu Cys Ala Thr Ser Leu
    50                    55                    60
Gly His Pro Leu Ile Leu Asp Thr Cys Thr Ile Glu Gly Leu Val Tyr
65                    70                    75                    80
Gly Asn Pro Ser Cys Asp Leu Leu Leu Gly Gly Arg Glu Trp Ser Tyr
                85                    90                    95
Ile Val Glu Arg Ser Ser Ala Val Asn Gly Thr Cys Tyr Pro Gly Asn
                100                   105                   110
Val Glu Asn Leu Glu Glu Leu Arg Thr Leu Phe Ser Ser Ala Ser Ser
                115                   120                   125
Tyr Gln Arg Ile Gln Ile Phe Pro Asp Thr Thr Trp Asn Val Thr Tyr
    130                   135                   140
Thr Gly Thr Ser Arg Ala Cys Ser Gly Ser Phe Tyr Arg Ser Met Arg
145                   150                   155                   160
Trp Leu Thr Gln Lys Ser Gly Phe Tyr Pro Val Gln Asp Ala Gln Tyr
                165                   170                   175
Thr Asn Asn Arg Gly Lys Ser Ile Leu Phe Val Trp Gly Ile His His
                180                   185                   190
Pro Pro Thr Tyr Thr Glu Gln Thr Asn Leu Tyr Ile Arg Asn Asp Thr
                195                   200                   205
Thr Thr Ser Val Thr Thr Glu Asp Leu Asn Arg Thr Phe Lys Pro Val
    210                   215                   220
Ile Gly Pro Arg Pro Leu Val Asn Gly Leu Gln Gly Arg Ile Asp Tyr
225                   230                   235                   240
Tyr Trp Ser Val Leu Lys Pro Gly Gln Thr Leu Arg Val Arg Ser Asn
                245                   250                   255
Gly Asn Leu Ile Ala Pro Trp Tyr Gly His Val Leu Ser Gly Gly Ser
                260                   265                   270
His Gly Arg Ile Leu Lys Thr Asp Leu Lys Gly Gly Asn Cys Val Val
                275                   280                   285
Gln Cys Gln Thr Glu Lys Gly Gly Leu Asn Ser Thr Leu Pro Phe His
    290                   295                   300
Asn Ile Ser Lys Tyr Ala Phe Gly Thr Cys Pro Lys Tyr Val Arg Val
305                   310                   315                   320
Asn Ser Leu Lys Leu Ala Val Gly Leu Arg Asn Val Pro Ala Arg Ser
                325                   330                   335
Ser Arg Gly Leu Phe Gly Ala Ile Ala Gly Phe Ile Glu Gly Gly Trp
                340                   345                   350
Pro Gly Leu Val Ala Gly Trp Tyr Gly Phe Gln Trp Ser Asn Asp Gln
                355                   360                   365
Gly Val Gly Met Ala Ala Asp Arg Asp Ser Thr Gln Lys Ala Ile Asp
    370                   375                   380
Lys Ile Thr Ser Ile Val Asn Asn Ile Val Asp Lys Met Asn Lys Gln
385                   390                   395                   400
Tyr Glu Ile Ile Asp His Glu Phe Ser Glu Val Glu Thr Arg Leu Asn
                405                   410                   415
Met Ile Asn Asn Lys Ile Asp Asp Gln Ile Gln Asp Val Trp Ala Tyr
                420                   425                   430
Asn Ala Glu Leu Leu Val Leu Leu Ile Asn Gln Lys Thr Leu Asp Glu
    435                   440                   445
His Asp Ala Asn Val Asn Asn Leu Tyr Asn Lys Val Lys Arg Ala Leu
    450                   455                   460
```

-continued

```
Gly Ser Asn Ala Met Glu Asp Gly Lys Gly Cys Phe Glu Leu Tyr His
465                 470             475             480

Lys Cys Asp Asp Gln Cys Ile Glu Thr Ile Arg Asn Gly Thr Tyr Asn
                485             490             495

Arg Arg Lys Tyr Arg Glu Glu Ser Arg Leu Glu Arg Gln Lys Ile Glu
            500             505             510

Ser Gly Ser Leu Pro Glu Thr Gly Gly Gly Ser His His His His His
        515             520             525

His

<210> SEQ ID NO 19
<211> LENGTH: 529
<212> TYPE: PRT
<213> ORGANISM: Artificial Sequence
<220> FEATURE:
<223> OTHER INFORMATION: UFV181141

<400> SEQUENCE: 19

Met Lys Thr Ile Ile Ala Leu Ser Tyr Ile Phe Cys Leu Ala Leu Gly
1               5               10              15

Gln Asp Leu Pro Gly Asn Asp Asn Ser Thr Ala Thr Leu Cys Leu Gly
            20              25              30

His His Ala Val Pro Asn Gly Thr Leu Val Lys Thr Ile Thr Asp Asp
        35              40              45

Gln Ile Glu Val Thr Asn Ala Thr Glu Leu Val Gln Ser Ser Ser Thr
    50              55              60

Gly Lys Ile Cys Asn Asn Pro His Arg Ile Leu Asp Gly Ile Asp Cys
65              70              75              80

Thr Leu Ile Asp Ala Leu Leu Gly Asp Pro His Cys Asp Val Phe Gln
                85              90              95

Asn Glu Thr Trp Asp Leu Phe Val Glu Arg Ser Lys Ala Phe Ser Asn
            100             105             110

Cys Tyr Pro Tyr Asp Val Pro Asp Tyr Ala Ser Leu Arg Ser Leu Val
            115             120             125

Ala Ser Ser Gly Thr Leu Glu Phe Ile Thr Glu Gly Phe Thr Trp Thr
        130             135             140

Gly Val Thr Gln Asn Gly Gly Ser Asn Ala Cys Lys Arg Gly Pro Gly
145             150             155             160

Ser Gly Phe Phe Ser Arg Leu Asn Trp Leu Thr Lys Ser Gly Ser Thr
                165             170             175

Tyr Pro Val Leu Asn Val Thr Met Pro Asn Asn Asp Asn Phe Asp Lys
            180             185             190

Leu Tyr Ile Trp Gly Val His His Pro Ser Thr Asn Gln Glu Gln Thr
            195             200             205

Ser Leu Tyr Val Gln Ala Ser Gly Arg Val Thr Val Ser Thr Arg Arg
    210             215             220

Ser Gln Gln Thr Ile Ile Pro Asn Ile Gly Ser Arg Pro Trp Val Arg
225             230             235             240

Gly Leu Ser Ser Arg Ile Ser Ile Tyr Trp Thr Ile Val Lys Pro Gly
                245             250             255

Asp Val Leu Val Ile Asn Ser Asn Gly Asn Leu Ile Ala Pro Arg Gly
            260             265             270

Tyr Phe Lys Met Arg Thr Gly Lys Ser Ser Ile Met Arg Ser Asp Ala
            275             280             285
```

```
Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
                340                 345                 350

Gly Phe Ile Glu Asn Gly Trp Glu Gly Met Ile Asp Gly Trp Tyr Gly
            355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Gly Ser His His His His
            515                 520                 525

His
```

```
<210> SEQ ID NO 20
<211> LENGTH: 538
<212> TYPE: PRT
<213> ORGANISM: Artificial Sequence
<220> FEATURE:
<223> OTHER INFORMATION: UFV180660

<400> SEQUENCE: 20
```

```
Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asp Asp
            35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
                100                 105                 110

Cys Tyr Pro Tyr Asp Val Pro Asp Tyr Ala Ser Leu Arg Ser Leu Val
```

-continued

```
              115                   120                   125
Ala Ser Ser Gly Thr Leu Glu Phe Ile Thr Glu Gly Phe Thr Trp Thr
     130                   135                   140
Gly Val Thr Gln Asn Gly Gly Ser Asn Ala Cys Lys Arg Gly Pro Gly
145                   150                   155                   160
Ser Gly Phe Phe Ser Arg Leu Asn Trp Leu Thr Lys Ser Gly Ser Thr
                   165                   170                   175
Tyr Pro Val Leu Asn Val Thr Met Pro Asn Asn Asp Asn Phe Asp Lys
                   180                   185                   190
Leu Tyr Ile Trp Gly Val His His Pro Ser Thr Asn Gln Glu Gln Thr
                   195                   200                   205
Ser Leu Tyr Val Gln Ala Ser Gly Arg Val Thr Val Ser Thr Arg Arg
     210                   215                   220
Ser Gln Gln Thr Ile Ile Pro Asn Ile Trp Ser Arg Pro Trp Val Arg
225                   230                   235                   240
Gly Leu Ser Ser Arg Ile Ser Ile Tyr Trp Thr Ile Val Lys Pro Gly
                   245                   250                   255
Asp Val Leu Val Ile Asn Ser Asn Gly Asn Leu Ile Ala Pro Arg Gly
                   260                   265                   270
Tyr Phe Lys Met Arg Thr Gly Lys Ser Ser Ile Met Arg Ser Asp Ala
                   275                   280                   285
Pro Ile Asp Thr Cys Ile Ser Glu Cys Ile Thr Pro Asn Gly Ser Ile
     290                   295                   300
Pro Asn Asp Lys Pro Phe Gln Asn Val Asn Lys Ile Thr Tyr Gly Ala
305                   310                   315                   320
Cys Pro Lys Tyr Val Lys Gln Asn Thr Leu Lys Leu Ala Thr Gly Met
                   325                   330                   335
Arg Asn Val Pro Glu Lys Gln Thr Arg Gly Leu Phe Gly Ala Ile Ala
                   340                   345                   350
Gly Phe Ile Glu Asn Gly Trp Glu Gly Met Ile Asp Gly Trp Tyr Gly
                   355                   360                   365
Phe Arg Trp Gln Asn Ser Glu Gly Thr Gly Gln Ala Ala Asp Leu Lys
                   370                   375                   380
Ser Thr Gln Ala Ala Ile Asp Gln Ile Asn Gly Ile Leu Asn Arg Val
385                   390                   395                   400
Ile Glu Lys Met Asn Glu Lys Phe His Gln Ile Glu Lys Glu Phe Ser
                   405                   410                   415
Glu Val Glu Gly Arg Ile Gln Asp Leu Glu Lys Tyr Val Glu Asp Thr
                   420                   425                   430
Lys Ile Asp Leu Trp Ser Tyr Asn Ala Glu Leu Leu Val Ala Leu Ile
                   435                   440                   445
Asn Gln His Thr Ile Asp Leu Thr Asp Ser Glu Met Asn Lys Leu Phe
     450                   455                   460
Glu Lys Thr Arg Arg Gln Leu Arg Glu Asn Ala Glu Asp Met Gly Asn
465                   470                   475                   480
Gly Cys Phe Lys Ile Tyr His Lys Cys Asp Asn Ala Cys Ile Glu Ser
                   485                   490                   495
Ile Arg Asn Gly Asn Tyr Asp His Asp Val Tyr Arg Asp Glu Ala Leu
                   500                   505                   510
Asn Asn Arg Phe Gln Ile Lys Gly Val Ser Gly Ser Leu Pro Glu Thr
                   515                   520                   525
Gly Gly Gly Ser His His His His His His
     530                   535
```

-continued

```
<210> SEQ ID NO 21
<211> LENGTH: 529
<212> TYPE: PRT
<213> ORGANISM: Artificial Sequence
<220> FEATURE:
<223> OTHER INFORMATION: UFV181137

<400> SEQUENCE: 21

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Ser Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Gln Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Ser Ala Cys Lys Arg Arg Ser Asn
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Ser Thr Asp Ser Asp Gln Ile
            195                 200                 205

Ser Ile Tyr Ala Gln Ala Ser Gly Arg Val Thr Val Ser Thr Lys Arg
    210                 215                 220

Ser Gln Gln Thr Val Ile Pro Asn Ile Gly Ser Ser Pro Trp Val Arg
225                 230                 235                 240

Gly Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365
```

```
Phe Arg His Gln Asn Ser Glu Gly Thr Gly Gln Ala Ala Asp Leu Lys
    370             375             380

Ser Thr Gln Ala Ala Ile Asn Gln Ile Asn Gly Lys Leu Asn Arg Leu
385             390             395             400

Ile Glu Lys Thr Asn Glu Lys Phe His Gln Ile Glu Lys Glu Phe Ser
            405             410             415

Glu Val Glu Gly Arg Ile Gln Asp Leu Glu Lys Tyr Val Glu Asp Thr
            420             425             430

Lys Ile Asp Leu Trp Ser Tyr Asn Ala Glu Leu Leu Val Ala Leu Glu
            435             440             445

Asn Gln His Thr Ile Asp Leu Thr Asp Ser Glu Met Asn Lys Leu Phe
    450             455             460

Glu Arg Thr Lys Lys Gln Leu Arg Glu Asn Ala Glu Asp Met Gly Asn
465             470             475             480

Gly Cys Phe Lys Ile Tyr His Lys Cys Asp Asn Ala Cys Ile Gly Ser
            485             490             495

Ile Arg Asn Gly Thr Tyr Asp His Asp Val Tyr Arg Asp Glu Ala Leu
            500             505             510

Asn Asn Arg Phe Gln Ile Lys Gly Val Gly Ser His His His His His
            515             520             525

His
```

<210> SEQ ID NO 22
<211> LENGTH: 538
<212> TYPE: PRT
<213> ORGANISM: Artificial Sequence
<220> FEATURE:
<223> OTHER INFORMATION: UFV181096

<400> SEQUENCE: 22

```
Met Lys Thr Ile Ile Ala Leu Ser Tyr Ile Leu Cys Leu Val Phe Ala
1               5               10              15

Gln Lys Leu Pro Gly Asn Asp Asn Ser Thr Ala Thr Leu Cys Leu Gly
            20              25              30

His His Ala Val Ser Asn Gly Thr Leu Val Lys Thr Ile Thr Asn Asp
        35              40              45

Gln Ile Glu Val Thr Asn Ala Thr Glu Leu Val Gln Ser Ser Ser Thr
    50              55              60

Gly Arg Ile Cys Asp Ser Pro His Gln Ile Leu Asp Gly Glu Asn Cys
65              70              75              80

Thr Leu Ile Asp Ala Leu Leu Gly Asp Pro His Cys Asp Gly Phe Gln
            85              90              95

Asn Lys Glu Trp Asp Leu Phe Val Glu Arg Ser Lys Ala Tyr Ser Asn
            100             105             110

Cys Tyr Pro Tyr Asp Val Pro Asp Tyr Ala Ser Leu Arg Ser Leu Val
        115             120             125

Ala Ser Ser Gly Thr Leu Glu Phe Asn Asn Glu Ser Phe Asn Trp Thr
    130             135             140

Gly Val Ala Gln Asn Gly Thr Ser Ser Ala Cys Lys Arg Arg Ser Asn
145             150             155             160

Lys Ser Phe Phe Ser Arg Leu Asn Trp Leu His Gln Leu Lys Tyr Lys
            165             170             175

Tyr Pro Ala Leu Asn Val Thr Met Pro Asn Asn Glu Lys Phe Asp Lys
            180             185             190
```

-continued

```
Leu Tyr Ile Trp Gly Val His His Pro Ser Thr Asp Ser Asp Gln Ile
        195             200             205

Ser Ile Tyr Ala Gln Ala Ser Gly Arg Val Thr Val Ser Thr Lys Arg
        210             215             220

Ser Gln Gln Thr Val Ile Pro Asn Ile Gly Ser Ser Pro Trp Val Arg
225             230             235             240

Gly Val Ser Ser Arg Ile Ser Ile Tyr Trp Thr Ile Val Lys Pro Gly
                245             250             255

Asp Ile Leu Leu Ile Asn Ser Thr Gly Asn Leu Ile Ala Pro Arg Gly
                260             265             270

Tyr Phe Lys Ile Arg Ser Gly Lys Ser Ser Ile Met Arg Ser Asp Ala
        275             280             285

Pro Ile Gly Lys Cys Asn Ser Glu Cys Ile Thr Pro Asn Gly Ser Ile
        290             295             300

Pro Asn Asp Lys Pro Phe Gln Asn Val Asn Arg Ile Thr Tyr Gly Ala
305             310             315             320

Cys Pro Arg Tyr Val Lys Gln Asn Thr Leu Lys Leu Ala Thr Gly Met
                325             330             335

Arg Asn Val Pro Glu Lys Gln Thr Arg Gly Ile Phe Gly Ala Ile Ala
                340             345             350

Gly Phe Ile Glu Asn Gly Trp Glu Gly Met Val Asp Gly Trp Tyr Gly
        355             360             365

Phe Arg Trp Gln Asn Ser Glu Gly Thr Gly Gln Ala Ala Asp Leu Lys
        370             375             380

Ser Thr Gln Ala Ala Ile Asn Gln Ile Asn Gly Ile Leu Asn Arg Leu
385             390             395             400

Ile Glu Lys Thr Asn Glu Lys Phe His Gln Ile Glu Lys Glu Phe Ser
                405             410             415

Glu Val Glu Gly Arg Ile Gln Asp Leu Glu Lys Tyr Val Glu Asp Thr
                420             425             430

Lys Ile Asp Leu Trp Ser Tyr Asn Ala Glu Leu Leu Val Ala Leu Ile
        435             440             445

Asn Gln His Thr Ile Asp Leu Thr Asp Ser Glu Met Asn Lys Leu Phe
        450             455             460

Glu Arg Thr Lys Lys Gln Leu Arg Glu Asn Ala Glu Asp Met Gly Asn
465             470             475             480

Gly Cys Phe Lys Ile Tyr His Lys Cys Asp Asn Ala Cys Ile Gly Ser
                485             490             495

Ile Arg Asn Gly Thr Tyr Asp His Asp Val Tyr Arg Asp Glu Ala Leu
                500             505             510

Asn Asn Arg Phe Gln Ile Lys Gly Val Ser Gly Ser Leu Pro Glu Thr
        515             520             525

Gly Gly Gly Ser His His His His His
        530             535
```

<210> SEQ ID NO 23
<211> LENGTH: 531
<212> TYPE: PRT
<213> ORGANISM: Artificial Sequence
<220> FEATURE:
<223> OTHER INFORMATION: UFV181145

<400> SEQUENCE: 23

```
Met Ile Ala Leu Ile Leu Val Ala Leu Ala Leu Ser His Thr Ala Tyr
1               5               10              15
```

-continued

```
Ser Gln Ile Thr Asn Gly Thr Thr Gly Asn Pro Ile Ile Cys Leu Gly
         20                  25                  30

His His Ala Val Glu Asn Gly Thr Ser Val Lys Thr Leu Thr Asp Asn
         35                  40                  45

His Val Glu Val Val Ser Ala Lys Glu Leu Val Glu Thr Asn His Thr
         50                  55                  60

Asp Glu Leu Cys Pro Ser Pro Leu Lys Leu Val Asp Gly Gln Asp Cys
65                  70                  75                  80

Asp Leu Ile Asn Gly Ala Leu Gly Ser Pro Gly Cys Asp Arg Leu Gln
                 85                  90                  95

Asp Thr Thr Trp Asp Val Phe Ile Glu Arg Pro Thr Ala Val Asp Thr
             100                 105                 110

Cys Tyr Pro Phe Asp Val Pro Asp Tyr Gln Ser Leu Arg Ser Ile Leu
             115                 120                 125

Ala Ser Ser Gly Ser Leu Glu Phe Ile Ala Glu Gln Phe Thr Trp Asn
     130                 135                 140

Gly Val Lys Val Asp Gly Ser Ser Ser Ala Cys Leu Arg Gly Gly Arg
145                 150                 155                 160

Asn Ser Phe Phe Ser Arg Leu Asn Trp Leu Thr Lys Glu Thr Asn Gly
                 165                 170                 175

Asn Tyr Gly Pro Ile Asn Val Thr Lys Glu Asn Thr Gly Ser Tyr Val
             180                 185                 190

Arg Leu Tyr Leu Trp Gly Val His His Pro Ser Ser Asp Asn Glu Gln
             195                 200                 205

Thr Asp Leu Tyr Lys Val Ala Thr Gly Arg Val Thr Val Ser Thr Arg
     210                 215                 220

Ser Asp Gln Ile Ser Ile Val Pro Asn Ile Gly Ser Arg Pro Arg Val
225                 230                 235                 240

Arg Asn Gln Ser Gly Arg Ile Ser Ile Tyr Trp Thr Leu Val Asn Pro
                 245                 250                 255

Gly Asp Ser Ile Ile Phe Asn Ser Ile Gly Asn Leu Ile Ala Pro Arg
             260                 265                 270

Gly His Tyr Lys Ile Ser Lys Ser Thr Lys Ser Thr Val Leu Lys Ser
             275                 280                 285

Asp Lys Arg Ile Gly Ser Cys Thr Ser Pro Cys Leu Thr Asp Lys Gly
     290                 295                 300

Ser Ile Gln Ser Asp Lys Pro Phe Gln Asn Val Ser Arg Ile Ala Ile
305                 310                 315                 320

Gly Asn Cys Pro Lys Tyr Val Lys Gln Gly Ser Leu Met Leu Ala Thr
                 325                 330                 335

Gly Met Arg Asn Ile Pro Gly Lys Gln Ala Lys Gly Leu Phe Gly Ala
             340                 345                 350

Ile Ala Gly Phe Ile Glu Asn Gly Trp Gln Gly Leu Ile Asp Gly Trp
             355                 360                 365

Tyr Gly Phe Arg His Gln Asn Ala Glu Gly Thr Gly Thr Ala Ala Asp
     370                 375                 380

Leu Lys Ser Thr Gln Ala Ala Ile Asp Gln Ile Asn Gly Lys Leu Asn
385                 390                 395                 400

Arg Leu Ile Glu Lys Thr Asn Glu Lys Tyr His Gln Ile Glu Lys Glu
                 405                 410                 415

Phe Glu Gln Val Glu Gly Arg Ile Gln Asp Leu Glu Lys Tyr Val Glu
             420                 425                 430

Asp Thr Lys Ile Asp Leu Trp Ser Tyr Asn Ala Glu Leu Leu Val Ala
```

```
                435                 440                 445

Leu Glu Asn Gln His Thr Ile Asp Val Thr Asp Ser Glu Met Asn Lys
    450                 455                 460

Leu Phe Glu Arg Val Arg Arg Gln Leu Arg Glu Asn Ala Glu Asp Gln
465                 470                 475                 480

Gly Asn Gly Cys Phe Glu Ile Phe His Gln Cys Asp Asn Asn Cys Ile
                485                 490                 495

Glu Ser Ile Arg Asn Gly Thr Tyr Asp His Asn Ile Tyr Arg Asp Glu
                500                 505                 510

Ala Ile Asn Asn Arg Ile Lys Ile Asn Pro Val Gly Ser His His His
                515                 520                 525

His His His
    530
```

```
<210> SEQ ID NO 24
<211> LENGTH: 540
<212> TYPE: PRT
<213> ORGANISM: Artificial Sequence
<220> FEATURE:
<223> OTHER INFORMATION: UFV180661

<400> SEQUENCE: 24

Met Ile Ala Leu Ile Leu Val Ala Leu Ala Leu Ser His Thr Ala Tyr
1               5                   10                  15

Ser Gln Ile Thr Asn Gly Thr Thr Gly Asn Pro Ile Ile Cys Leu Gly
                20                  25                  30

His His Ala Val Glu Asn Gly Thr Ser Val Lys Thr Leu Thr Asp Asn
            35                  40                  45

His Val Glu Val Val Ser Ala Lys Glu Leu Val Glu Thr Asn His Thr
    50                  55                  60

Asp Glu Leu Cys Pro Ser Pro Leu Lys Leu Val Asp Gly Gln Asp Cys
65                  70                  75                  80

Asp Leu Ile Asn Gly Ala Leu Gly Ser Pro Gly Cys Asp Arg Leu Gln
                85                  90                  95

Asp Thr Thr Trp Asp Val Phe Ile Glu Arg Pro Thr Ala Val Asp Thr
            100                 105                 110

Cys Tyr Pro Phe Asp Val Pro Asp Tyr Gln Ser Leu Arg Ser Ile Leu
        115                 120                 125

Ala Ser Ser Gly Ser Leu Glu Phe Ile Ala Glu Gln Phe Thr Trp Asn
    130                 135                 140

Gly Val Lys Val Asp Gly Ser Ser Ser Ala Cys Leu Arg Gly Gly Arg
145                 150                 155                 160

Asn Ser Phe Phe Ser Arg Leu Asn Trp Leu Thr Lys Glu Thr Asn Gly
                165                 170                 175

Asn Tyr Gly Pro Ile Asn Val Thr Lys Glu Asn Thr Gly Ser Tyr Val
            180                 185                 190

Arg Leu Tyr Leu Trp Gly Val His His Pro Ser Ser Asp Asn Glu Gln
        195                 200                 205

Thr Asp Leu Tyr Lys Val Ala Thr Gly Arg Val Thr Val Ser Thr Arg
    210                 215                 220

Ser Asp Gln Ile Ser Ile Val Pro Asn Ile Gly Ser Arg Pro Arg Val
225                 230                 235                 240

Arg Asn Gln Ser Gly Arg Ile Ser Ile Tyr Trp Thr Leu Val Asn Pro
            245                 250                 255

Gly Asp Ser Ile Ile Phe Asn Ser Ile Gly Asn Leu Ile Ala Pro Arg
```

-continued

```
              260              265              270

Gly His Tyr Lys Ile Ser Lys Ser Thr Lys Ser Thr Val Leu Lys Ser
         275              280              285

Asp Lys Arg Ile Gly Ser Cys Thr Ser Pro Cys Leu Thr Asp Lys Gly
    290              295              300

Ser Ile Gln Ser Asp Lys Pro Phe Gln Asn Val Ser Arg Ile Ala Ile
305              310              315              320

Gly Asn Cys Pro Lys Tyr Val Lys Gln Gly Ser Leu Met Leu Ala Thr
             325              330              335

Gly Met Arg Asn Ile Pro Gly Lys Gln Ala Lys Gly Leu Phe Gly Ala
             340              345              350

Ile Ala Gly Phe Ile Glu Asn Gly Trp Gln Gly Leu Ile Asp Gly Trp
             355              360              365

Tyr Gly Phe Arg Trp Gln Asn Ala Glu Gly Thr Gly Thr Ala Ala Asp
    370              375              380

Leu Lys Ser Thr Gln Ala Ala Ile Asp Gln Ile Asn Gly Ile Leu Asn
385              390              395              400

Arg Leu Ile Glu Lys Met Asn Glu Lys Tyr His Gln Ile Glu Lys Glu
             405              410              415

Phe Glu Gln Val Glu Gly Arg Ile Gln Asp Leu Glu Lys Tyr Val Glu
             420              425              430

Asp Thr Lys Ile Asp Leu Trp Ser Tyr Asn Ala Glu Leu Leu Val Ala
             435              440              445

Leu Ile Asn Gln His Thr Ile Asp Val Thr Asp Ser Glu Met Asn Lys
    450              455              460

Leu Phe Glu Arg Val Arg Arg Gln Leu Arg Glu Asn Ala Glu Asp Gln
465              470              475              480

Gly Asn Gly Cys Phe Glu Ile Phe His Gln Cys Asp Asn Asn Cys Ile
             485              490              495

Glu Ser Ile Arg Asn Gly Thr Tyr Asp His Asn Ile Tyr Arg Asp Glu
             500              505              510

Ala Ile Asn Asn Arg Ile Lys Ile Asn Pro Val Ser Gly Ser Leu Pro
             515              520              525

Glu Thr Gly Gly Gly Ser His His His His His
    530              535              540
```

<210> SEQ ID NO 25
<211> LENGTH: 523
<212> TYPE: PRT
<213> ORGANISM: Artificial Sequence
<220> FEATURE:
<223> OTHER INFORMATION: UFV181146

<400> SEQUENCE: 25

```
Met Asn Thr Gln Ile Leu Val Phe Ala Leu Met Ala Ile Ile Pro Thr
1               5               10              15

Asn Ala Asp Lys Ile Cys Leu Gly His His Ala Val Ser Asn Gly Thr
             20              25              30

Lys Val Asn Thr Leu Thr Glu Arg Gly Val Glu Val Val Asn Ala Thr
             35              40              45

Glu Thr Val Glu Arg Thr Asn Val Pro Arg Ile Cys Ser Lys Gly Lys
    50              55              60

Arg Thr Val Asp Leu Gly Gln Cys Gly Leu Leu Gly Thr Ile Thr Gly
65              70              75              80

Pro Pro Gln Cys Asp Gln Phe Leu Glu Phe Ser Ala Asp Leu Ile Ile
```

-continued

```
              85                    90                    95

Glu Arg Arg Glu Gly Ser Asp Val Cys Tyr Pro Gly Lys Phe Val Asn
              100               105               110

Glu Glu Ala Leu Arg Gln Ile Leu Arg Glu Ser Gly Gly Ile Asp Lys
              115               120               125

Glu Thr Met Gly Phe Thr Tyr Ser Gly Ile Arg Thr Asn Gly Ala Thr
    130               135               140

Ser Ala Cys Arg Arg Ser Gly Ser Ser Phe Tyr Ala Glu Met Lys Trp
145               150               155               160

Leu Leu Ser Asn Thr Asp Asn Ala Ala Phe Pro Gln Met Thr Lys Ser
              165               170               175

Tyr Lys Asn Thr Arg Lys Asp Pro Ala Leu Ile Ile Trp Gly Ile His
              180               185               190

His Ser Gly Ser Thr Thr Glu Gln Thr Lys Leu Tyr Gly Ser Gly Asn
              195               200               205

Lys Leu Ile Thr Val Gly Ser Ser Asn Tyr Gln Gln Ser Phe Val Pro
    210               215               220

Ser Pro Gly Ala Arg Pro Gln Val Asn Gly Gln Ser Gly Arg Ile Asp
225               230               235               240

Phe His Trp Leu Ile Leu Asn Pro Asn Asp Thr Val Thr Phe Ser Phe
              245               250               255

Asn Gly Ala Phe Ile Ala Pro Asp Arg Ala Ser Phe Leu Arg Gly Lys
              260               265               270

Ser Met Gly Ile Gln Ser Gly Val Gln Val Asp Ala Asn Cys Glu Gly
    275               280               285

Asp Cys Tyr His Ser Gly Gly Thr Ile Ile Ser Asn Leu Pro Phe Gln
    290               295               300

Asn Ile Asn Ser Arg Ala Val Gly Lys Cys Pro Arg Tyr Val Lys Gln
305               310               315               320

Glu Ser Leu Leu Leu Ala Thr Gly Met Lys Asn Val Pro Glu Ile Pro
              325               330               335

Lys Gly Arg Gly Leu Phe Gly Ala Ile Ala Gly Phe Ile Glu Asn Gly
              340               345               350

Trp Glu Gly Leu Ile Asp Gly Trp Tyr Gly Phe Arg His Gln Asn Ala
    355               360               365

Gln Gly Glu Gly Thr Ala Ala Asp Tyr Lys Ser Thr Gln Ser Ala Ile
    370               375               380

Asp Gln Ile Thr Gly Lys Leu Asn Arg Leu Ile Glu Lys Thr Asn Gln
385               390               395               400

Gln Phe Glu Leu Ile Asp Asn Glu Phe Thr Glu Val Glu Lys Gln Ile
              405               410               415

Gly Asn Val Ile Asn Trp Thr Arg Asp Ser Met Thr Glu Val Trp Ser
              420               425               430

Tyr Asn Ala Glu Leu Leu Val Ala Met Glu Asn Gln His Thr Ile Asp
    435               440               445

Leu Ala Asp Ser Glu Met Asn Lys Leu Tyr Glu Arg Val Lys Arg Gln
    450               455               460

Leu Arg Glu Asn Ala Glu Glu Asp Gly Thr Gly Cys Phe Glu Ile Phe
465               470               475               480

His Lys Cys Asp Asp Asp Cys Met Ala Ser Ile Arg Asn Asn Thr Tyr
              485               490               495

Asp His Ser Lys Tyr Arg Glu Glu Ala Met Gln Asn Arg Ile Gln Ile
              500               505               510
```

-continued

```
Asp Pro Val Gly Ser His His His His His His
        515             520

<210> SEQ ID NO 26
<211> LENGTH: 532
<212> TYPE: PRT
<213> ORGANISM: Artificial Sequence
<220> FEATURE:
<223> OTHER INFORMATION: UFV180664

<400> SEQUENCE: 26

Met Asn Thr Gln Ile Leu Val Phe Ala Leu Met Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
            115                 120                 125

Glu Thr Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
            180                 185                 190

His Ser Gly Ser Thr Thr Glu Gln Thr Lys Leu Tyr Gly Ser Gly Asn
            195                 200                 205

Lys Leu Ile Thr Val Gly Ser Ser Asn Tyr Gln Gln Ser Phe Val Pro
    210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
            275                 280                 285

Asp Cys Tyr His Ser Gly Gly Thr Ile Ile Ser Asn Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350
```

```
Trp Glu Gly Leu Ile Asp Gly Trp Tyr Gly Phe Arg Trp Gln Asn Ala
        355             360             365

Gln Gly Glu Gly Thr Ala Ala Asp Tyr Lys Ser Thr Gln Ser Ala Ile
        370             375             380

Asp Gln Ile Thr Gly Ile Leu Asn Arg Leu Ile Glu Lys Met Asn Gln
385             390             395             400

Gln Phe Glu Leu Ile Asp Asn Glu Phe Thr Glu Val Glu Lys Gln Ile
            405             410             415

Gly Asn Val Ile Asn Trp Thr Arg Asp Ser Met Thr Glu Val Trp Ser
            420             425             430

Tyr Asn Ala Glu Leu Leu Val Ala Met Ile Asn Gln His Thr Ile Asp
            435             440             445

Leu Ala Asp Ser Glu Met Asn Lys Leu Tyr Glu Arg Val Lys Arg Gln
        450             455             460

Leu Arg Glu Asn Ala Glu Glu Asp Gly Thr Gly Cys Phe Glu Ile Phe
465             470             475             480

His Lys Cys Asp Asp Asp Cys Met Ala Ser Ile Arg Asn Asn Thr Tyr
            485             490             495

Asp His Ser Lys Tyr Arg Glu Glu Ala Met Gln Asn Arg Ile Gln Ile
            500             505             510

Asp Pro Val Ser Gly Ser Leu Pro Glu Thr Gly Gly Gly Ser His His
            515             520             525

His His His His
    530
```

```
<210> SEQ ID NO 27
<211> LENGTH: 524
<212> TYPE: PRT
<213> ORGANISM: Artificial Sequence
<220> FEATURE:
<223> OTHER INFORMATION: UFV181147

<400> SEQUENCE: 27
```

```
Met Tyr Lys Val Val Val Ile Ile Ala Leu Leu Gly Ala Val Lys Gly
1               5               10              15

Leu Asp Arg Ile Cys Leu Gly His His Ala Val Ala Asn Gly Thr Ile
            20              25              30

Val Lys Thr Leu Thr Asn Glu Gln Glu Glu Val Thr Asn Ala Thr Glu
        35              40              45

Thr Val Glu Ser Thr Asn Leu Asn Lys Leu Cys Met Lys Gly Arg Ser
        50              55              60

Tyr Lys Asp Leu Gly Asn Cys His Pro Val Gly Met Leu Ile Gly Thr
65              70              75              80

Pro Val Cys Asp Pro His Leu Thr Gly Thr Trp Asp Thr Leu Ile Glu
            85              90              95

Arg Glu Asn Ala Ile Ala His Cys Tyr Pro Gly Ala Thr Ile Asn Glu
            100             105             110

Glu Ala Leu Arg Gln Lys Ile Met Glu Ser Gly Gly Ile Ser Lys Met
        115             120             125

Ser Thr Gly Phe Thr Tyr Gly Ser Ser Ile Asn Ser Ala Gly Thr Thr
        130             135             140

Lys Ala Cys Met Arg Asn Gly Gly Asp Ser Phe Tyr Ala Glu Leu Lys
145             150             155             160

Trp Leu Val Ser Lys Thr Lys Gly Gln Asn Phe Pro Gln Thr Thr Asn
            165             170             175
```

-continued

```
Thr Tyr Arg Asn Thr Asp Thr Ala Glu His Leu Ile Ile Trp Gly Ile
            180             185             190

His His Pro Ser Ser Thr Gln Glu Lys Asn Asp Leu Tyr Gly Thr Gln
            195             200             205

Ser Leu Ser Ile Ser Val Glu Ser Ser Thr Tyr Gln Asn Asn Phe Val
            210             215             220

Pro Val Val Gly Ala Arg Pro Gln Val Asn Gly Gln Ser Gly Arg Ile
225             230             235             240

Asp Phe His Trp Thr Leu Val Gln Pro Gly Asp Asn Ile Thr Phe Ser
            245             250             255

His Asn Gly Gly Leu Ile Ala Pro Ser Arg Val Ser Lys Leu Thr Gly
            260             265             270

Arg Gly Leu Gly Ile Gln Ser Glu Ala Leu Ile Asp Asn Ser Cys Glu
            275             280             285

Ser Lys Cys Phe Trp Arg Gly Gly Ser Ile Asn Thr Lys Leu Pro Phe
            290             295             300

Gln Asn Leu Ser Pro Arg Thr Val Gly Gln Cys Pro Lys Tyr Val Asn
305             310             315             320

Gln Arg Ser Leu Leu Leu Ala Thr Gly Met Arg Asn Val Pro Glu Val
            325             330             335

Val Gln Gly Arg Gly Leu Phe Gly Ala Ile Ala Gly Phe Ile Glu Asn
            340             345             350

Gly Trp Glu Gly Met Val Asp Gly Trp Tyr Gly Phe Arg His Gln Asn
            355             360             365

Ala Gln Gly Thr Gly Gln Ala Ala Asp Tyr Lys Ser Thr Gln Ala Ala
            370             375             380

Ile Asp Gln Ile Thr Gly Lys Leu Asn Arg Leu Ile Glu Lys Thr Asn
385             390             395             400

Thr Glu Phe Glu Ser Ile Glu Ser Glu Phe Ser Glu Thr Glu His Gln
            405             410             415

Ile Gly Asn Val Ile Asn Trp Thr Lys Asp Ser Ile Thr Asp Ile Trp
            420             425             430

Thr Tyr Gln Ala Glu Leu Leu Val Ala Met Glu Asn Gln His Thr Ile
            435             440             445

Asp Met Ala Asp Ser Glu Met Leu Asn Leu Tyr Glu Arg Val Arg Lys
            450             455             460

Gln Leu Arg Gln Asn Ala Glu Glu Asp Gly Lys Gly Cys Phe Glu Ile
465             470             475             480

Tyr His Thr Cys Asp Asp Ser Cys Met Glu Ser Ile Arg Asn Asn Thr
            485             490             495

Tyr Asp His Ser Gln Tyr Arg Glu Glu Ala Leu Leu Asn Arg Leu Asn
            500             505             510

Ile Asn Ser Val Gly Ser His His His His His
            515             520
```

```
<210> SEQ ID NO 28
<211> LENGTH: 532
<212> TYPE: PRT
<213> ORGANISM: Artificial Sequence
<220> FEATURE:
<223> OTHER INFORMATION: UFV180662

<400> SEQUENCE: 28

Met Tyr Lys Val Val Val Ile Ile Ala Leu Leu Gly Ala Val Lys Gly
1               5               10              15
```

-continued

```
Leu Asp Arg Ile Cys Leu Gly His His Ala Val Ala Asn Gly Thr Ile
        20              25              30

Val Lys Thr Leu Thr Asn Glu Gln Glu Glu Val Thr Asn Ala Thr Glu
        35              40              45

Thr Val Glu Ser Thr Asn Leu Asn Lys Leu Cys Met Lys Gly Arg Ser
    50              55              60

Tyr Lys Asp Leu Gly Asn Cys His Pro Val Gly Met Leu Ile Gly Thr
65              70              75              80

Pro Val Cys Asp Pro His Leu Thr Gly Thr Trp Asp Thr Leu Ile Glu
            85              90              95

Arg Glu Asn Ala Ile Ala His Cys Tyr Pro Gly Ala Thr Ile Asn Glu
            100             105             110

Glu Ala Leu Arg Gln Lys Ile Met Glu Ser Gly Gly Ile Ser Lys Met
        115             120             125

Ser Thr Gly Phe Thr Tyr Gly Ser Ser Ile Asn Ser Ala Gly Thr Thr
    130             135             140

Lys Ala Cys Met Arg Asn Gly Gly Asp Ser Phe Tyr Ala Glu Leu Lys
145             150             155             160

Trp Leu Val Ser Lys Thr Lys Gly Gln Asn Phe Pro Gln Thr Thr Asn
            165             170             175

Thr Tyr Arg Asn Thr Asp Thr Ala Glu His Leu Ile Ile Trp Gly Ile
            180             185             190

His His Pro Ser Ser Thr Gln Glu Lys Asn Asp Leu Tyr Gly Thr Gln
        195             200             205

Ser Leu Ser Ile Ser Val Glu Ser Ser Thr Tyr Gln Asn Asn Phe Val
    210             215             220

Pro Val Val Gly Ala Arg Pro Gln Val Asn Gly Gln Ser Gly Arg Ile
225             230             235             240

Asp Phe His Trp Thr Leu Val Gln Pro Gly Asp Asn Ile Thr Phe Ser
            245             250             255

His Asn Gly Gly Leu Ile Ala Pro Ser Arg Val Ser Lys Leu Thr Gly
            260             265             270

Arg Gly Leu Gly Ile Gln Ser Glu Ala Leu Ile Asp Asn Ser Cys Glu
        275             280             285

Ser Lys Cys Phe Trp Arg Gly Gly Ser Ile Asn Thr Lys Leu Pro Phe
    290             295             300

Gln Asn Leu Ser Pro Arg Thr Val Gly Gln Cys Pro Lys Tyr Val Asn
305             310             315             320

Gln Arg Ser Leu Leu Leu Ala Thr Gly Met Arg Asn Val Pro Glu Val
            325             330             335

Val Gln Gly Arg Gly Leu Phe Gly Ala Ile Ala Gly Phe Ile Glu Asn
            340             345             350

Gly Trp Glu Gly Met Val Asp Gly Trp Tyr Gly Phe Arg Trp Gln Asn
        355             360             365

Ala Gln Gly Thr Gly Gln Ala Ala Asp Tyr Lys Ser Thr Gln Ala Ala
    370             375             380

Ile Asp Gln Ile Thr Gly Ile Leu Asn Arg Leu Ile Glu Lys Met Asn
385             390             395             400

Thr Glu Phe Glu Ser Ile Glu Ser Glu Phe Ser Glu Thr Glu His Gln
            405             410             415

Ile Gly Asn Val Ile Asn Trp Thr Lys Asp Ser Ile Thr Asp Ile Trp
            420             425             430
```

```
Thr Tyr Gln Ala Glu Leu Leu Val Ala Met Ile Asn Gln His Thr Ile
    435                 440                 445

Asp Met Ala Asp Ser Glu Met Leu Asn Leu Tyr Glu Arg Val Arg Lys
    450                 455                 460

Gln Leu Arg Gln Asn Ala Glu Glu Asp Gly Lys Gly Cys Phe Glu Ile
465                 470                 475                 480

Tyr His Thr Cys Asp Asp Ser Cys Met Glu Ser Ile Arg Asn Asn Thr
                485                 490                 495

Tyr Asp His Ser Gln Tyr Arg Glu Glu Ala Leu Leu Asn Arg Leu Asn
                500                 505                 510

Ile Asn Ser Ser Gly Ser Leu Pro Glu Thr Gly Gly Gly Ser His His
                515                 520                 525

His His His His
    530

<210> SEQ ID NO 29
<211> LENGTH: 534
<212> TYPE: PRT
<213> ORGANISM: Artificial Sequence
<220> FEATURE:
<223> OTHER INFORMATION: UFV4239

<400> SEQUENCE: 29

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
                115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ser Ala Asp Gln Gln Ser Leu
                195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255
```

```
Ile Thr Phe Glu Ala Thr Gly Asn Leu Val Val Pro Arg Tyr Ala Phe
            260             265                 270

Ala Met Glu Arg Asn Ala Gly Ser Gly Ile Ile Ile Ser Asp Thr Pro
            275             280             285

Val His Asp Cys Asn Thr Thr Cys Gln Thr Pro Lys Gly Ala Ile Asn
        290             295             300

Thr Ser Leu Pro Phe Gln Asn Ile His Pro Ile Thr Ile Gly Lys Cys
305             310             315                 320

Pro Lys Tyr Val Lys Ser Thr Lys Leu Arg Leu Ala Thr Gly Leu Arg
            325             330                 335

Asn Ile Pro Ser Ile Gln Ser Gln Gly Leu Phe Gly Ala Ile Ala Gly
            340             345             350

Phe Ile Glu Gly Gly Trp Thr Gly Met Val Asp Gly Trp Tyr Gly Tyr
            355             360             365

His His Gln Asn Glu Gln Gly Ser Gly Tyr Ala Ala Asp Leu Lys Ser
        370             375             380

Thr Gln Asn Ala Ile Asp Glu Ile Thr Asn Lys Val Asn Ser Val Ile
385             390             395                 400

Glu Lys Met Asn Thr Gln Phe Thr Ala Val Gly Lys Glu Phe Asn His
            405             410             415

Leu Glu Lys Arg Ile Glu Asn Leu Asn Lys Lys Val Asp Asp Gly Phe
            420             425             430

Leu Asp Ile Trp Thr Tyr Asn Ala Glu Leu Leu Val Leu Leu Glu Asn
            435             440             445

Glu Arg Thr Leu Asp Tyr His Asp Ser Asn Val Lys Asn Leu Tyr Glu
        450             455             460

Lys Val Arg Ser Gln Leu Lys Asn Asn Ala Lys Glu Ile Gly Asn Gly
465             470             475                 480

Cys Phe Glu Phe Tyr His Lys Cys Asp Asn Thr Cys Met Glu Ser Val
            485             490             495

Lys Asn Gly Thr Tyr Asp Tyr Pro Lys Tyr Ser Glu Glu Ala Lys Leu
            500             505             510

Asn Arg Glu Glu Ile Asp Gly Arg Ser Leu Val Pro Arg Gly Ser Gly
        515             520             525

His His His His His His
    530
```

```
<210> SEQ ID NO 30
<211> LENGTH: 574
<212> TYPE: PRT
<213> ORGANISM: Artificial Sequence
<220> FEATURE:
<223> OTHER INFORMATION: UFV180843

<400> SEQUENCE: 30

Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20              25              30

Val Asp Thr Val Leu Glu Lys Asn Val Thr Val Thr His Ser Val Asn
        35              40              45

Leu Leu Glu Asp Lys His Asn Gly Lys Leu Cys Lys Leu Arg Gly Val
    50              55              60

Ala Pro Leu His Leu Gly Lys Cys Asn Ile Ala Gly Trp Ile Leu Gly
65              70              75                  80
```

```
Asn Pro Glu Cys Glu Ser Leu Ser Thr Ala Ser Ser Trp Ser Tyr Ile
                85                  90                  95

Val Glu Thr Ser Asn Ser Asp Asn Gly Thr Cys Tyr Pro Gly Asp Phe
            100             105             110

Ile Asn Tyr Glu Glu Leu Arg Glu Gln Leu Ser Ser Val Ser Ser Phe
        115             120             125

Glu Arg Phe Glu Ile Phe Pro Lys Thr Ser Ser Trp Pro Asn His Asp
    130             135             140

Ser Asn Lys Gly Val Thr Ala Ala Cys Pro His Ala Gly Ala Lys Ser
145             150             155             160

Phe Tyr Lys Asn Leu Ile Trp Leu Val Lys Lys Gly Asn Ser Tyr Pro
            165             170             175

Lys Leu Asn Gln Ser Tyr Ile Asn Asp Lys Gly Lys Glu Val Leu Val
        180             185             190

Leu Trp Gly Ile His His Pro Ser Thr Thr Ala Asp Gln Gln Ser Leu
        195             200             205

Tyr Gln Asn Ala Asp Ala Tyr Val Phe Val Gly Thr Ser Arg Tyr Ser
    210             215             220

Lys Lys Phe Lys Pro Glu Ile Ala Thr Arg Pro Lys Val Arg Asp Gln
225             230             235             240

Glu Gly Arg Met Asn Tyr Tyr Trp Thr Leu Val Glu Pro Gly Asp Lys
            245             250             255

Ile Thr Phe Glu Ala Thr Gly Asn Leu Val Val Pro Arg Tyr Ala Phe
            260             265             270

Thr Met Glu Arg Asn Ala Gly Ser Gly Ile Ile Ile Ser Asp Thr Pro
        275             280             285

Val His Asp Cys Asn Thr Thr Cys Gln Thr Pro Glu Gly Ala Ile Asn
    290             295             300

Thr Ser Leu Pro Phe Gln Asn Ile His Pro Ile Thr Ile Gly Lys Cys
305             310             315             320

Pro Lys Tyr Val Lys Ser Thr Lys Leu Arg Leu Ala Thr Gly Leu Arg
            325             330             335

Asn Val Pro Ser Ile Gln Ser Arg Gly Leu Phe Gly Ala Ile Ala Gly
            340             345             350

Phe Ile Glu Gly Gly Trp Thr Gly Met Val Asp Gly Trp Tyr Gly Tyr
        355             360             365

His His Gln Asn Glu Gln Gly Ser Gly Tyr Ala Ala Asp Leu Lys Ser
    370             375             380

Thr Gln Asn Ala Ile Asp Lys Ile Thr Asn Lys Val Asn Ser Val Ile
385             390             395             400

Glu Lys Met Asn Thr Gln Phe Thr Ala Val Gly Lys Glu Phe Asn His
            405             410             415

Leu Glu Lys Arg Ile Glu Asn Leu Asn Lys Lys Val Asp Asp Gly Phe
            420             425             430

Leu Asp Ile Trp Thr Tyr Asn Ala Glu Leu Leu Val Leu Leu Glu Asn
        435             440             445

Glu Arg Thr Leu Asp Tyr His Asp Ser Asn Val Lys Asn Leu Tyr Glu
    450             455             460

Lys Val Arg Asn Gln Leu Lys Asn Asn Ala Lys Glu Ile Gly Asn Gly
465             470             475             480

Cys Phe Glu Phe Tyr His Lys Cys Asp Asn Thr Cys Met Glu Ser Val
            485             490             495

Lys Asn Gly Thr Tyr Asp Tyr Pro Lys Tyr Ser Glu Glu Ala Lys Leu
```

-continued

```
                500                 505                 510

Asn Arg Glu Lys Ile Asp Ser Gly Ser Leu Val Pro Ser Gly Ser Pro
            515                 520                 525

Gly Ser Gly Tyr Ile Pro Glu Ala Pro Arg Asp Gly Gln Ala Tyr Val
        530                 535                 540

Arg Lys Asp Gly Glu Trp Val Leu Leu Ser Thr Phe Leu Gly Gly Ser
545                 550                 555                 560

Leu Pro Glu Thr Gly Gly Gly Ser His His His His His
                565                 570
```

```
<210> SEQ ID NO 31
<211> LENGTH: 573
<212> TYPE: PRT
<213> ORGANISM: Artificial Sequence
<220> FEATURE:
<223> OTHER INFORMATION: UFV180436

<400> SEQUENCE: 31

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
```

-continued

```
              290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
                340                 345                 350

Gly Phe Ile Glu Asn Gly Trp Glu Gly Met Ile Asp Gly Trp Tyr Gly
                355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
                500                 505                 510

Asn Asn Arg Phe Gln Ser Gly Ser Leu Val Pro Ser Gly Ser Pro Gly
                515                 520                 525

Ser Gly Tyr Ile Pro Glu Ala Pro Arg Asp Gly Gln Ala Tyr Val Arg
    530                 535                 540

Lys Asp Gly Glu Trp Val Leu Leu Ser Thr Phe Leu Gly Gly Ser Leu
545                 550                 555                 560

Pro Glu Thr Gly Gly Gly Ser His His His His His His
                565                 570
```

<210> SEQ ID NO 32
<211> LENGTH: 562
<212> TYPE: PRT
<213> ORGANISM: Artificial Sequence
<220> FEATURE:
<223> OTHER INFORMATION: UFV170466

<400> SEQUENCE: 32

```
Met Lys Thr Ile Val Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
```

-continued

```
                     85                90                95

Asn Lys Lys Trp Asp Leu Phe Val Glu Arg Ser Lys Ala Tyr Ser Asn
             100               105               110

Cys Tyr Pro Tyr Asp Val Pro Asp Tyr Ala Ser Leu Arg Ser Leu Val
             115               120               125

Ala Ser Ser Gly Thr Leu Glu Phe Asn Asn Glu Ser Phe Asn Trp Thr
     130               135               140

Gly Val Thr Gln Asn Gly Thr Ser Ser Ala Cys Ile Arg Arg Ser Asn
145               150               155               160

Ser Ser Phe Phe Ser Arg Leu Asn Trp Leu Thr His Leu Asn Phe Lys
             165               170               175

Tyr Pro Ala Leu Asn Val Thr Met Pro Asn Asn Glu Gln Phe Asp Lys
             180               185               190

Leu Tyr Ile Trp Gly Val His His Pro Gly Thr Asp Lys Asp Gln Ile
             195               200               205

Phe Leu Tyr Ala Gln Ser Ser Gly Arg Ile Thr Val Ser Thr Lys Arg
     210               215               220

Ser Gln Gln Ala Val Ile Pro Asn Ile Gly Ser Arg Pro Arg Ile Arg
225               230               235               240

Asn Ile Pro Ser Arg Ile Ser Ile Tyr Trp Thr Ile Val Lys Pro Gly
             245               250               255

Asp Ile Leu Leu Ile Asn Ser Thr Gly Asn Leu Ile Ala Pro Arg Gly
             260               265               270

Tyr Phe Lys Ile Arg Ser Gly Lys Ser Ser Ile Met Arg Ser Asp Ala
             275               280               285

Pro Ile Gly Lys Cys Asn Ser Glu Cys Ile Thr Pro Asn Gly Ser Ile
     290               295               300

Pro Asn Asp Lys Pro Phe Gln Asn Val Asn Arg Ile Thr Tyr Gly Ala
305               310               315               320

Cys Pro Arg Tyr Val Lys Gln Ser Thr Leu Lys Leu Ala Thr Gly Met
             325               330               335

Arg Asn Val Pro Glu Lys Gln Thr Arg Gly Ile Phe Gly Ala Ile Ala
             340               345               350

Gly Phe Ile Glu Asn Gly Trp Glu Gly Met Val Asp Gly Trp Tyr Gly
             355               360               365

Phe Arg His Gln Asn Ser Glu Gly Arg Gly Gln Ala Ala Asp Leu Lys
     370               375               380

Ser Thr Gln Ala Ala Ile Asp Gln Ile Asn Gly Lys Leu Asn Arg Leu
385               390               395               400

Ile Gly Lys Thr Asn Glu Lys Phe His Gln Ile Glu Lys Glu Phe Ser
             405               410               415

Glu Val Glu Gly Arg Ile Gln Asp Leu Glu Lys Tyr Val Glu Asp Thr
             420               425               430

Lys Ile Asp Leu Trp Ser Tyr Asn Ala Glu Leu Leu Val Ala Leu Glu
             435               440               445

Asn Gln His Thr Ile Asp Leu Thr Asp Ser Glu Met Asn Lys Leu Phe
     450               455               460

Glu Lys Thr Lys Lys Gln Leu Arg Glu Asn Ala Glu Asp Met Gly Asn
465               470               475               480

Gly Cys Phe Lys Ile Tyr His Lys Cys Asp Asn Ala Cys Ile Gly Ser
             485               490               495

Ile Arg Asn Gly Thr Tyr Asn His Asp Val Tyr Arg Asp Glu Ala Leu
             500               505               510
```

-continued

```
Asn Asn Arg Phe Gln Ser Gly Ser Leu Val Pro Arg Gly Ser Gly Ser
        515             520             525
```

```
Gly Tyr Ile Pro Glu Ala Pro Arg Asp Gly Gln Ala Tyr Val Arg Lys
        530             535             540
```

```
Asp Gly Glu Trp Val Leu Leu Ser Thr Phe Leu Gly Gly Ser Glu Pro
545             550             555             560
```

```
Glu Ala
```

```
<210> SEQ ID NO 33
<211> LENGTH: 538
<212> TYPE: PRT
<213> ORGANISM: Artificial Sequence
<220> FEATURE:
<223> OTHER INFORMATION: UFV181099
```

```
<400> SEQUENCE: 33
```

```
Met Lys Thr Ile Val Ala Leu Ser Tyr Ile Leu Cys Leu Val Phe Ala
1               5               10              15
```

```
Gln Lys Leu Pro Gly Asn Asp Asn Ser Thr Ala Thr Leu Cys Leu Gly
        20              25              30
```

```
His His Ala Val Pro Asn Gly Thr Ile Val Lys Thr Ile Thr Asn Asp
        35              40              45
```

```
Gln Ile Glu Val Thr Asn Ala Thr Glu Leu Val Gln Ser Ser Ser Thr
        50              55              60
```

```
Gly Glu Ile Cys Asp Ser Pro His Gln Ile Leu Asp Gly Glu Asn Cys
65              70              75              80
```

```
Thr Leu Ile Asp Ala Leu Leu Gly Asp Pro Gln Cys Asp Gly Phe Gln
                85              90              95
```

```
Asn Lys Lys Trp Asp Leu Phe Val Glu Arg Ser Lys Ala Tyr Ser Asn
        100             105             110
```

```
Cys Tyr Pro Tyr Asp Val Pro Asp Tyr Ala Ser Leu Arg Ser Leu Val
        115             120             125
```

```
Ala Ser Ser Gly Thr Leu Glu Phe Asn Asn Glu Ser Phe Asn Trp Thr
        130             135             140
```

```
Gly Val Thr Gln Asn Gly Thr Ser Ser Ala Cys Ile Arg Arg Ser Asn
145             150             155             160
```

```
Ser Ser Phe Phe Ser Arg Leu Asn Trp Leu Thr His Leu Asn Phe Lys
                165             170             175
```

```
Tyr Pro Ala Leu Asn Val Thr Met Pro Asn Asn Glu Gln Phe Asp Lys
                180             185             190
```

```
Leu Tyr Ile Trp Gly Val His His Pro Gly Thr Asp Lys Asp Gln Ile
        195             200             205
```

```
Phe Leu Tyr Ala Gln Ser Ser Gly Arg Ile Thr Val Ser Thr Lys Arg
        210             215             220
```

```
Ser Gln Gln Ala Val Ile Pro Asn Ile Gly Ser Arg Pro Arg Ile Arg
225             230             235             240
```

```
Asn Ile Pro Ser Arg Ile Ser Ile Tyr Trp Thr Ile Val Lys Pro Gly
                245             250             255
```

```
Asp Ile Leu Leu Ile Asn Ser Thr Gly Asn Leu Ile Ala Pro Arg Gly
                260             265             270
```

```
Tyr Phe Lys Ile Arg Ser Gly Lys Ser Ser Ile Met Arg Ser Asp Ala
        275             280             285
```

```
Pro Ile Gly Lys Cys Asn Ser Glu Cys Ile Thr Pro Asn Gly Ser Ile
        290             295             300
```

```
Pro Asn Asp Lys Pro Phe Gln Asn Val Asn Arg Ile Thr Tyr Gly Ala
305             310             315             320

Cys Pro Arg Tyr Val Lys Gln Ser Thr Leu Lys Leu Ala Thr Gly Met
                325             330             335

Arg Asn Val Pro Glu Lys Gln Thr Arg Gly Ile Phe Gly Ala Ile Ala
            340             345             350

Gly Phe Ile Glu Asn Gly Trp Glu Gly Met Val Asp Gly Trp Tyr Gly
        355             360             365

Phe Arg Trp Gln Asn Ser Glu Gly Arg Gly Gln Ala Ala Asp Leu Lys
    370             375             380

Ser Thr Gln Ala Ala Ile Asp Gln Ile Asn Gly Ile Leu Asn Arg Leu
385             390             395             400

Ile Gly Lys Thr Asn Glu Lys Phe His Gln Ile Glu Lys Glu Phe Ser
            405             410             415

Glu Val Glu Gly Arg Ile Gln Asp Leu Glu Lys Tyr Val Glu Asp Thr
            420             425             430

Lys Ile Asp Leu Trp Ser Tyr Asn Ala Glu Leu Leu Val Ala Leu Ile
            435             440             445

Asn Gln His Thr Ile Asp Leu Thr Asp Ser Glu Met Asn Lys Leu Phe
    450             455             460

Glu Lys Thr Lys Lys Gln Leu Arg Glu Asn Ala Glu Asp Met Gly Asn
465             470             475             480

Gly Cys Phe Lys Ile Tyr His Lys Cys Asp Asn Ala Cys Ile Gly Ser
            485             490             495

Ile Arg Asn Gly Thr Tyr Asn His Asp Val Tyr Arg Asp Glu Ala Leu
            500             505             510

Asn Asn Arg Phe Gln Ile Lys Gly Val Ser Gly Ser Leu Pro Glu Thr
        515             520             525

Gly Gly Gly Ser His His His His His His
    530             535
```

```
<210> SEQ ID NO 34
<211> LENGTH: 535
<212> TYPE: PRT
<213> ORGANISM: Artificial Sequence
<220> FEATURE:
<223> OTHER INFORMATION: UFV181005

<400> SEQUENCE: 34
```

```
Met Lys Ala Ile Leu Val Val Leu Leu Tyr Thr Phe Ala Thr Ala Asn
1               5               10              15

Ala Asp Thr Leu Cys Ile Gly Tyr His Ala Asn Asn Ser Thr Asp Thr
            20              25              30

Val Asp Thr Val Leu Glu Lys Asn Val Thr Val Thr His Ser Val Asn
        35              40              45

Leu Leu Glu Asp Lys His Asn Gly Lys Leu Cys Lys Leu Arg Gly Val
    50              55              60

Ala Pro Leu His Leu Gly Lys Cys Asn Ile Ala Gly Trp Ile Leu Gly
65              70              75              80

Asn Pro Glu Cys Glu Ser Leu Ser Thr Ala Ser Ser Trp Ser Tyr Ile
            85              90              95

Val Glu Thr Pro Ser Ser Asp Asn Gly Thr Cys Tyr Pro Gly Asp Phe
            100             105             110

Ile Asp Tyr Glu Glu Leu Arg Glu Gln Leu Ser Ser Val Ser Ser Phe
            115             120             125
```

```
Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
            355                 360                 365

His Trp Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Ile Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Ser Gly Ser Leu Pro Glu Thr Gly Gly Gly
            515                 520                 525

Ser His His His His His His
    530                 535
```

```
<210> SEQ ID NO 35
<211> LENGTH: 535
<212> TYPE: PRT
<213> ORGANISM: Artificial Sequence
<220> FEATURE:
<223> OTHER INFORMATION: UFV181007

<400> SEQUENCE: 35

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
```

-continued

```
        370             375             380

Thr Gln Asn Ala Ile Asp Glu Ile Thr Asn Ile Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Ile Asn
                435                 440                 445

Glu Arg Thr Leu Asp Tyr His Asp Ser Asn Val Lys Asn Leu Tyr Glu
                450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Ser Gly Ser Leu Pro Glu Thr Gly Gly Gly
                515                 520                 525

Ser His His His His His
        530                 535

<210> SEQ ID NO 36
<211> LENGTH: 534
<212> TYPE: PRT
<213> ORGANISM: Artificial Sequence
<220> FEATURE:
<223> OTHER INFORMATION: UFV181090

<400> SEQUENCE: 36

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
        130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
                180                 185                 190

Trp Gly Val His His Pro Pro Asn Ile Gly Asp Gln Lys Ala Leu Tyr
```

-continued

```
          195               200               205

His Thr Glu Asn Ala Tyr Val Ser Val Val Ser Ser His Tyr Ser Arg
    210               215               220

Lys Phe Thr Pro Glu Ile Ala Lys Arg Pro Lys Val Arg Asp Gln Glu
225               230               235               240

Gly Arg Ile Asn Tyr Tyr Trp Thr Leu Leu Glu Pro Gly Asp Thr Ile
              245               250               255

Ile Phe Glu Ala Asn Gly Asn Leu Ile Ala Pro Arg Tyr Ala Phe Ala
              260               265               270

Leu Ser Arg Gly Phe Gly Ser Gly Ile Ile Asn Ser Asn Ala Pro Met
              275               280               285

Asp Lys Cys Asp Ala Lys Cys Gln Thr Pro Gln Gly Ala Ile Asn Ser
    290               295               300

Ser Leu Pro Phe Gln Asn Val His Pro Val Thr Ile Gly Glu Cys Pro
305               310               315               320

Lys Tyr Val Arg Ser Ala Lys Leu Arg Met Val Thr Gly Leu Arg Asn
              325               330               335

Ile Pro Ser Ile Gln Ser Arg Gly Leu Phe Gly Ala Ile Ala Gly Phe
              340               345               350

Ile Glu Gly Gly Trp Thr Gly Met Val Asp Gly Trp Tyr Gly Tyr His
              355               360               365

Trp Gln Asn Glu Gln Gly Ser Gly Tyr Ala Ala Asp Gln Lys Ser Thr
    370               375               380

Gln Asn Ala Ile Asn Gly Ile Thr Asn Ile Val Asn Ser Val Ile Glu
385               390               395               400

Lys Met Asn Thr Gln Phe Thr Ala Val Gly Lys Glu Phe Asn Lys Leu
              405               410               415

Glu Arg Arg Met Glu Asn Leu Asn Lys Lys Val Asp Asp Gly Phe Ile
              420               425               430

Asp Ile Trp Thr Tyr Asn Ala Glu Leu Leu Val Leu Leu Ile Asn Glu
              435               440               445

Arg Thr Leu Asp Phe His Asp Ser Asn Val Lys Asn Leu Tyr Glu Lys
    450               455               460

Val Lys Ser Gln Leu Lys Asn Asn Ala Lys Glu Ile Gly Asn Gly Cys
465               470               475               480

Phe Glu Phe Tyr His Lys Cys Asn Asp Glu Cys Ile Glu Ser Val Lys
              485               490               495

Asn Gly Thr Tyr Asp Tyr Pro Lys Tyr Ser Glu Glu Ser Lys Leu Asn
              500               505               510

Arg Glu Lys Ile Asp Ser Gly Ser Leu Pro Glu Thr Gly Gly Gly Ser
    515               520               525

His His His His His His
    530

<210> SEQ ID NO 37
<211> LENGTH: 525
<212> TYPE: PRT
<213> ORGANISM: Artificial Sequence
<220> FEATURE:
<223> OTHER INFORMATION: UFV181135

<400> SEQUENCE: 37

Met Lys Val Lys Leu Leu Val Leu Leu Cys Thr Phe Thr Ala Thr Tyr
1               5               10               15

Ala Asp Thr Ile Cys Ile Gly Tyr His Ala Asn Asn Ser Thr Asp Thr
```

-continued

```
                20                  25                  30

Val Asp Thr Val Leu Glu Lys Asn Val Thr Val Thr His Ser Val Asn
            35                  40                  45

Leu Leu Glu Asn Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
            165                 170                 175

Leu Ser Lys Ser Tyr Ala Asn Asn Lys Glu Lys Glu Val Leu Val Leu
        180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
            245                 250                 255

Ile Phe Glu Ala Asn Gly Asn Leu Ile Ala Pro Arg Tyr Ala Phe Ala
        260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
            325                 330                 335

Ile Pro Ser Ile Gln Ser Gln Gly Leu Phe Gly Ala Ile Ala Gly Phe
        340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
            405                 410                 415

Glu Arg Arg Met Glu Asn Leu Asn Lys Lys Val Asp Asp Gly Phe Ile
        420                 425                 430

Asp Ile Trp Thr Tyr Asn Ala Glu Leu Leu Val Leu Leu Glu Asn Glu
        435                 440                 445
```

```
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Ser His His His His His
        515                 520                 525
```

<210> SEQ ID NO 38
<211> LENGTH: 535
<212> TYPE: PRT
<213> ORGANISM: Artificial Sequence
<220> FEATURE:
<223> OTHER INFORMATION: UFV181084

<400> SEQUENCE: 38

```
Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
                100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
                180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
                260                 265                 270

Ala Leu Asn Arg Gly Ser Gly Ser Gly Ile Ile Thr Ser Asp Ala Pro
                275                 280                 285
```

-continued

```
Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
                355                 360                 365

His Trp Gln Asn Glu Gln Gly Ser Gly Tyr Ala Ala Asp Gln Lys Ser
    370                 375                 380

Thr Gln Asn Ala Ile Asp Gly Ile Thr Asn Ile Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Ile Asn
                435                 440                 445

Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Ile Glu Ser Val
                485                 490                 495

Arg Asn Gly Thr Tyr Asp Tyr Pro Lys Tyr Ser Glu Glu Ser Lys Leu
                500                 505                 510

Asn Arg Glu Glu Ile Asp Ser Gly Ser Leu Pro Glu Thr Gly Gly Gly
    515                 520                 525

Ser His His His His His His
    530                 535
```

```
<210> SEQ ID NO 39
<211> LENGTH: 526
<212> TYPE: PRT
<213> ORGANISM: Artificial Sequence
<220> FEATURE:
<223> OTHER INFORMATION: UFV181131

<400> SEQUENCE: 39
```

```
Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
                100                 105                 110
```

US 12,630,591 B2

145

146

-continued

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
            195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
            275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Ser His His His His His
            515                 520                 525

-continued

<210> SEQ ID NO 40
<211> LENGTH: 538
<212> TYPE: PRT
<213> ORGANISM: Artificial Sequence
<220> FEATURE:
<223> OTHER INFORMATION: UFV181095

<400> SEQUENCE: 40

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Ile Asn Glu Asp Phe Asn Trp Thr
    130                 135                 140

Gly Val Ala Gln Asp Gly Lys Ser Tyr Thr Cys Lys Arg Gly Ser Val
145                 150                 155                 160

Asn Ser Phe Phe Ser Arg Leu Asn Trp Leu His Lys Leu Glu Tyr Lys
                165                 170                 175

Tyr Pro Ala Leu Asn Val Thr Met Pro Asn Asn Gly Lys Phe Asp Lys
            180                 185                 190

Leu Tyr Ile Trp Gly Val His His Pro Ser Thr Asp Ser Asp Gln Thr
            195                 200                 205

Ser Leu Tyr Val Arg Ala Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
            245                 250                 255

Asp Ile Leu Leu Ile Asn Ser Thr Gly Asn Leu Ile Ala Pro Arg Gly
            260                 265                 270

Tyr Phe Lys Ile Arg Asn Gly Lys Ser Ser Ile Met Arg Ser Asp Ala
            275                 280                 285

Pro Ile Gly Asn Cys Ser Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365
```

Phe Arg Trp Gln Asn Ser Glu Gly Thr Gly Gln Ala Ala Asp Leu Lys
    370             375             380

Ser Thr Gln Ala Ala Ile Asp Gln Ile Asn Gly Ile Leu Asn Arg Leu
385             390             395             400

Ile Glu Lys Thr Asn Glu Lys Phe His Gln Ile Glu Lys Glu Phe Ser
            405             410             415

Glu Val Glu Gly Arg Ile Gln Asp Leu Glu Lys Tyr Val Glu Asp Thr
            420             425             430

Lys Ile Asp Leu Trp Ser Tyr Asn Ala Glu Leu Leu Val Ala Leu Ile
            435             440             445

Asn Gln His Thr Ile Asp Leu Thr Asp Ser Glu Met Asn Lys Leu Phe
    450             455             460

Glu Arg Thr Arg Lys Gln Leu Arg Glu Asn Ala Glu Asp Met Gly Asn
465             470             475             480

Gly Cys Phe Lys Ile Tyr His Lys Cys Asp Asn Ala Cys Ile Gly Ser
            485             490             495

Ile Arg Asn Gly Thr Tyr Asp His Asp Val Tyr Arg Asp Glu Ala Leu
            500             505             510

Asn Asn Arg Phe Gln Ile Lys Gly Val Ser Gly Ser Leu Pro Glu Thr
            515             520             525

Gly Gly Gly Ser His His His His His
    530             535

<210> SEQ ID NO 41
<211> LENGTH: 529
<212> TYPE: PRT
<213> ORGANISM: Artificial Sequence
<220> FEATURE:
<223> OTHER INFORMATION: UFV181140

<400> SEQUENCE: 41

Met Lys Thr Ile Ile Ala Leu Ser Tyr Ile Leu Cys Leu Val Phe Ala
1               5               10              15

Gln Lys Leu Pro Gly Asn Asp Asn Ser Thr Ala Thr Leu Cys Leu Gly
            20              25              30

His His Ala Val Pro Asn Gly Thr Leu Val Lys Thr Ile Thr Asn Asp
        35              40              45

Gln Ile Glu Val Thr Asn Ala Thr Glu Leu Val Gln Ser Ser Ser Thr
    50              55              60

Gly Arg Ile Cys Asp Ser Pro His Arg Ile Leu Asp Gly Lys Asn Cys
65              70              75              80

Thr Leu Ile Asp Ala Leu Leu Gly Asp Pro His Cys Asp Gly Phe Gln
            85              90              95

Asn Lys Glu Trp Asp Leu Phe Val Glu Arg Ser Lys Ala Tyr Ser Asn
            100             105             110

Cys Tyr Pro Tyr Asp Val Pro Asp Tyr Ala Ser Leu Arg Ser Leu Val
        115             120             125

Ala Ser Ser Gly Thr Leu Glu Phe Ile Asn Glu Asp Phe Asn Trp Thr
    130             135             140

Gly Val Ala Gln Asp Gly Lys Ser Tyr Thr Cys Lys Arg Gly Ser Val
145             150             155             160

Asn Ser Phe Phe Ser Arg Leu Asn Trp Leu His Lys Leu Glu Tyr Lys
            165             170             175

Tyr Pro Ala Leu Asn Val Thr Met Pro Asn Asn Gly Lys Phe Asp Lys
            180             185             190

```
Leu Tyr Ile Trp Gly Val His His Pro Ser Thr Asp Ser Asp Gln Thr
        195             200             205

Ser Leu Tyr Val Arg Ala Ser Gly Arg Val Thr Val Ser Thr Lys Arg
    210             215             220

Ser Gln Gln Thr Val Ile Pro Asn Ile Gly Ser Arg Pro Trp Val Arg
225             230             235             240

Gly Leu Ser Ser Arg Ile Ser Ile Tyr Trp Thr Ile Val Lys Pro Gly
            245             250             255

Asp Ile Leu Leu Ile Asn Ser Thr Gly Asn Leu Ile Ala Pro Arg Gly
            260             265             270

Tyr Phe Lys Ile Arg Asn Gly Lys Ser Ser Ile Met Arg Ser Asp Ala
        275             280             285

Pro Ile Gly Asn Cys Ser Ser Glu Cys Ile Thr Pro Asn Gly Ser Ile
    290             295             300

Pro Asn Asp Lys Pro Phe Gln Asn Val Asn Arg Ile Thr Tyr Gly Ala
305             310             315             320

Cys Pro Arg Tyr Val Lys Gln Asn Thr Leu Lys Leu Ala Thr Gly Met
            325             330             335

Arg Asn Val Pro Glu Lys Gln Thr Arg Gly Ile Phe Gly Ala Ile Ala
            340             345             350

Gly Phe Ile Glu Asn Gly Trp Glu Gly Met Val Asp Gly Trp Tyr Gly
        355             360             365

Phe Arg His Gln Asn Ser Glu Gly Thr Gly Gln Ala Ala Asp Leu Lys
    370             375             380

Ser Thr Gln Ala Ala Ile Asp Gln Ile Asn Gly Lys Leu Asn Arg Leu
385             390             395             400

Ile Glu Lys Thr Asn Glu Lys Phe His Gln Ile Glu Lys Glu Phe Ser
            405             410             415

Glu Val Glu Gly Arg Ile Gln Asp Leu Glu Lys Tyr Val Glu Asp Thr
            420             425             430

Lys Ile Asp Leu Trp Ser Tyr Asn Ala Glu Leu Leu Val Ala Leu Glu
        435             440             445

Asn Gln His Thr Ile Asp Leu Thr Asp Ser Glu Met Asn Lys Leu Phe
    450             455             460

Glu Arg Thr Arg Lys Gln Leu Arg Glu Asn Ala Glu Asp Met Gly Asn
465             470             475             480

Gly Cys Phe Lys Ile Tyr His Lys Cys Asp Asn Ala Cys Ile Gly Ser
            485             490             495

Ile Arg Asn Gly Thr Tyr Asp His Asp Val Tyr Arg Asp Glu Ala Leu
            500             505             510

Asn Asn Arg Phe Gln Ile Lys Gly Val Gly Ser His His His His
            515             520             525

His
```

```
<210> SEQ ID NO 42
<211> LENGTH: 538
<212> TYPE: PRT
<213> ORGANISM: Artificial Sequence
<220> FEATURE:
<223> OTHER INFORMATION: UFV181093

<400> SEQUENCE: 42

Met Lys Thr Ile Ile Ala Leu Ser Tyr Ile Phe Cys Gln Val Leu Ala
1               5               10              15

Gln Asn Leu Pro Gly Asn Asp Asn Ser Thr Ala Thr Leu Cys Leu Gly
```

-continued

```
                    20                    25                    30

His His Ala Val Pro Asn Gly Thr Leu Val Lys Thr Ile Thr Asn Asp
            35                    40                    45

Gln Ile Glu Val Thr Asn Ala Thr Glu Leu Val Gln Ser Ser Ser Thr
    50                    55                    60

Gly Arg Ile Cys Asp Ser Pro His Arg Ile Leu Asp Gly Lys Asn Cys
65                    70                    75                    80

Thr Leu Ile Asp Ala Leu Leu Gly Asp Pro His Cys Asp Gly Phe Gln
                85                    90                    95

Asn Glu Lys Trp Asp Leu Phe Val Glu Arg Ser Lys Ala Phe Ser Asn
            100                   105                   110

Cys Tyr Pro Tyr Asp Val Pro Asp Tyr Ala Ser Leu Arg Ser Leu Val
            115                   120                   125

Ala Ser Ser Gly Thr Leu Glu Phe Ile Asn Glu Gly Phe Asn Trp Thr
    130                   135                   140

Gly Val Thr Gln Asn Gly Gly Ser Tyr Ala Cys Lys Arg Gly Pro Asp
145                   150                   155                   160

Lys Ser Phe Phe Ser Arg Leu Asn Trp Leu Tyr Glu Ser Glu Ser Thr
            165                   170                   175

Tyr Pro Val Leu Asn Val Thr Met Pro Asn Asn Asp Asn Phe Asp Lys
            180                   185                   190

Leu Tyr Ile Trp Gly Val His His Pro Ser Thr Asp Lys Glu Gln Thr
            195                   200                   205

Asn Leu Tyr Val Gln Ala Ser Gly Arg Val Thr Val Ser Thr Lys Arg
    210                   215                   220

Ser Gln Gln Thr Ile Ile Pro Asn Val Gly Ser Arg Pro Trp Val Arg
225                   230                   235                   240

Gly Leu Ser Ser Arg Ile Ser Ile Tyr Trp Thr Ile Val Lys Pro Gly
            245                   250                   255

Asp Ile Leu Leu Ile Asn Ser Asn Gly Asn Leu Ile Ala Pro Arg Gly
            260                   265                   270

Tyr Phe Lys Ile Arg Thr Gly Lys Ser Ser Ile Met Arg Ser Asp Ala
            275                   280                   285

Pro Ile Gly Thr Cys Ser Ser Glu Cys Ile Thr Pro Asn Gly Ser Ile
    290                   295                   300

Pro Asn Asp Lys Pro Phe Gln Asn Val Asn Lys Ile Thr Tyr Gly Ala
305                   310                   315                   320

Cys Pro Lys Tyr Val Lys Gln Asn Thr Leu Lys Leu Ala Thr Gly Met
            325                   330                   335

Arg Asn Val Pro Glu Lys Gln Thr Arg Gly Ile Phe Gly Ala Ile Ala
            340                   345                   350

Gly Phe Ile Glu Asn Gly Trp Glu Gly Met Ile Asp Gly Trp Tyr Gly
            355                   360                   365

Phe Arg Trp Gln Asn Ser Glu Gly Thr Gly Gln Ala Ala Asp Leu Lys
    370                   375                   380

Ser Thr Gln Ala Ala Ile Asp Gln Ile Asn Gly Ile Leu Asn Arg Val
385                   390                   395                   400

Ile Glu Lys Thr Asn Glu Lys Phe His Gln Ile Glu Lys Glu Phe Ser
            405                   410                   415

Glu Val Glu Gly Arg Ile Gln Asp Leu Glu Lys Tyr Val Glu Asp Thr
            420                   425                   430

Lys Ile Asp Leu Trp Ser Tyr Asn Ala Glu Leu Leu Val Ala Leu Ile
            435                   440                   445
```

-continued

```
Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Ser Gly Ser Leu Pro Glu Thr
            515                 520                 525

Gly Gly Gly Ser His His His His His His
        530                 535
```

<210> SEQ ID NO 43
<211> LENGTH: 529
<212> TYPE: PRT
<213> ORGANISM: Artificial Sequence
<220> FEATURE:
<223> OTHER INFORMATION: UFV181136

<400> SEQUENCE: 43

```
Met Lys Thr Ile Ile Ala Leu Ser Tyr Ile Phe Cys Gln Val Leu Ala
1               5                   10                  15

Gln Asn Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Gly Phe Asn Trp Thr
    130                 135                 140

Gly Val Thr Gln Asn Gly Gly Ser Tyr Ala Cys Lys Arg Gly Pro Asp
145                 150                 155                 160

Lys Ser Phe Phe Ser Arg Leu Asn Trp Leu Tyr Glu Ser Glu Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asp Lys Glu Gln Thr
            195                 200                 205

Asn Leu Tyr Val Gln Ala Ser Gly Arg Val Thr Val Ser Thr Lys Arg
    210                 215                 220

Ser Gln Gln Thr Ile Ile Pro Asn Val Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Asn Gly Asn Leu Ile Ala Pro Arg Gly
            260                 265                 270
```

-continued

```
Tyr Phe Lys Ile Arg Thr Gly Lys Ser Ser Ile Met Arg Ser Asp Ala
        275                 280                 285

Pro Ile Gly Thr Cys Ser Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Ile Asp Gly Trp Tyr Gly
                355                 360                 365

Phe Arg His Gln Asn Ser Glu Gly Thr Gly Gln Ala Ala Asp Leu Lys
        370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
        450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Gly Ser His His His His His
        515                 520                 525

His
```

<210> SEQ ID NO 44
<211> LENGTH: 538
<212> TYPE: PRT
<213> ORGANISM: Artificial Sequence
<220> FEATURE:
<223> OTHER INFORMATION: UFV181097

<400> SEQUENCE: 44

```
Met Lys Thr Ile Ile Ala Leu Ser Tyr Ile Leu Cys Leu Val Phe Ala
1                   5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95
```

-continued

```
Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
            195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg Trp Gln Asn Ser Glu Gly Ile Gly Gln Ala Ala Asp Leu Lys
    370                 375                 380

Ser Thr Gln Ala Ala Ile Asn Gln Ile Asn Gly Ile Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Ile
            435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Ser Gly Ser Leu Pro Glu Thr
```

```
              515                 520                 525

Gly Gly Gly Ser His His His His His
      530                 535

<210> SEQ ID NO 45
<211> LENGTH: 529
<212> TYPE: PRT
<213> ORGANISM: Artificial Sequence
<220> FEATURE:
<223> OTHER INFORMATION: UFV181138

<400> SEQUENCE: 45

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
```

-continued

```
                340                 345                 350
Gly Phe Ile Glu Asn Gly Trp Glu Gly Met Val Asp Gly Trp Tyr Gly
            355                 360                 365
Phe Arg His Gln Asn Ser Glu Gly Ile Gly Gln Ala Ala Asp Leu Lys
        370                 375                 380
Ser Thr Gln Ala Ala Ile Asn Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
        450                 455                 460
Glu Arg Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Gly Ser His His His His
        515                 520                 525
His
```

<210> SEQ ID NO 46
<211> LENGTH: 527
<212> TYPE: PRT
<213> ORGANISM: Artificial Sequence
<220> FEATURE:
<223> OTHER INFORMATION: UFV181148

<400> SEQUENCE: 46

```
Met Leu Ser Ile Val Ile Leu Phe Leu Leu Val Ala Glu Asn Ser Ser
1               5                   10                  15
Gln Asn Tyr Thr Gly Asn Pro Val Ile Cys Met Gly His His Ala Val
            20                  25                  30
Ala Asn Gly Thr Met Val Lys Thr Leu Thr Asp Asp Gln Val Glu Val
        35                  40                  45
Val Thr Ala Gln Glu Leu Val Glu Ser Gln Asn Leu Pro Glu Leu Cys
    50                  55                  60
Pro Ser Pro Leu Arg Leu Val Asp Gly Gln Thr Cys Asp Ile Ile Asn
65                  70                  75                  80
Gly Ala Leu Gly Ser Pro Gly Cys Asp His Leu Asn Gly Ala Glu Trp
                85                  90                  95
Asp Val Phe Ile Glu Arg Pro Asn Ala Met Asp Thr Cys Tyr Pro Phe
            100                 105                 110
Asp Val Pro Asp Tyr Gln Ser Leu Arg Ser Ile Leu Ala Asn Asn Gly
        115                 120                 125
Lys Phe Glu Phe Ile Ala Glu Glu Phe Gln Trp Thr Thr Val Lys Gln
        130                 135                 140
Asn Gly Lys Ser Gly Ala Cys Lys Arg Ala Asn Val Asn Asp Phe Phe
145                 150                 155                 160
Arg Arg Leu Asn Trp Leu Val Lys Ser Asp Arg Asn Ala Tyr Pro Leu
                165                 170                 175
```

-continued

```
Gln Asn Leu Thr Lys Val Asn Asn Gly Asp Tyr Ala Arg Leu Tyr Ile
            180                 185                 190

Trp Gly Val His His Pro Ser Thr Asp Thr Glu Gln Thr Asn Leu Tyr
            195                 200                 205

Lys Asn Asn Pro Gly Arg Val Thr Val Ser Thr Lys Thr Ser Gln Thr
            210                 215                 220

Ser Val Ile Pro Asn Ile Gly Ser Arg Pro Trp Val Arg Gly Gln Ser
225                 230                 235                 240

Gly Arg Ile Ser Phe Tyr Trp Thr Ile Val Glu Pro Gly Asp Leu Ile
                245                 250                 255

Val Phe Asn Thr Ile Gly Asn Leu Ile Ala Pro Arg Gly His Tyr Lys
            260                 265                 270

Leu Asn Asn Gln Lys Lys Gly Thr Ile Leu Asn Thr Ala Ile Pro Ile
            275                 280                 285

Gly Ser Cys Val Ser Lys Cys His Thr Asp Lys Gly Ser Leu Ser Thr
            290                 295                 300

Thr Lys Pro Phe Gln Asn Ile Ser Arg Ile Ala Ile Gly Asp Cys Pro
305                 310                 315                 320

Lys Tyr Val Lys Gln Gly Ser Leu Lys Leu Ala Thr Gly Met Arg Asn
                325                 330                 335

Ile Pro Glu Lys Ala Ser Arg Gly Leu Phe Gly Ala Ile Ala Gly Phe
            340                 345                 350

Ile Glu Asn Gly Trp Gln Gly Leu Ile Asp Gly Trp Tyr Gly Phe Arg
            355                 360                 365

His Gln Asn Ala Glu Gly Thr Gly Thr Ala Ala Asp Leu Lys Ser Thr
            370                 375                 380

Gln Ala Ala Ile Asp Gln Ile Asn Gly Lys Leu Asn Arg Leu Ile Glu
385                 390                 395                 400

Lys Thr Asn Glu Lys Tyr His Gln Ile Glu Lys Glu Phe Glu Gln Val
                405                 410                 415

Glu Gly Arg Ile Gln Asp Leu Glu Lys Tyr Val Glu Asp Thr Lys Ile
            420                 425                 430

Asp Leu Trp Ser Tyr Asn Ala Glu Leu Leu Val Ala Leu Glu Asn Gln
            435                 440                 445

His Thr Ile Asp Val Thr Asp Ser Glu Met Asn Lys Leu Phe Glu Arg
            450                 455                 460

Val Arg Arg Gln Leu Arg Glu Asn Ala Glu Asp Lys Gly Asn Gly Cys
465                 470                 475                 480

Phe Glu Ile Phe His Lys Cys Asp Asn Asn Cys Ile Glu Ser Ile Arg
                485                 490                 495

Asn Gly Thr Tyr Asp His Asp Ile Tyr Arg Asp Glu Ala Ile Asn Asn
            500                 505                 510

Arg Phe Gln Ile Gln Gly Val Gly Ser His His His His His His
            515                 520                 525
```

```
<210> SEQ ID NO 47
<211> LENGTH: 536
<212> TYPE: PRT
<213> ORGANISM: Artificial Sequence
<220> FEATURE:
<223> OTHER INFORMATION: UFV181149

<400> SEQUENCE: 47

Met Leu Ser Ile Val Ile Leu Phe Leu Leu Val Ala Glu Asn Ser Ser
1                   5                   10                  15
```

-continued

```
Gln Asn Tyr Thr Gly Asn Pro Val Ile Cys Met Gly His His Ala Val
        20              25              30

Ala Asn Gly Thr Met Val Lys Thr Leu Thr Asp Asp Gln Val Glu Val
        35              40              45

Val Thr Ala Gln Glu Leu Val Glu Ser Gln Asn Leu Pro Glu Leu Cys
    50              55              60

Pro Ser Pro Leu Arg Leu Val Asp Gly Gln Thr Cys Asp Ile Ile Asn
65              70              75              80

Gly Ala Leu Gly Ser Pro Gly Cys Asp His Leu Asn Gly Ala Glu Trp
                85              90              95

Asp Val Phe Ile Glu Arg Pro Asn Ala Met Asp Thr Cys Tyr Pro Phe
            100             105             110

Asp Val Pro Asp Tyr Gln Ser Leu Arg Ser Ile Leu Ala Asn Asn Gly
            115             120             125

Lys Phe Glu Phe Ile Ala Glu Glu Phe Gln Trp Thr Thr Val Lys Gln
    130             135             140

Asn Gly Lys Ser Gly Ala Cys Lys Arg Ala Asn Val Asn Asp Phe Phe
145             150             155             160

Arg Arg Leu Asn Trp Leu Val Lys Ser Asp Arg Asn Ala Tyr Pro Leu
                165             170             175

Gln Asn Leu Thr Lys Val Asn Asn Gly Asp Tyr Ala Arg Leu Tyr Ile
            180             185             190

Trp Gly Val His His Pro Ser Thr Asp Thr Glu Gln Thr Asn Leu Tyr
            195             200             205

Lys Asn Asn Pro Gly Arg Val Thr Val Ser Thr Lys Thr Ser Gln Thr
    210             215             220

Ser Val Ile Pro Asn Ile Gly Ser Arg Pro Trp Val Arg Gly Gln Ser
225             230             235             240

Gly Arg Ile Ser Phe Tyr Trp Thr Ile Val Glu Pro Gly Asp Leu Ile
                245             250             255

Val Phe Asn Thr Ile Gly Asn Leu Ile Ala Pro Arg Gly His Tyr Lys
            260             265             270

Leu Asn Asn Gln Lys Lys Gly Thr Ile Leu Asn Thr Ala Ile Pro Ile
            275             280             285

Gly Ser Cys Val Ser Lys Cys His Thr Asp Lys Gly Ser Leu Ser Thr
    290             295             300

Thr Lys Pro Phe Gln Asn Ile Ser Arg Ile Ala Ile Gly Asp Cys Pro
305             310             315             320

Lys Tyr Val Lys Gln Gly Ser Leu Lys Leu Ala Thr Gly Met Arg Asn
                325             330             335

Ile Pro Glu Lys Ala Ser Arg Gly Leu Phe Gly Ala Ile Ala Gly Phe
            340             345             350

Ile Glu Asn Gly Trp Gln Gly Leu Ile Asp Gly Trp Tyr Gly Phe Arg
            355             360             365

Trp Gln Asn Ala Glu Gly Thr Gly Thr Ala Ala Asp Leu Lys Ser Thr
    370             375             380

Gln Ala Ala Ile Asp Gln Ile Asn Gly Ile Leu Asn Arg Leu Ile Glu
385             390             395             400

Lys Thr Asn Glu Lys Tyr His Gln Ile Glu Lys Glu Phe Glu Gln Val
                405             410             415

Glu Gly Arg Ile Gln Asp Leu Glu Lys Tyr Val Glu Asp Thr Lys Ile
            420             425             430
```

-continued

```
Asp Leu Trp Ser Tyr Asn Ala Glu Leu Leu Val Ala Leu Ile Asn Gln
        435                 440                 445

His Thr Ile Asp Val Thr Asp Ser Glu Met Asn Lys Leu Phe Glu Arg
        450                 455                 460

Val Arg Arg Gln Leu Arg Glu Asn Ala Glu Asp Lys Gly Asn Gly Cys
465                 470                 475                 480

Phe Glu Ile Phe His Lys Cys Asp Asn Asn Cys Ile Glu Ser Ile Arg
                485                 490                 495

Asn Gly Thr Tyr Asp His Asp Ile Tyr Arg Asp Glu Ala Ile Asn Asn
                500                 505                 510

Arg Phe Gln Ile Gln Gly Val Ser Gly Ser Leu Pro Glu Thr Gly Gly
        515                 520                 525

Gly Ser His His His His His His
        530                 535
```

<210> SEQ ID NO 48

<400> SEQUENCE: 48

000

<210> SEQ ID NO 49

<400> SEQUENCE: 49

000

<210> SEQ ID NO 50
<211> LENGTH: 538
<212> TYPE: PRT
<213> ORGANISM: Artificial Sequence
<220> FEATURE:
<223> OTHER INFORMATION: UFV190839

<400> SEQUENCE: 50

```
Met Lys Thr Ile Ile Ala Leu Ser Tyr Ile Phe Cys Leu Ala Leu Gly
1                   5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
        130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
```

-continued

```
                180              185              190

Leu Tyr Ile Trp Gly Val His His Pro Ser Thr Asn Gln Glu Gln Thr
        195              200              205

Ser Leu Tyr Val Gln Ala Ser Gly Arg Val Thr Val Ser Thr Arg Arg
    210              215              220

Ser Gln Gln Thr Ile Ile Pro Asn Ile Gly Ser Arg Pro Trp Val Arg
225              230              235              240

Gly Leu Ser Ser Arg Ile Ser Ile Tyr Trp Thr Ile Val Lys Pro Gly
            245              250              255

Asp Val Leu Val Ile Asn Ser Asn Gly Asn Leu Ile Ala Pro Arg Gly
            260              265              270

Tyr Phe Lys Met Arg Thr Gly Lys Ser Ser Ile Met Arg Ser Asp Ala
        275              280              285

Pro Ile Asp Thr Cys Ile Ser Glu Cys Ile Thr Pro Asn Gly Ser Ile
        290              295              300

Pro Asn Asp Lys Pro Phe Gln Asn Val Asn Lys Ile Thr Tyr Gly Ala
305              310              315              320

Cys Pro Lys Tyr Val Lys Gln Asn Thr Leu Lys Leu Ala Thr Gly Met
            325              330              335

Arg Asn Val Pro Glu Lys Gln Thr Arg Gly Leu Phe Gly Ala Ile Ala
            340              345              350

Gly Phe Ile Glu Asn Gly Trp Glu Gly Met Ile Asp Gly Trp Tyr Gly
        355              360              365

Phe Arg Trp Gln Asn Ser Glu Gly Thr Gly Gln Ala Ala Asp Leu Lys
    370              375              380

Ser Thr Gln Ala Ala Ile Asp Gln Ile Asn Gly Ile Leu Asn Arg Val
385              390              395              400

Ile Glu Lys Thr Asn Glu Lys Phe His Gln Ile Glu Lys Glu Phe Ser
            405              410              415

Glu Val Glu Gly Arg Ile Gln Asp Leu Glu Lys Tyr Val Glu Asp Thr
            420              425              430

Lys Ile Asp Leu Trp Ser Tyr Asn Ala Glu Leu Leu Val Ala Leu Ile
        435              440              445

Asn Gln His Thr Ile Asp Leu Thr Asp Ser Glu Met Asn Lys Leu Phe
    450              455              460

Glu Lys Thr Arg Arg Gln Leu Arg Glu Asn Ala Glu Asp Met Gly Asn
465              470              475              480

Gly Cys Phe Lys Ile Tyr His Lys Cys Asp Asn Ala Cys Ile Glu Ser
            485              490              495

Ile Arg Asn Gly Thr Tyr Asp His Asp Val Tyr Arg Asp Glu Ala Leu
            500              505              510

Asn Asn Arg Phe Gln Ile Lys Gly Val Ser Gly Ser Leu Pro Glu Thr
        515              520              525

Gly Gly Gly Ser His His His His His
    530              535
```

```
<210> SEQ ID NO 51
<211> LENGTH: 532
<212> TYPE: PRT
<213> ORGANISM: Artificial Sequence
<220> FEATURE:
<223> OTHER INFORMATION: UFV190068

<400> SEQUENCE: 51

Met Asn Thr Gln Ile Leu Val Phe Ala Leu Met Ala Ile Ile Pro Thr
```

-continued

```
1               5               10              15

Asn Ala Asp Lys Ile Cys Leu Gly His His Ala Val Ser Asn Gly Thr
            20              25              30

Lys Val Asn Thr Leu Thr Glu Arg Gly Val Glu Val Val Asn Ala Thr
            35              40              45

Glu Thr Val Glu Arg Thr Asn Val Pro Arg Ile Cys Ser Lys Gly Lys
    50              55              60

Arg Thr Val Asp Leu Gly Gln Cys Gly Leu Leu Gly Thr Ile Thr Gly
65              70              75              80

Pro Pro Gln Cys Asp Gln Phe Leu Glu Phe Ser Ala Asp Leu Ile Ile
            85              90              95

Glu Arg Arg Glu Gly Ser Asp Val Cys Tyr Pro Gly Lys Phe Val Asn
            100             105             110

Glu Glu Ala Leu Arg Gln Ile Leu Arg Glu Ser Gly Gly Ile Asp Lys
            115             120             125

Glu Thr Met Gly Phe Thr Tyr Ser Gly Ile Arg Thr Asn Gly Ala Thr
    130             135             140

Ser Ala Cys Arg Arg Ser Gly Ser Ser Phe Tyr Ala Glu Met Lys Trp
145             150             155             160

Leu Leu Ser Asn Thr Asp Asn Ala Ala Phe Pro Gln Met Thr Lys Ser
            165             170             175

Tyr Lys Asn Thr Arg Lys Asp Pro Ala Leu Ile Ile Trp Gly Ile His
            180             185             190

His Ser Gly Ser Thr Thr Glu Gln Thr Lys Leu Tyr Gly Ser Gly Asn
            195             200             205

Lys Leu Ile Thr Val Gly Ser Ser Asn Tyr Gln Gln Ser Phe Val Pro
    210             215             220

Ser Pro Gly Ala Arg Pro Gln Val Asn Gly Gln Ser Gly Arg Ile Asp
225             230             235             240

Phe His Trp Leu Ile Leu Asn Pro Asn Asp Thr Val Thr Phe Ser Phe
            245             250             255

Asn Gly Ala Phe Ile Ala Pro Asp Arg Ala Ser Phe Leu Arg Gly Lys
            260             265             270

Ser Met Gly Ile Gln Ser Gly Val Gln Val Asp Ala Asn Cys Glu Gly
            275             280             285

Asp Cys Tyr His Ser Gly Gly Thr Ile Ile Ser Asn Leu Pro Phe Gln
    290             295             300

Asn Ile Asn Ser Arg Ala Val Gly Lys Cys Pro Arg Tyr Val Lys Gln
305             310             315             320

Glu Ser Leu Leu Leu Ala Thr Gly Met Lys Asn Val Pro Glu Ile Pro
            325             330             335

Lys Gly Arg Gly Leu Phe Gly Ala Ile Ala Gly Phe Ile Glu Asn Gly
            340             345             350

Trp Glu Gly Leu Ile Asp Gly Trp Tyr Gly Phe Arg Trp Gln Asn Ala
            355             360             365

Gln Gly Glu Gly Thr Ala Ala Asp Tyr Lys Ser Thr Gln Ser Ala Ile
    370             375             380

Asp Gln Ile Thr Gly Ile Leu Asn Arg Leu Ile Glu Lys Thr Asn Gln
385             390             395             400

Gln Phe Glu Leu Ile Asp Asn Glu Phe Thr Glu Val Glu Lys Gln Ile
            405             410             415

Gly Asn Val Ile Asn Trp Thr Arg Asp Ser Met Thr Glu Val Trp Ser
            420             425             430
```

-continued

```
Tyr Asn Ala Glu Leu Leu Val Ala Met Ile Asn Gln His Thr Ile Asp
        435             440             445

Leu Ala Asp Ser Glu Met Asn Lys Leu Tyr Glu Arg Val Lys Arg Gln
        450             455             460

Leu Arg Glu Asn Ala Glu Glu Asp Gly Thr Gly Cys Phe Glu Ile Phe
465             470             475             480

His Lys Cys Asp Asp Asp Cys Met Ala Ser Ile Arg Asn Asn Thr Tyr
                485             490             495

Asp His Ser Lys Tyr Arg Glu Glu Ala Met Gln Asn Arg Ile Gln Ile
                500             505             510

Asp Pro Val Ser Gly Ser Leu Pro Glu Thr Gly Gly Ser His His
        515             520             525

His His His His
        530

<210> SEQ ID NO 52
<211> LENGTH: 531
<212> TYPE: PRT
<213> ORGANISM: Artificial Sequence
<220> FEATURE:
<223> OTHER INFORMATION: UFV190841

<400> SEQUENCE: 52

Met Tyr Lys Val Val Val Ile Ile Ala Leu Leu Gly Ala Val Lys Gly
1               5               10              15

Asp Arg Ile Cys Leu Gly His His Ala Val Ala Asn Gly Thr Ile Val
                20              25              30

Lys Thr Leu Thr Asn Glu Gln Glu Glu Val Thr Asn Ala Thr Glu Thr
        35              40              45

Val Glu Ser Thr Asn Leu Asn Lys Leu Cys Met Lys Gly Arg Ser Tyr
        50              55              60

Lys Asp Leu Gly Asn Cys His Pro Val Gly Met Leu Ile Gly Thr Pro
65              70              75              80

Val Cys Asp Pro His Leu Thr Gly Thr Trp Asp Thr Leu Ile Glu Arg
                85              90              95

Glu Asn Ala Ile Ala His Cys Tyr Pro Gly Ala Thr Ile Asn Glu Glu
                100             105             110

Ala Leu Arg Gln Lys Ile Met Glu Ser Gly Gly Ile Ser Lys Met Ser
        115             120             125

Thr Gly Phe Thr Tyr Gly Ser Ser Ile Asn Ser Ala Gly Thr Thr Lys
        130             135             140

Ala Cys Met Arg Asn Gly Gly Asp Ser Phe Tyr Ala Glu Leu Lys Trp
145             150             155             160

Leu Val Ser Lys Thr Lys Gly Gln Asn Phe Pro Gln Thr Thr Asn Thr
                165             170             175

Tyr Arg Asn Thr Asp Thr Ala Glu His Leu Ile Ile Trp Gly Ile His
                180             185             190

His Pro Ser Ser Thr Gln Glu Lys Asn Asp Leu Tyr Gly Thr Gln Ser
        195             200             205

Leu Ser Ile Ser Val Glu Ser Ser Thr Tyr Gln Asn Asn Phe Val Pro
        210             215             220

Val Val Gly Ala Arg Pro Gln Val Asn Gly Gln Ser Gly Arg Ile Asp
225             230             235             240

Phe His Trp Thr Leu Val Gln Pro Gly Asp Asn Ile Thr Phe Ser His
                245             250             255
```

```
Asn Gly Gly Leu Ile Ala Pro Ser Arg Val Ser Lys Leu Thr Gly Arg
            260                 265                 270

Gly Leu Gly Ile Gln Ser Glu Ala Leu Ile Asp Asn Ser Cys Glu Ser
            275                 280                 285

Lys Cys Phe Trp Arg Gly Gly Ser Ile Asn Thr Lys Leu Pro Phe Gln
    290                 295                 300

Asn Leu Ser Pro Arg Thr Val Gly Gln Cys Pro Lys Tyr Val Asn Gln
305                 310                 315                 320

Arg Ser Leu Leu Leu Ala Thr Gly Met Arg Asn Val Pro Glu Val Val
            325                 330                 335

Gln Gly Arg Gly Leu Phe Gly Ala Ile Ala Gly Phe Ile Glu Asn Gly
            340                 345                 350

Trp Glu Gly Met Val Asp Gly Trp Tyr Gly Phe Arg Trp Gln Asn Ala
            355                 360                 365

Gln Gly Thr Gly Gln Ala Ala Asp Tyr Lys Ser Thr Gln Ala Ala Ile
    370                 375                 380

Asp Gln Ile Thr Gly Ile Leu Asn Arg Leu Ile Glu Lys Thr Asn Thr
385                 390                 395                 400

Glu Phe Glu Ser Ile Glu Ser Glu Phe Ser Glu Thr Glu His Gln Ile
            405                 410                 415

Gly Asn Val Ile Asn Trp Thr Lys Asp Ser Ile Thr Asp Ile Trp Thr
            420                 425                 430

Tyr Gln Ala Glu Leu Leu Val Ala Met Ile Asn Gln His Thr Ile Asp
            435                 440                 445

Met Ala Asp Ser Glu Met Leu Asn Leu Tyr Glu Arg Val Arg Lys Gln
    450                 455                 460

Leu Arg Gln Asn Ala Glu Glu Asp Gly Lys Gly Cys Phe Glu Ile Tyr
465                 470                 475                 480

His Thr Cys Asp Asp Ser Cys Met Glu Ser Ile Arg Asn Asn Thr Tyr
            485                 490                 495

Asp His Ser Gln Tyr Arg Glu Glu Ala Leu Leu Asn Arg Leu Asn Ile
            500                 505                 510

Asn Ser Ser Gly Ser Leu Pro Glu Thr Gly Gly Gly Ser His His His
            515                 520                 525

His His His
    530
```